US012201402B2

(12) United States Patent
Connor

(10) Patent No.: US 12,201,402 B2
(45) Date of Patent: Jan. 21, 2025

(54) WEARABLE DEVICE (SMART BRA) WITH COMPRESSIVE CHAMBERS AND OPTICAL SENSORS FOR ANALYZING BREAST TISSUE

(71) Applicant: Robert A. Connor, St. Paul, MN (US)

(72) Inventor: Robert A. Connor, St. Paul, MN (US)

(73) Assignee: Holovisions LLC, Ham Lake, MN (US)

( * ) Notice: Subject to any disclaimer, the term of this patent is extended or adjusted under 35 U.S.C. 154(b) by 12 days.

(21) Appl. No.: 18/096,748

(22) Filed: Jan. 13, 2023

(65) Prior Publication Data

US 2023/0148868 A1 May 18, 2023

Related U.S. Application Data

(63) Continuation-in-part of application No. 17/897,182, filed on Aug. 28, 2022, now Pat. No. 11,950,881, which is a continuation-in-part of application No. 16/933,138, filed on Jul. 20, 2020, now abandoned.

(60) Provisional application No. 62/879,485, filed on Jul. 28, 2019.

(51) Int. Cl.
A61B 5/00 (2006.01)
A41C 3/00 (2006.01)

(52) U.S. Cl.
CPC .......... *A61B 5/0091* (2013.01); *A61B 5/0064* (2013.01); *A61B 5/6804* (2013.01); *A61B 5/6844* (2013.01); *A41C 3/0064* (2013.01)

(58) Field of Classification Search
None
See application file for complete search history.

(56) References Cited

U.S. PATENT DOCUMENTS

| 5,056,505 A | * 10/1991 | Warwick ........... A61M 16/0006 601/44 |
| 5,876,339 A | 3/1999 | Lemire |
| 5,999,836 A | 12/1999 | Nelson et al. |
| 6,081,322 A | 6/2000 | Barbour |
| 6,240,309 B1 | 5/2001 | Yamashita et al. |
| 6,345,194 B1 | 2/2002 | Nelson et al. |
| 6,571,116 B2 | 5/2003 | Wake et al. |
| 6,640,133 B2 | 10/2003 | Yamashita et al. |

(Continued)

FOREIGN PATENT DOCUMENTS

WO WO 2010082993 A2 * 7/2010 ............... A61B 5/02

OTHER PUBLICATIONS

Breast compression and radiation dose in two different mammographic oblique projections: 45 and 60° by Brnić et al. European Journal of Radiology, vol. 40, Issue 1, 2001, ISSN 0720-048X, https://doi.org/10.1016/S0720-048X(01)00317-5. (Year: 2001).*

(Continued)

*Primary Examiner* — Pascal M Bui Pho
*Assistant Examiner* — Michael S Kellogg

(57) ABSTRACT

This invention is a wearable device or system for optical analysis of breast tissue which be embodied in a "smart bra" or an insert which is placed into the cup of a conventional bra. This device or system has light emitters which transmit light into breast tissue and light receivers which receive the light after it has been transmitted through the breast tissue. It also has expandable chambers which gently compress a breast to reduce light diffusion and improve optical scanning of breast tissue.

1 Claim, 14 Drawing Sheets

(56) References Cited

U.S. PATENT DOCUMENTS

| | | | |
|---|---|---|---|
| 6,738,658 | B2 | 5/2004 | Wake et al. |
| RE38,800 | E | 9/2005 | Barbour |
| 7,142,906 | B2 | 11/2006 | Yamashita et al. |
| 7,809,422 | B2 | 10/2010 | Corbeil et al. |
| 7,904,139 | B2 | 3/2011 | Chance |
| 8,027,711 | B2 | 9/2011 | Jones et al. |
| 8,224,426 | B2 | 7/2012 | Lilge et al. |
| 8,565,862 | B2 | 10/2013 | Intes et al. |
| 9,314,218 | B2 | 4/2016 | Stearns et al. |
| 9,495,516 | B2 | 11/2016 | Hielscher et al. |
| 9,513,276 | B2 | 12/2016 | Tearney et al. |
| 9,597,046 | B2 | 3/2017 | Goossen et al. |
| 9,724,489 | B2 | 8/2017 | Barbour et al. |
| 9,770,220 | B2 | 9/2017 | Stearns et al. |
| 9,993,159 | B2 | 6/2018 | Islam |
| 10,111,594 | B2 | 10/2018 | Hielscher et al. |
| 10,130,318 | B2 | 11/2018 | Stearns et al. |
| 10,178,967 | B2 | 1/2019 | Hielscher et al. |
| 10,200,655 | B2 | 2/2019 | Kim et al. |
| 10,215,636 | B2 | 2/2019 | Fujii et al. |
| 10,376,150 | B2 | 8/2019 | Hielscher et al. |
| 10,506,181 | B2 | 12/2019 | Delgado et al. |
| 10,653,346 | B2 | 5/2020 | Zarandi et al. |
| 2002/0045833 | A1 | 4/2002 | Wake et al. |
| 2004/0092826 | A1 | 5/2004 | Corbeil et al. |
| 2005/0043596 | A1 | 2/2005 | Chance |
| 2006/0058683 | A1 | 3/2006 | Chance |
| 2006/0173352 | A1 | 8/2006 | Lilge et al. |
| 2007/0287897 | A1* | 12/2007 | Faris ............... A61B 5/0091 424/9.1 |
| 2009/0005692 | A1 | 1/2009 | Intes et al. |
| 2010/0292569 | A1 | 11/2010 | Hielscher et al. |
| 2011/0065358 | A1* | 3/2011 | Fleeton ............. A41C 3/0028 450/38 |
| 2013/0289394 | A1 | 10/2013 | Hielscher et al. |
| 2013/0338496 | A1 | 12/2013 | Hielscher et al. |
| 2014/0088415 | A1 | 3/2014 | Hielscher et al. |
| 2014/0236003 | A1 | 8/2014 | Hielscher et al. |
| 2014/0236021 | A1 | 8/2014 | Islam |
| 2014/0243681 | A1 | 8/2014 | Hielscher et al. |
| 2014/0330116 | A1 | 11/2014 | Hielscher et al. |
| 2015/0119665 | A1 | 4/2015 | Barbour et al. |
| 2015/0182121 | A1* | 7/2015 | Barbour ............. A61B 5/0073 600/425 |
| 2015/0223697 | A1 | 8/2015 | Hielscher et al. |
| 2015/0286785 | A1 | 10/2015 | Hielscher et al. |
| 2016/0066811 | A1 | 3/2016 | Mohamadi |
| 2017/0007187 | A1 | 1/2017 | Breneisen et al. |
| 2017/0027480 | A1 | 2/2017 | Hielscher et al. |
| 2017/0105625 | A1 | 4/2017 | Eum |
| 2017/0209093 | A1 | 7/2017 | Zarandi et al. |
| 2018/0070891 | A1 | 3/2018 | Jepsen |
| 2018/0126052 | A1* | 5/2018 | Looney ............... A61M 1/06 |
| 2018/0289264 | A1 | 10/2018 | Islam |
| 2018/0335753 | A1 | 11/2018 | Jepsen et al. |
| 2019/0072897 | A1 | 3/2019 | Jepsen et al. |
| 2019/0150526 | A1* | 5/2019 | Lehna ................. A41C 3/06 |
| 2019/0239751 | A1 | 8/2019 | Hielscher et al. |
| 2019/0282134 | A1 | 9/2019 | Hielscher et al. |
| 2020/0116630 | A1 | 4/2020 | Zhu |
| 2021/0038083 | A1 | 2/2021 | Islam |

OTHER PUBLICATIONS

Ahmed et al., (2021), "Differential Optical Absorption Spectroscopy-Based Refractive Index Sensor for Cancer Cell Detection," Optical Review, 28, 134-143.

Altoe et al., (2019), "Diffuse Optical Tomography of the Breast: A Potential Modifiable Biomarker of Breast Cancer Risk with Neoadjuvant Chemotherapy," Biomedical Optics Express, Aug. 1, 2019, 10(8). 4305-4315.

Altoe et al., (2021), "Changes in Diffuse Optical Tomography Images During Early Stages of Neoadjuvant Chemotherapy Correlate with Tumor Response in Different Breast Cancer Subtypes", Clinical Cancer Research. Apr. 1, 2021 27(7), 1949-1957.

Altoe et al., (2021), "Effects of Neoadjuvant Chemotherapy on the Contralateral Non-Tumor-Bearing Breast Assessed by Diffuse Optical Tomography," Breast Cancer Research, 2021, 23, 16.

Anabestani et al. (2022), "Advances in Flexible Organic Photodetectors: Materials and Applications," Nanomaterials, 2022, 12(21), 3775.

Anderson et al., (2017), "Optical Mammography in Patients with Breast Cancer Undergoing Neoadjuvant Chemotherapy: Individual Clinical Response Index," Academic Radiology, Oct. 2017, 24(10), 1240-1255.

Angelo et al., (2018), "Review of Structured Light in Diffuse Optical Imaging," Journal of Biomedical Optics, Sep. 14, 2018, 24(7), 071602.

Applegate et al. (2020), "Recent Advances in High Speed Diffuse Optical Imaging in Biomedicine," APL Photonics, 2020, 5(4), 040802, 21.

Applegate et al., (2018), "Multi-Distance Diffuse Optical Spectroscopy with a Single Optode via Hypotrochoidal Scanning," Optics Letters, 2018, 43, 747-750.

Chae et al., (2020), "Development of Digital Breast Tomosynthesis and Diffuse Optical Tomography Fusion Imaging for Breast Cancer Detection," Scientific Reports, 10, 13127 (2020).

Chitnis et al. (2016), "Towards a Wearable Near Infrared Spectroscopic Probe for Monitoring Concentrations of Multiple Chromophores in Biological Tissue In Vivo," Review of Scientific Instruments, Jun. 2016, 87(6), 065112.

Cinquino et al. (2021), "Light-Emitting Textiles: Device Architectures, Working Principles, and Applications," Micromachines, (Special Issue Emerging and Disruptive Next-Generation Technologies for POC: Sensors, Chemistry and Microfluidics for Diagnostics), 2021, 12(6), 652.

Cochran et al., (2019), "Hybrid Time-Domain and Continuous-Wave Diffuse Optical Tomography Instrument with Concurrent, Clinical Magnetic Resonance Imaging for Breast Cancer Imaging," Journal of Biomedical Optics, Jan. 2019, 24(5), 1-11.

Costa et al. (2019), "Flexible Sensors: From Materials to Applications," Technologies (Special Issue and Advances in Internet of Things Technologies), 2019, 7(2), 35.

Durduran et al., (2010, 2010), "Diffuse Optics for Tissue Monitoring and Tomography," Reports on Progress in Physics, 2010, 73(7), 076701.

Fakayode et al., (2020), "Molecular (Raman, NIR, and FTIR) Spectroscopy and Multivariate Analysis in Consumable Products Analysis," Applied Spectroscopy, reviews, 55:8, 647-723.

Fantini (2005), "Optical Spectroscopy and Imaging of Tissues", NSF Award, 2005 (abstract only viewed).

Fantini et al., (2001), "Optical Spectroscopy and Imaging of Tissues," NSF Award # 0093840, Jun. 1, 2001.

Fantini et al., (2012), "Near-Infrared Optical Mammography for Breast Cancer Detection with Intrinsic Contrast," Annals of Biomedical Engineering, Feb., 2012, 40(2), 398-407.

Farmani et al., (2020), "Optical Nanosensors for Cancer and Virus Detections," Micro and Nano Technologies, Nanosensors for Smart Cities, Chapter 25, Han et al. editors, Elsevier, 2020, 419-432, ISBN 9780128198704.

Feng et al. (2021), "MRI Guided Wearable Near Infrared Spectral Tomography: Simulation Study," Proceedings SPIE, 11639, Optical Tomography and Spectroscopy of Tissue XIV, 116390D, Mar. 5, 2021.

Flexman et al., (2008), "The Design and Characterization of a Digital Optical Breast Cancer Imaging System," 30th Annual International Conference of the IEEE Engineering in Medicine and Biology Society, 2008, 3735-3738.

Ghijsen et al., (2018), "Quantitative Real-Time Optical Imaging of the Tissue Metabolic Rate of Oxygen Consumption," Journal of Biomedical Optics, Mar. 24, 2018, 23(3), 036013.

Grosenick et al., (2016), "Review of Optical Breast Imaging and Spectroscopy," Journal of Biomedical Optics, Sep. 2016, 21(9), 091311.

(56) References Cited

OTHER PUBLICATIONS

Gunther et al., (2018), "Dynamic Diffuse Optical Tomography for Monitoring Neoadjuvant Chemotherapy in Patients with Breast Cancer," Radiology, Jun. 2018; 287(3): 778-786.

Hoi et al., (2018), "Non-Contact Dynamic Diffuse Optical Tomography Imaging System for Evaluating Lower Extremity Vasculature," Biomedical Optics Express, 2018, 9, 5597-5614.

Imamura et al., (2018), "In Vivo Optical Imaging of Cancer Cell Function and Tumor Microenvironment," Cancer Science, 2018, 109, 912-918.

Intes et al. (2004), "Time-Domain Optical Mammography Softscan: Initial Results on Detection and Characterization of Breast Tumors," Proceedings SPIE 5578, Photonics North 2004: Photonic Applications in Astronomy, Biomedicine, Imaging, Materials Processing, Dec. 9, 2004.

Jeong et al., (2020), "Emerging Advanced Metasurfaces: Alternatives to Conventional Bulk Optical Devices," Microelectronic Engineering, 2020, vol. 220, 111146, ISSN 0167-9317.

Jiang et al. (2021), "MRI-Guide Near Infrared Spectroscopic Tomographic Imaging System with Wearable Optical Breast Interface for Breast Imaging," Proceedings SPIE, 11639, Optical Tomography and Spectroscopy of Tissue XIV, 116391J, Mar. 5, 2021.

Joshi et al., (2018), "Targeted Optical Imaging Agents in Cancer: Focus on Clinical Applications," Contrast Media and Molecular Imaging, Aug. 27, 2018.

Jung et al. (2015), "Non-Contact Deep Tissue Imaging using a Hand-Held Near-infrared Optical Scanner," Journal of Medical Diagnostic Methods, Mar. 24, 2015, 4(2), 1-10.

Khan (2013), "Image Reconstruction in Diffuse Optical Tomography With Sparsity Constraints", NSF Award, 2013 (abstract only viewed).

Kim et al., (2016), "US-Localized Diffuse Optical Tomography in Breast Cancer: Comparison with Pharmacokinetic Parameters of DCE-MRI and With Pathologic Biomarkers," BMC Cancer, Feb. 1, 2016, 16:50.

Koetse et al., (2007), "Optical Sensor Array Platform Based on Polymer Electronic Devices," Proceedings SPIE 6739, Electro-Optical Remote Sensing, Detection, and Photonic Technologies and Their Applications, 67391D, Nov. 7, 2007.

Koomson, 2019), "A Noninvasive Biological Research Tool for Measurement of Tissue and Cerebral Oxygenation," NSF Award # 1919038, Jul. 15, 2019, (abstract only viewed).

Krishnamurthy, 2018), "Using Near-Infrared Spectroscopy to Study Static and Dynamic Hemoglobin Contrast Associated with Breast Cancer," Tufts University, Dissertation, 2018.

Leo et al. (2017), "Optical Imaging of the Breast: Basic Principles and Clinical Applications," American Journal of Roentgenology, 2017, 209:1, 230-238.

Li et al. (2018), "Sensitive and Wearable Optical Microfiber Sensor for Human Health Monitoring," Advanced Materials Technologies, 2018, 3, 1800296.

Liu et al., (2018), "Diffuse Optical Spectroscopy for Monitoring the Responses of Patients with Breast Cancer to Neoadjuvant Chemotherapy: A Meta-Analysis," Medicine, 2018, 97(41), 12683.

Liu et al., (2020), "Recent Progress in Flexible Wearable Sensors for Vital Sign Monitoring," Sensors, 2020, 20(14), 4009.

Liu et al., (2021), "Simultaneous Measurements of Tissue Blood Flow and Oxygenation Using a Wearable Fiber-Free Optical Sensor," Journal of Biomedical Optics, Jan. 29, 2021, 26(1), 012705.

Lutzweiler et al., (2013), "Optoacoustic Imaging and Tomography: Reconstruction Approaches and Outstanding Challenges in Image Performance and Quantification," Sensors, 2013, 13(3), 7345-7384.

Ma et al. (2020b), "Fiber-Free Parallel-Plane Continuous Wave Breast Diffuse Optical Tomography System," SPIE 11229, Advanced Biomedical and Clinical Diagnostic and Surgical Guidance Systems XVIII, Proceedings, 112290L, Feb. 21, 2020.

Mabou et al., (2018), "Breast Cancer Detection Using Infrared Thermal Imaging and a Deep Learning Model," Sensors, 2018, 18(9), 2799.

Moreno et al. (2019), "Evaluation on Phantoms of the Feasibility of a Smart Bra to Detect Breast Cancer in Young Adults," Sensors, 2019, 19(24), 5491.

Nguyen et al., (2020), "Preliminary Development of Optical Computed Tomography (Optical CT) Scanner Using Transillumination Imaging NAD," Conference: International Symposium on Applied Science 2019 Hochiminh City, Vietnam, May 14, 2020.

Pan et al., (2020), "A Multifunctional Skin-Like Wearable Optical Sensor Based on an Optical Micro-/Nanofibre," Nanoscale, 2020, Issue 33.

Park et al., (2013), "Multispectral Imaging Using Polydimethylsiloxane (PDMS) Embedded Vertical Silicon Nanowires," OSA Technical Digest (online) (Optical Society of America, 2013), paper CTu3O.1.

Park et al., (2015), "Vertically Stacked Photodetector Devices Containing Silicon Nanowires with Engineered Absorption Spectra," ACS Photonics, Mar. 16, 2015, 2(4), 544-549.

Perumal et al., (2019), "Near Infra-Red Polymeric Nanoparticle Based Optical Imaging in Cancer Diagnosis," Journal of Photochemistry and Photobiology, Biology, 2019, vol. 199, 111630, ISSN 1011-1344.

Pinti et al. (2018), "A Review on the Use of Wearable Functional Near-Infrared Spectroscopy in Naturalistic Environments," Japanese Psychology Research, Oct. 2018, 60(4), 347-373.

Qiu (2018), "Implantable Ultra-low Power VO2 MEMS Scanner Based Surface-Enhanced Raman Spectroscope for Wide-field Tumor Imaging in Free Moving Small Animals", NSF Award, 2018 (abstract only viewed).

Rahman et al., (2016), "Electromagnetic Performances Analysis of an Ultra-Wideband and Flexible Material Antenna in Microwave Breast Imaging: To Implement a Wearable Medical Bra," Scientific Reports, 2016, vol. 6, 38906.

Ray et al. (2017), "A Systematic Review of Wearable Systems for Cancer Detection: Current State and Challenges," Journal of Medical Systems, Oct. 2, 2017, 41(11), 180.

Robbins et al. (2021), "Two-Layer Spatial Frequency Domain Imaging of Compression-Induced Hemodynamic Changes in Breast Tissue," Journal of Biomedical Optics, May 24, 2021, 26(5), 056005.

Roblyer et al. (2020b), "Tracking Breast Cancer Therapies with Handheld and Wearable Diffuse Optics," Biophotonics Congress: Biomedical Optics 2020 (Translational, Microscopy, OCT, OTS, BRAIN). OSA Technical Digest (Optical Society of America, 2020), paper TM4B.1.

Saikia et al. (2017), "A Cost-Effective LED and Photodetector Based Fast Direct 3D Diffuse Optical Imaging System," Proc. SPIE 10412, Diffuse Optical Spectroscopy and Imaging VI, Jul. 28, 2017, European Conferences on Biomedical Optics, 2017, Munich, Germany.

Saikia et al. (2019), "A Point-of-Care Handheld Region-of-Interest (ROI) 3D Functional Diffuse Optical Tomography (fDOT) System," Proc. SPIE 10874, Optical Tomography and Spectroscopy of Tissue XIII, Mar. 1, 2019.

Satharasinghe et al. (2018), "Photodiodes Embedded Within Electronic Textiles," Science Reports, 2018, 8, 16205.

Schoustra et al. (2021), "Pendant Breast Immobilization and Positioning in Photoacoustic Tomographic Imaging," Photoacoustics, 2021, 21, 100238.

Shokoufi et al. (2017), "Novel Handheld Diffuse Optical Spectroscopy Probe for Breast Cancer Assessment: Clinical Study," Journal of Biomedical Science, 6(5), 34.

Soliman et al., (2010), "Functional Imaging Using Diffuse Optical Spectroscopy of Neoadjuvant Chemotherapy Response in Women with Locally Advanced Breast Cancer," Clinical Cancer Research, Apr. 20, 2010, 15, 2605-2614.

Spink et al. (2020), "High Optode-Density Wearable Probe for Monitoring Breast Tumor Dynamics During Neoadjuvant Chemotherapy," Biophotonics Congress: Biomedical Optics 2020 (Translational, Microscopy. OCT. OTS BRAIN), OSA Technical Digest (OSA, 2020), paper TTu1B.2.

Spink et al. (2021), "High Optode-Density Wearable Diffuse Optical Probe for Monitoring Paced Breathing Hemodynamics in Breast Tissue," Journal of Biomedical Optics, Jun. 2, 2021, 26(6), 062708.

(56) References Cited

OTHER PUBLICATIONS

Tank et al. (2020), "Diffuse Optical Spectroscopic Imaging Reveals Distinct Early Breast Tumor Hemodynamic Responses to Metronomic and Maximum Tolerated Dose Regimens," Breast Cancer Research, 2020, 22, 29.
Teng (2018), "A Wearable Near-Infrared Diffuse Optical System for Monitoring in Vivo Breast Tumor Hemodynamics During Chemotherapy Infusions," Boston University, Dissertation, 2018.
Teng et al. (2017), "Wearable Near-Infrared Optical Probe for Continuous Monitoring During Breast Cancer Neoadjuvant Chemotherapy Infusions," Journal of Biomedical Optics, 22(1), 14001.
Tiwari et al. (2022), "Role of Sensor Technology in Detection of the Breast Cancer," BioNanoScience, 2022, 12, 639-659.
Tromberg et al., (2016), "ACRIN 6691 Investigators. Predicting Responses to Neoadjuvant C hemotherapy in Breast Cancer," Cancer Research, Aug. 15, 2016, 76(20), 5933-5944.
Uddin et al., (2020a), "Optimal Breast Cancer Diagnostic Strategy Using Combined Ultrasound and Diffuse Optical Tomography," Biomedical Optics Express, 11(5), 2722-2737.
Upputuri, (2019), "Photoacoustic Imaging in the Second Near-Infrared Window: A Review," Journal of Biomedical Optics, Apr. 9, 2019, 24(4), 040901.
Vavadi et al., (2018), "Compact Ultrasound-Guided Diffuse Optical Tomography System for Breast Cancer Imaging," Journal of Biomedical Optics, 2018, 24(2), 1-9.
Wang et al. (2020), "Development of a Prototype of a Wearable Flexible Electro-Optical Imaging System for the Breast," Biophotonics Congress: Biomedical Optics 2020 (Translational, Microscopy, OCT, OTS, BRAIN), OSA Technical Digest (Optical Society of America, 2020), paper TM4B.4.
Yu et al. (2010), "Near-Infrared, Broad-Band Spectral Imaging of the Human Breast for Quantitative Oximetry: Applications to Healthy and Cancerous Breasts," Journal of Innovative Optical Health Sciences, Oct. 2010, 03(4):267-277.
Yuan et al. (2014), "Light-Emitting Diode-Based Multiwavelength Diffuse Optical Tomography System Guided by Ultrasound," Journal of Biomedical Optics, Dec. 4, 2014, 19(12) 126003.
Zhang et al., (2020), "Efficacy of Shear-Wave Elastography Versus Dynamic Optical Breast Imaging for Predicting the Pathological Response to Neoadjuvant Chemotherapy in Breast Cancer," European Journal of Radiology, 2020, 129, 109098.
Zhao et al. (2021), "High Resolution, Deep Imaging Using Confocal Time-of-Flight Diffuse Optical Tomography," IEEE Transactions on Pattern Analysis and Machine Intelligence, Jul. 1, 2021, 43(7), 2206-2219.
Zhao et al. (2022), "MRI-Guided Near-Infrared Spectroscopic Tomography (MRg-NIRST): System Development for Wearable, Simultaneous NIRS and MRI Imaging," Proc. SPIE 11952, Multimodal Biomedical Imaging XVII, Mar. 2, 2022.
Zhu et al. (2020), "A Review of Optical Breast Imaging: Multi-Modality Systems for Breast Cancer Diagnosis," European Journal of Radiology, Aug. 2020, 129:109067.
Zhu et al., (2021), "Early Assessment Window for Predicting Breast Cancer Neoadjuvant Therapy Using Biomarkers, Ultrasound, and Diffuse Optical Tomography," Breast Cancer Research and Treatment 2021.

* cited by examiner

WEARABLE DEVICE (SMART BRA) WITH COMPRESSIVE CHAMBERS AND OPTICAL SENSORS FOR ANALYZING BREAST TISSUE

CROSS-REFERENCE TO RELATED APPLICATIONS

This application is a continuation-in-part of U.S. application Ser. No. 17/897,182 filed on 2022 Aug. 28. U.S. application Ser. No. 17/897,182 was a continuation-in-part of U.S. application Ser. No. 16/933,138 filed on 2020 Jul. 20. U.S. application Ser. No. 16/933,138 claimed the priority benefit of U.S. provisional application 62/879,485 filed on 2019 Jul. 28. The entire contents of these related applications are incorporated herein by reference

FEDERALLY SPONSORED RESEARCH

Not Applicable

SEQUENCE LISTING OR PROGRAM

Not Applicable

BACKGROUND

Field of Invention

This invention relates to wearable devices for medical imaging and diagnosis.

Introduction

Breast cancer is the most common form of cancer in women and a leading cause of death. Breast imaging can serve a critical role in the early diagnosis and treatment of breast cancer. However, there are limitations to frequent use of the current breast imaging modalities. Current modalities of breast imaging and/or abnormal tissue detection include: x-ray mammography (most common), Magnetic Resonance Imaging (MRI), and ultrasonography. Limitations of x-ray mammography include exposure to ionizing radiation. Limitations of Magnetic Resonance Imaging (MRI) include relatively low specificity, long exam times, and high cost. Limitations of ultrasound imaging include difficulty visualizing microcalcifications and strong dependence on examiner interpretation. General limitations of current modalities include required access to specialized facilities, examination time required, embarrassment and/or cultural barriers. There remains a need for a new breast imaging modality which can be used frequently and safely for breast imaging and tissue analysis.

During recent years, there has been increased investigation of the possibilities of optical breast imaging using safe non-ionizing radiation such as visible, ultraviolet, infrared, and near-infrared light energy. However, thus far there have been limitations to optical breast imaging. For example, with stationary devices, there can be air gaps between optical sensors and the surface of a breast which reduce scanning accuracy. Also, with handheld optical imaging devices, it can be difficult to accurately measure absolute tissue locations to track changes over time and to get a comprehensive image of the complete breast.

Review of the Relevant Art

In the patent literature, U.S. patent application 20050043596 (Chance, Feb. 24, 2005, "Optical Examination Device, System and Method") discloses a brush-form optical coupler with freely extending fiber end portions, sized and positioned to make optical contact with a subject, examination, and monitoring systems utilizing one or more of such couplers. U.S. patent application 20060058683 (Chance, Mar. 16, 2006, "Optical Examination of Biological Tissue Using Non-Contact Irradiation and Detection") and U.S. Pat. No. 7,904,139 (Chance, Mar. 8, 2011, "Optical Examination of Biological Tissue Using Non-Contact Irradiation and Detection") disclose an optical system for examination of biological tissue which includes a light source, a light detector, optics and electronics. Sometimes inventions are the result of serendipitous insights; in this case, optical scanning of biological tissue may actually have been invented by chance.

U.S. Pat. No. 6,081,322 (Barbour, Jun. 27, 2000, "NIR Clinical Opti-Scan System") and RE38800 (Barbour, Sep. 20, 2005, "NIR Clinical Opti-Scan System") disclose three-dimensional optical imaging techniques for the detection and three-dimensional imaging of absorbing and/or scattering structures in complex random media, such as human body tissue, by detecting scattered light. U.S. patent application 20150182121 (Barbour, Jul. 2, 2015, "Low-Cost Screening System for Breast Cancer Detection") discloses a portable and wearable tumor detector including a brassier and devices for optical tomography. U.S. patent application publication 20150119665 (Barbour et al., Apr. 30, 2015, "Self-Referencing Optical Measurement for Breast Cancer Detection") and U.S. Pat. No. 9,724,489 (Barbour et al., Aug. 8, 2017, "Self-Referencing Optical Measurement for Breast Cancer Detection") disclose obtaining optical data from a pair of breasts, employing a simultaneous bilateral referencing protocol, and employing a self-referencing data analysis method.

U.S. patent applications 20100292569 (Hielscher et al., Nov. 18, 2010, "Systems and Methods for Dynamic Imaging of Tissue Using Digital Optical Tomography") and 20150223697 (Hielscher et al., Aug. 13, 2015, "Systems and Methods for Dynamic Imaging of Tissue Using Digital Optical Tomography") disclose methods for imaging tissue using diffuse optical tomography including directing a amplitude modulated optical signals from optical signal sources. U.S. patent application 20140330116 (Hielscher et al., Nov. 6, 2014, "Systems and Methods for Simultaneous Multi-Directional Imaging for Capturing Tomographic Data") discloses devices, systems, and method for tomographic imaging in which light transmitted and backscattered surface light is imaged by an optical system that minimizes reflection back to the target object. U.S. patent applications 20130289394 (Hielscher et al., Oct. 31, 2013, "Dynamic Optical Tomographic Imaging Devices Methods and Systems"), 20170027480 (Hielscher et al., Feb. 2, 2017, "Dynamic Optical Tomographic Imaging Devices Methods and Systems"), and 20190282134 (Hielscher et al., Sep. 19, 2019, "Dynamic Optical Tomographic Imaging Devices Methods and Systems"), and U.S. patent Ser. No. 10/178, 967 (Hielscher et al., Jan. 15, 2019, "Dynamic Optical Tomographic Imaging Devices Methods and Systems") disclose an optical tomographic systems for acquiring and displaying dynamic data representing changes in a target tissue sample to external provocation. U.S. patent applications 20130338496 (Hielscher et al., Dec. 19, 2013, "Medical Imaging Devices, Methods, and Systems") and 20140088415 (Hielscher et al., Mar. 27, 2014, "Medical Imaging Devices, Methods, and Systems") disclose devices, methods, and systems for generating optical tomographic data including volumetric and surface geometric data.

U.S. patent application publication 20140236003 (Hielscher et al., Aug. 21, 2014, "Interfacing Systems, Devices, and Methods for Optical Imaging") discloses an imaging interface with a plurality of concentric rings for diffuse optical tomography of breast tissue. U.S. patent applications 20140243681 (Hielscher et al., Aug. 28, 2014, "Compact Optical Imaging Devices, Systems, and Methods") and 20190239751 (Hielscher et al., Aug. 8, 2019, "Compact Optical Imaging Devices, Systems, and Methods"), and U.S. patent Ser. No. 10/111,594 (Hielscher et al., Oct. 30, 2018, "Compact Optical Imaging Devices, Systems, and Methods") disclose a handheld optical imaging system with a plurality of detectors. U.S. patent application 20150286785 (Hielscher et al., Oct. 8, 2015, "Systems, Methods, and Devices for Image Reconstruction Using Combined PDE-Constrained and Simplified Spherical Harmonics Algorithm") and U.S. Pat. No. 9,495,516 (Hielscher et al., Nov. 15, 2016, "Systems, Methods, and Devices for Image Reconstruction Using Combined PDE-Constrained and Simplified Spherical Harmonics Algorithm") disclose systems, methods, and devices for image reconstruction using combined PDE-constrained and simplified spherical harmonics (SPN) algorithms. U.S. patent Ser. No. 10/376,150 (Hielscher et al., Aug. 13, 2019, "Interfacing Systems, Devices, and Methods for Optical Imaging") discloses an imaging interface for diffuse optical tomography of breast with a plurality of concentric rings.

U.S. patent application publication 20140236021 (Islam, Aug. 21, 2014, "Near-Infrared Super-Continuum Lasers for Early Detection of Breast and Other Cancers") and U.S. Pat. No. 9,993,159 (Islam, Jun. 12, 2018, "Near-Infrared Super-Continuum Lasers for Early Detection of Breast and Other Cancers") disclose a system and method using near-infrared or short-wave infrared light sources for early detection and monitoring of breast cancer. U.S. patent application publication 20180289264 (Islam, Oct. 11, 2018, "High Signal-to-Noise Ratio Light Spectroscopy of Tissue") discloses a diagnostic system which delivers an optical beam to a nonlinear element that broadens a spectrum of the first optical beam to at least 10 nanometers through a nonlinear effect in the nonlinear element. U.S. patent application 20210038083 (Islam, Feb. 11, 2021, "Multi-Wavelength Wearable Device for Non-Invasive Blood Measurements in Tissue") discloses a system for measuring one or more physiological parameters with a wearable device that includes a light source comprising a driver and semiconductor sources that generate an output optical light.

U.S. patent application publication 20090005692 (Intes et al., Jan. 1, 2009, "Optical Imaging Method for Tissue Characterization") and U.S. Pat. No. 8,565,862 (Intes et al., Oct. 22, 2013, "Optical Imaging Method for Tissue Characterization") disclose a method for detecting and characterizing abnormalities within biological tissue by characterizing optical properties of the tissue. U.S. patent application publication 20180070891 (Jepsen, Mar. 15, 2018, "Imaging With Infrared Imaging Signals") discloses using an infrared imaging signal to image tissue. U.S. patent application publication 20180335753 (Jepsen et al., Nov. 22, 2018, "Co-Located Imaging and Display Pixel") discloses an optical transformation engine coupled between an image pixel and a display pixel. U.S. patent application publication 20190072897 (Jepsen et al., Mar. 7, 2019, "Applications of Diffuse Medium Imaging") discloses methods and an apparatus for imaging translucent materials.

U.S. Pat. No. 9,314,218 (Stearns et al., Apr. 19, 2016, "Integrated Microtomography and Optical Imaging Systems") and U.S. Pat. No. 10,130,318 (Stearns et al., Nov. 20, 2018, "Integrated Microtomography and Optical Imaging Systems") disclose an integrated microtomography and optical imaging system with a rotating table that supports an imaging object, an optical stage, and separate optical and microtomography imaging systems. U.S. Pat. No. 9,770,220 (Stearns et al., Sep. 26, 2017, "Integrated Microtomography and Optical Imaging Systems") discloses a rotating table that supports an imaging object, an optical stage, and separate optical and microtomography imaging systems. U.S. patent application 20170209083 (Zarandi et al., 2017, "Hand-Held Optical Scanner for Real-Time Imaging of Body Composition and Metabolism") and U.S. patent Ser. No. 10/653,346 (Zarandi et al., May 19, 2020, "Hand-Held Optical Scanner for Real-Time Imaging of Body Composition and Metabolism") disclose a handheld system for diffuse optical spectroscopic imaging of human tissue.

U.S. patent application 20060173352 (Lilge et al., 2006, "Optical Transillumination and Reflectance Spectroscopy to Quantify Disease Risk") discloses a method of illuminating tissue of a mammal with light having wavelengths covering a pre-selected spectral range, detecting light transmitted through, or reflected from, the volume of selected tissue, and obtaining a spectrum of the detected light. U.S. patent application 20200116630 (Zhu, 2020, "Compact Guided Diffuse Optical Tomography System for Imaging a Lesion Region") discloses a compact diffuse optical tomography system with laser diodes and a laser diode driver board. U.S. Pat. No. 5,876,339 (Lemire, Mar. 2, 1999, "Apparatus for Optical Breast Imaging") discloses an optical breast imager with an adjustable volume which encloses a patient's breast.

U.S. Pat. No. 5,999,836 (Nelson et al., Dec. 7, 1999, "Enhanced High Resolution Breast Imaging Device and Method Utilizing Non-Ionizing Radiation of Narrow Spectral Bandwidth") and U.S. Pat. No. 6,345,194 (Nelson et al., Feb. 5, 2002, "Enhanced High Resolution Breast Imaging Device and Method Utilizing Non-Ionizing Radiation of Narrow Spectral Bandwidth") disclose breast imaging using collimated non-ionizing radiation in the near ultraviolet, visible, infrared, and microwave regions. U.S. Pat. No. 6,240,309 (Yamashita et al., May 29, 2001, "Optical Measurement Instrument for Living Body"), U.S. Pat. No. 6,640,133 (Yamashita et al., Oct. 28, 2003, "Optical Measurement Instrument for Living Body"), and U.S. Pat. No. 7,142,906 (Yamashita et al., Nov. 28, 2006, "Optical Measurement Instrument for Living Body") disclose an optical measurement instrument which applies visible-infrared light to several positions on a patient.

U.S. patent application 20020045833 (Wake et al., Apr. 18, 2002, "Medical Optical Imaging Scanner Using Multiple Wavelength Simultaneous Data Acquisition for Breast Imaging") discloses a scanner for a medical optical imaging device with an illumination source which directs emitted light into a breast positioned below a support surface. U.S. Pat. No. 6,571,116 (Wake et al., May 27, 2003, "Medical Optical Imaging Scanner Using Multiple Wavelength Simultaneous Data Acquisition for Breast Imaging") and U.S. Pat. No. 6,738,658 (Wake et al., May 18, 2004, "Medical Optical Imaging Scanner Using Multiple Wavelength Simultaneous Data Acquisition for Breast Imaging") disclose a medical optical imaging device with an illumination source that directs emitted light into a breast positioned below a support surface.

U.S. patent application publication 20040092826 (Corbeil et al., May 13, 2004, "Method and Apparatus for Optical Imaging") and U.S. Pat. No. 7,809,422 (Corbeil et al., Oct. 5, 2010, "Method and Apparatus for Optical Imaging") disclose a platform with a cavity into which one of the person's breasts is suspended for optical imaging. U.S. patent application publication 20070287897 (Faris, Dec. 13, 2007, "Optical Vascular Function Imaging System and Method for Detection and Diagnosis of Cancerous Tumors") discloses an in-vivo optical imaging system and method of identifying unusual vasculature associated with tumors. U.S. Pat. No. 8,027,711 (Jones et al., Sep. 27, 2011, "Laser Imaging Apparatus with Variable Patient Positioning") discloses a tabletop to support a patient in front-down position and an opening to permit a breast of the patient to be vertically pendant below the tabletop.

U.S. Pat. No. 8,224,426 (Lilge et al., Jul. 17, 2012, "Optical Transillumination and Reflectance Spectroscopy to Quantify Disease Risk") discloses spectroscopic tissue volume measurements with non-ionizing radiation to detect pre-disease transformations in tissue. U.S. patent application publication 20160066811 (Mohamadi, Mar. 10, 2016, "Handheld and Portable Scanners for Millimeter Wave Mammography and Instant Mammography Imaging") discloses an array of ultra-wide band radio frequency sensors for breast imaging. U.S. Pat. No. 9,513,276 (Tearney et al., Dec. 6, 2016, "Method and Apparatus for Optical Imaging via Spectral Encoding") disclose a method, apparatus and arrangement for obtaining information associated with a sample such as a portion of an anatomical structure. U.S. patent application publication 20170007187 (Breneisen et al., Jan. 12, 2017, "Cancer Detector Using Deep Optical Scanning") discloses Deep Optical Scanning (DEOS) for the detection of breast cancer and the determination of response to therapy.

U.S. Pat. No. 9,597,046 (Goossen et al., Mar. 21, 2017, "Method and Device for Imaging Soft Body Tissue Using X-Ray Projection and Optical Tomography") discloses breast imaging using X-ray projection techniques and optical tomography techniques. U.S. patent application 20170105625 (Eum, Apr. 20, 2017, "Diagnostic Device of Optics Type for Breast") discloses an optical breast diagnostic apparatus with a hemispherical cover. U.S. patent Ser. No. 10/200,655 (Kim et al., Feb. 5, 2019, "Tomographic Imaging Methods, Devices, and Systems") discloses a multispectral bioluminescence optical tomography algorithm makes use of a partial differential equation (PDE) constrained approach. U.S. patent Ser. No. 10/215,636 (Fujii et al., Feb. 26, 2019, "Imaging Device Provided With Light Source That Emits Pulsed Light and Image Sensor") discloses an imaging device with a light source that emits pulsed light at different wavelengths. U.S. patent Ser. No. 10/506,181 (Delgado et al., Dec. 10, 2019, "Device for Optical Imaging") discloses the capture of an infrared image.

Turning to the non-patent literature, Ahmed et al., (2021), "Differential Optical Absorption Spectroscopy-Based Refractive Index Sensor for Cancer Cell Detection," Optical Review, 28, 134-143, discloses a spectroscopic optical sensor for cancerous cell detection in various parts of the human body. Altoe et al., (2019), "Diffuse Optical Tomography of the Breast: A Potential Modifiable Biomarker of Breast Cancer Risk with Neoadjuvant Chemotherapy," Biomedical Optics Express, Aug. 1, 2019, 10(8), 4305-4315, studied whether a diffuse optical tomography breast imaging system (DOTBIS) can provide a comparable optical-based image index of mammographic breast density. Altoe et al., (2021), "Changes in Diffuse Optical Tomography Images During Early Stages of Neoadjuvant Chemotherapy Correlate with Tumor Response in Different Breast Cancer Subtypes", Clinical Cancer Research, Apr. 1, 2021, 27(7), 1949-1957, studied changes in optically derived parameters acquired with a diffuse optical tomography breast imaging system (DOTBIS) in the tumor volume of patients with breast carcinoma receiving neoadjuvant chemotherapy (NAC).

Altoe et al., (2021), "Effects of Neoadjuvant Chemotherapy on the Contralateral Non-Tumor-Bearing Breast Assessed by Diffuse Optical Tomography," Breast Cancer Research, 2021, 23, 16, studied whether changes in optically derived parameters acquired with a diffuse optical tomography breast imager system (DOTBIS) in the contralateral non-tumor-bearing breast in patients administered neoadjuvant chemotherapy (NAC) for breast cancer are associated with pathologic complete response (pCR). Anabestani et al. (2022), "Advances in Flexible Organic Photodetectors: Materials and Applications," Nanomaterials, 2022, 12(21), 3775, discusses recent advances in flexible organic photodetectors, including their applications in health-monitoring, X-ray detection, and imaging. Anderson et al., (2017), "Optical Mammography in Patients with Breast Cancer Undergoing Neoadjuvant Chemotherapy: Individual Clinical Response Index," Academic Radiology, October, 2017, 24(10), 1240-1255, discloses an optical mammography study to develop quantitative measures of pathologic response to neoadjuvant chemotherapy (NAC) in patients with breast cancer.

Angelo et al., (2018), "Review of Structured Light in Diffuse Optical Imaging," Journal of Biomedical Optics, Sep. 14, 2018, 24(7), 071602, discloses diffuse optical imaging probes in living tissue enabling structural, functional, metabolic, and molecular imaging. Applegate et al., (2018), "Multi-Distance Diffuse Optical Spectroscopy with a Single Optode via Hypotrochoidal Scanning," Optics Letters, 2018, 43, 747-750, studied a new method of frequency-domain diffuse optical spectroscopy (FD-DOS) to rapidly acquire a wide range of source-detector (SD) separations by mechanically scanning a single SD pair. Applegate et al. (2020), "Recent Advances in High Speed Diffuse Optical Imaging in Biomedicine," APL Photonics, 2020, 5(4), 040802, 21, reviews recent advances in acquisition and processing speed for several Diffuse Optical Imaging modalities.

Chae et al., (2020), "Development of Digital Breast Tomosynthesis and Diffuse Optical Tomography Fusion Imaging for Breast Cancer Detection," Scientific Reports, 10, 13127 (2020), studied a new digital breast tomosynthesis (DBT)/DOT fusion imaging technique for breast cancer detection. Chitnis et al. (2016), "Towards a Wearable Near Infrared Spectroscopic Probe for Monitoring Concentrations of Multiple Chromophores in Biological Tissue In Vivo," Review of Scientific Instruments, June, 2016, 87(6), 065112, discloses a wearable multi-wavelength technology for functional near-infrared spectroscopy with an 8-wavelength light emitting diode (LED) source. Cinquino et al. (2021), "Light-Emitting Textiles: Device Architectures, Working Principles, and Applications," Micromachines, (Special Issue Emerging and Disruptive Next-Generation Technologies for POC: Sensors, Chemistry and Microfluidics for Diagnostics), 2021, 12(6), 652, discusses applications of light-emitting fabrics, including Organic LEDs.

Cochran et al., (2019), "Hybrid Time-Domain and Continuous-Wave Diffuse Optical Tomography Instrument with Concurrent, Clinical Magnetic Resonance Imaging for Breast Cancer Imaging," Journal of Biomedical Optics, January, 2019, 24(5), 1-11, discusses diffuse optical tomography (DOT) for three-dimensional (3-D) maps of tissue optical and physiological properties in human tissue. Costa et al. (2019), "Flexible Sensors: From Materials to Applications," Technologies (Special Issue, Reviews and Advances in Internet of Things Technologies), 2019, 7(2), 35, reviews the current state of flexible sensor technologies and the impact of material developments on this field. Durduran et al., (2010, 2010), "Diffuse Optics for Tissue Monitoring and Tomography," Reports on Progress in Physics, 2010, 73(7), 076701, discloses using near-infrared or diffuse optical spectroscopy to measure tissue hemodynamics.

Fakayode et al., (2020), "Molecular (Raman, NIR, and FTIR) Spectroscopy and Multivariate Analysis in Consumable Products Analysis," Applied Spectroscopy, reviews, 55:8, 647-723, reviews the use of Raman, near-infrared (NIR), and Fourier-transform infrared (FTIR) spectrometers to evaluate consumable products such as food. Fantini et al., (2001), "Optical Spectroscopy and Imaging of Tissues," NSF Award #0093840, Jun. 1, 2001, studied development of new improved methods and instrumentation for biomedical applications of near-infrared spectroscopy and imaging. Fantini (2005), "Optical Spectroscopy and Imaging of Tissues", NSF Award, 2005 (abstract only viewed), researched techniques for optical spectroscopy and imaging of biological tissues. Fantini et al., (2012), "Near-Infrared Optical Mammography for Breast Cancer Detection with Intrinsic Contrast," Annals of Biomedical Engineering, February, 2012, 40(2), 398-407, reviews optical methods to detect breast cancer on the basis of increased opacity.

Farmani et al., (2020), "Optical Nanosensors for Cancer and Virus Detections," Micro and Nano Technologies, Nanosensors for Smart Cities, Chapter 25, Han et al. editors, Elsevier, 2020, 419-432, ISBN 9780128198704, discusses photonic crystal (PhC)-based optical nanosensors. Feng et al. (2021), "MRI Guided Wearable Near Infrared Spectral Tomography: Simulation Study," Proceedings SPIE, 11639, Optical Tomography and Spectroscopy of Tissue XIV, 116390D, Mar. 5, 2021, discloses a new low-cost imaging system for MRI-guided Near-Infrared Spectral Tomography (MRI-NIRST) for breast cancer detection. Flexman et al., (2008), "The Design and Characterization of a Digital Optical Breast Cancer Imaging System," 30th Annual International Conference of the IEEE Engineering in Medicine and Biology Society, 2008, 3735-3738, discusses how optical imaging has the potential to play a major role in breast cancer screening and diagnosis due to its ability to image cancer characteristics such as angiogenesis and hypoxia.

Ghijsen et al., (2018), "Quantitative Real-Time Optical Imaging of the Tissue Metabolic Rate of Oxygen Consumption," Journal of Biomedical Optics, Mar. 24, 2018, 23(3), 036013, discloses a noncontact method for quantitatively mapping tMRO2 over a wide, scalable field of view. Grosenick et al., (2016), "Review of Optical Breast Imaging and Spectroscopy," Journal of Biomedical Optics, September, 2016, 21(9), 091311, reviews the monitoring neoadjuvant chemotherapy and breast cancer risk assessment via optical breast imaging and spectroscopy. Gunther et al., (2018), "Dynamic Diffuse Optical Tomography for Monitoring Neoadjuvant Chemotherapy in Patients with Breast Cancer," Radiology, June, 2018; 287(3): 778-786, identifies dynamic optical imaging features associated with pathologic response in patients with breast cancer during neoadjuvant chemotherapy.

Hoi et al., (2018), "Non-Contact Dynamic Diffuse Optical Tomography Imaging System for Evaluating Lower Extremity Vasculature," Biomedical Optics Express, 2018, 9, 5597-5614, discloses a multi-view non-contact dynamic diffuse optical tomographic imaging system for the clinical evaluation of vasculature in the lower extremities. Imamura et al., (2018), "In Vivo Optical Imaging of Cancer Cell Function and Tumor Microenvironment," Cancer Science, 2018, 109, 912-918, discusses in vivo optical imaging using fluorescence and bioluminescence. Intes et al. (2004), "Time-Domain Optical Mammography Softscan: Initial Results On Detection and Characterization of Breast Tumors," Proceedings SPIE 5578, Photonics North 2004: Photonic Applications in Astronomy, Biomedicine, Imaging, Materials Processing, and Education, Dec. 9, 2004 presents initial results obtained using a breast-imaging system developed by Advanced Research Technologies comprising a 4-wavelength time-resolved scanning system.

Jeong et al., (2020), "Emerging Advanced Metasurfaces: Alternatives to Conventional Bulk Optical Devices," Microelectronic Engineering, 2020, Vol. 220, 111146, ISSN 0167-9317, discusses the use of optical metasurfaces as color filters, metalenses, beam generators or splitters, and metaholograms. Jiang et al. (2021), "MRI-Guide Near Infrared Spectroscopic Tomographic Imaging System with Wearable Optical Breast Interface for Breast Imaging," Proceedings SPIE, 11639, Optical Tomography and Spectroscopy of Tissue XIV, 116391J, Mar. 5, 2021, discloses a new photodetector (PD) and source fiber based wearable MRI-guide near infrared spectroscopic tomographic imaging (MRg-NIRST) system. Joshi et al., (2018), "Targeted Optical Imaging Agents in Cancer: Focus on Clinical Applications," Contrast Media and Molecular Imaging, Aug. 27, 2018, discusses molecular imaging for in vivo visualization of cancer over time based on biological mechanisms of disease activity.

Jung et al. (2015), "Non-Contact Deep Tissue Imaging using a Hand-Held Near-infrared Optical Scanner," Journal of Medical Diagnostic Methods, Mar. 24, 2015, 4(2), 1-10, discloses fiber-free non-contact near-infrared (NIR) imaging devices using wide-field detectors Khan (2013), "Image Reconstruction in Diffuse Optical Tomography With Sparsity Constraints", NSF Award, 2013 (abstract only viewed), researched the use of sparsity-constrained regularization for solving the diffuse optical tomography inverse problem. Kim et al., (2016), "US-Localized Diffuse Optical Tomography in Breast Cancer: Comparison with Pharmacokinetic Parameters of DCE-MRI and With Pathologic Biomarkers," BMC Cancer, Feb. 1, 2016, 16:50, discloses correlating parameters of ultrasonography-guided diffuse optical tomography with the pharmacokinetic features of dynamic contrast-enhanced MRI and pathologic markers of breast cancer. Koetse et al., (2007), "Optical Sensor Array Platform Based on Polymer Electronic Devices," Proceedings SPIE 6739, Electro-Optical Remote Sensing, Detection, and Photonic Technologies and Their Applications, 67391D, Nov. 7, 2007, discusses devices based on polymer semiconductors fabricated with thin film technology.

Koomson, 2019), "A Noninvasive Biological Research Tool for Measurement of Tissue and Cerebral Oxygenation," NSF Award #1919038, Jul. 15, 2019, (abstract only viewed) investigates compact wearable devices with advanced NIRS capability. Krishnamurthy, 2018), "Using Near-Infrared Spectroscopy to Study Static and Dynamic Hemoglobin Contrast Associated with Breast Cancer," Tufts University, Dissertation, 2018, discloses an instrument for diffuse optical mammography with parallel plate geometry. Leo et al. (2017), "Optical Imaging of the Breast: Basic Principles and Clinical Applications," American Journal of Roentgenology, 2017, 209:1, 230-238, discloses summarizes the physical principles, technology features, and first clinical applications of optical imaging techniques to the breast. Li et al. (2018), "Sensitive and Wearable Optical Microfiber Sensor for Human Health Monitoring," Advanced Materials Technologies, 2018, 3, 1800296, discloses a sensor with a hybrid plasmonic microfiber knot resonator embedded in a polydimethylsiloxane membrane.

Liu et al., (2018), "Diffuse Optical Spectroscopy for Monitoring the Responses of Patients with Breast Cancer to Neoadjuvant Chemotherapy: A Meta-Analysis," Medicine, 2018, 97(41), 12683, investigated the potential of diffuse optical spectroscopy (DOT) for monitoring the responses of patients with breast cancer to neoadjuvant chemotherapy (NAC). Liu et al., (2020), "Recent Progress in Flexible Wearable Sensors for Vital Sign Monitoring," Sensors, 2020, 20(14), 4009, discusses the development of flexible electronic materials, as well as the wide development and application of smartphones, the cloud, and wireless systems, flexible wearable sensor technology. Liu et al., (2021), "Simultaneous Measurements of Tissue Blood Flow and Oxygenation Using a Wearable Fiber-Free Optical Sensor," Journal of Biomedical Optics, Jan. 29, 2021, 26(1), 012705, discusses a wearable dual-wavelength diffuse speckle contrast flow oximetry (DSCFO) device for simultaneous measurements of blood flow and oxygenation variation in deep tissues.

Lutzweiler et al., (2013), "Optoacoustic Imaging and Tomography: Reconstruction Approaches and Outstanding Challenges in Image Performance and Quantification," Sensors, 2013, 13(3), 7345-7384, reviews optoacoustic imaging from image reconstruction and quantification perspectives. Ma et al. (2020b), "Fiber-Free Parallel-Plane Continuous Wave Breast Diffuse Optical Tomography System," SPIE 11229, Advanced Biomedical and Clinical Diagnostic and Surgical Guidance Systems XVIII, Proceedings, 112290L, Feb. 21, 2020 discusses near infrared diffuse optical tomography (DOT) for detecting breast cancer. Mabou et al., (2018), "Breast Cancer Detection Using Infrared Thermal Imaging and a Deep Learning Model," Sensors, 2018, 18(9), 2799, discloses the use of infrared digital imaging for breast cancer detection based on thermal comparison between a healthy breast and a breast with cancer.

Moreno et al. (2019), "Evaluation on Phantoms of the Feasibility of a Smart Bra to Detect Breast Cancer in Young Adults," Sensors, 2019, 19(24), 5491, discloses the use of breast tissue phantoms to investigate the feasibility of quantifying breast density and detecting breast cancer tumors using a smart bra. Nguyen et al., (2020), "Preliminary Development of Optical Computed Tomography (Optical CT) Scanner Using Transillumination Imaging NAD," Conference: International Symposium on Applied Science 2019, Hochiminh City, Vietnam, May 14, 2020, discusses the use of near-infrared transillumination imaging for biomedical applications such as human biometrics and animal experiments. Pan et al., (2020), "A Multifunctional Skin-Like Wearable Optical Sensor Based on an Optical Micro-/Nano-fibre," Nanoscale, 2020, Issue 33, discusses multifunctional skin-like sensors for next-generation healthcare, robotics, and bioelectronics.

Park et al., (2013), "Multispectral Imaging Using Polydimethylsiloxane (PDMS) Embedded Vertical Silicon Nanowires," OSA Technical Digest (online) (Optical Society of America, 2013), paper CTu3O.1, reports on the demonstration of a compact multispectral imaging system that uses vertical silicon nanowires for a filter array. Park et al., (2015), "Vertically Stacked Photodetector Devices Containing Silicon Nanowires with Engineered Absorption Spectra," ACS Photonics, Mar. 16, 2015, 2(4), 544-549, discloses a vertically stacked photodetector device containing silicon nanowire photodetectors formed above a silicon substrate that also contains a photodetector. Perumal et al., (2019), "Near Infra-Red Polymeric Nanoparticle Based Optical Imaging in Cancer Diagnosis," Journal of Photochemistry and Photobiology, Biology, 2019, Vol. 199, 111630, ISSN 1011-1344, reviews the recent progress in NIRF polymeric nanoparticles used for optical imaging particularly on cancer diagnosis.

Pinti et al. (2018), "A Review on the Use of Wearable Functional Near-Infrared Spectroscopy in Naturalistic Environments," Japanese Psychology Research, October 2018, 60(4), 347-373, reviews the use of wearable fNIRS in naturalistic settings in the field of cognitive neuroscience. Qiu (2018), "Implantable Ultra-low Power VO2 MEMS Scanner Based Surface-Enhanced Raman Spectroscope for Wide-field Tumor Imaging in Free Moving Small Animals", NSF Award, 2018 (abstract only viewed), discloses tumor-targeting surface enhanced Raman scattering nanoparticles based on multiplexed Raman spectroscopy. Rahman et al., (2016), "Electromagnetic Performances Analysis of an Ultra-Wideband and Flexible Material Antenna in Microwave Breast Imaging: To Implement a Wearable Medical Bra," Scientific Reports, 2016, Vol. 6, 38906, discloses a compact and ultra-wide band antenna on a flexible substrate for microwave imaging.

Ray et al. (2017), "A Systematic Review of Wearable Systems for Cancer Detection: Current State and Challenges," Journal of Medical Systems, Oct. 2, 2017, 41(11), 180, reviews cancer detection using wearable systems, including sensor-based smart systems with a microcontroller, Bluetooth module, and smart phone. Robbins et al. (2021), "Two-Layer Spatial Frequency Domain Imaging of Compression-Induced Hemodynamic Changes in Breast Tissue," Journal of Biomedical Optics, May 24, 2021, 26(5), 056005, studied hemodynamic changes in response to localized breast compression using a handheld SFDI device. Roblyer et al. (2020b), "Tracking Breast Cancer Therapies with Handheld and Wearable Diffuse Optics," Biophotonics Congress: Biomedical Optics 2020 (Translational, Microscopy, OCT, OTS, BRAIN), OSA Technical Digest (Optical Society of America, 2020), paper TM4B.1 disclose an NIR-II imaging system), "Detection of Optically Luminescent Probes using Hyperspectral and Diffuse Imaging in Near-infrared" (DOLPHIN) for noninvasive real-time tracking of a 0.1 mm-sized fluorophore through the gastrointestinal tract of a mouse.

Saikia et al. (2017), "A Cost-Effective LED and Photodetector Based Fast Direct 3D Diffuse Optical Imaging System," Proc. SPIE 10412, Diffuse Optical Spectroscopy and Imaging VI, Jul. 28, 2017, European Conferences on Biomedical Optics, 2017, Munich, Germany, discloses a cost-effective and high-speed 3D diffuse optical tomography system using high power LED light sources and silicon photodetectors. Saikia et al. (2019), "A Point-of-Care Handheld Region-of-Interest (ROI) 3D Functional Diffuse Optical Tomography (fDOT) System," Proc. SPIE 10874, Optical Tomography and Spectroscopy of Tissue XIII, Mar. 1, 2019, discloses a 3D Functional Diffuse Optical Tomography (fDOT) system based on an Internet-of-things (IoT) concept. Satharasinghe et al. (2018), "Photodiodes Embedded Within Electronic Textiles," Science Reports, 2018, 8, 16205, discloses a novel photodiode-embedded yarn with possible applications including monitoring body vital signs.

Schoustra et al. (2021), "Pendant Breast Immobilization and Positioning in Photoacoustic Tomographic Imaging," Photoacoustics, 2021, 21, 100238 describes the design, development and added value of breast-supporting cups to immobilize and position the pendant breast in photoacoustic tomographic imaging. Shokoufi et al. (2017), "Novel Handheld Diffuse Optical Spectroscopy Probe for Breast Cancer Assessment: Clinical Study," Journal of Biomedical Science, 6(5), 34, discloses a hand-held continuous-wave radiofrequency modulated diffuse optical spectroscopy probe. Soliman et al., (2010), "Functional Imaging Using Diffuse Optical Spectroscopy of Neoadjuvant Chemotherapy Response in Women with Locally Advanced Breast Cancer," Clinical Cancer Research, Apr. 20, 2010, 15, 2605-2614, discloses functional imaging with tomographic near-infrared diffuse optical spectroscopy to measure tissue concentration of deoxyhemoglobin, oxyhemoglobin, percent water, and scattering power.

Spink et al. (2020), "High Optode-Density Wearable Probe for Monitoring Breast Tumor Dynamics During Neoadjuvant Chemotherapy," Biophotonics Congress: Biomedical Optics 2020 (Translational, Microscopy, OCT, OTS, BRAIN), OSA Technical Digest (Optical Society of America, 2020), paper TTu1B.2 disclose an NIR-II imaging system), "Detection of Optically Luminescent Probes using Hyperspectral and diffuse Imaging in Near-infrared" (DOLPHIN). Spink et al. (2021), "High Optode-Density Wearable Diffuse Optical Probe for Monitoring Paced Breathing Hemodynamics in Breast Tissue," Journal of Biomedical Optics, Jun. 2, 2021, 26(6), 062708, discloses a high optode-density wearable continuous wave diffuse optical probe for the monitoring of breathing hemodynamics in breast tissue. Tank et al. (2020), "Diffuse Optical Spectroscopic Imaging Reveals Distinct Early Breast Tumor Hemodynamic Responses to Metronomic and Maximum Tolerated Dose Regimens," Breast Cancer Research, 2020, 22, 29 reports on a dual-center study which examined 54 breast tumors receiving NAC measured with DOSI before therapy and the first week following chemotherapy administration.

Teng (2018), "A Wearable Near-Infrared Diffuse Optical System for Monitoring in Vivo Breast Tumor Hemodynamics During Chemotherapy Infusions," Boston University, Dissertation, 2018, discloses a new wearable diffuse optical device to investigate if very early timepoints during a patient's first chemotherapy infusion are predictive of overall response (pCR versus non-pCR) to NAC. Teng et al. (2017), "Wearable Near-Infrared Optical Probe for Continuous Monitoring During Breast Cancer Neoadjuvant Chemotherapy Infusions," Journal of Biomedical Optics, 22(1), 14001 presents a new continuous-wave wearable diffuse optical probe for investigating the hemodynamic response of locally advanced breast cancer patients during neoadjuvant chemotherapy infusions. Tiwari et al. (2022), "Role of Sensor Technology in Detection of the Breast Cancer," BioNanoScience, 2022, 12, 639-659, reviews different sensors developed to detect breast cancer over the past few years.

Tromberg et al., (2016), "ACRIN 6691 Investigators. Predicting Responses to Neoadjuvant Chemotherapy in Breast Cancer," Cancer Research, Aug. 15, 2016, 76(20), 5933-5944, investigates whether changes from baseline to mid-therapy in a diffuse optical spectroscopic imaging (DOSI)-derived imaging endpoint, the tissue optical index, predict pathologic complete response in women undergoing breast cancer neoadjuvant chemotherapy. Uddin et al., (2020a), "Optimal Breast Cancer Diagnostic Strategy Using Combined Ultrasound and Diffuse Optical Tomography," Biomedical Optics Express, 11(5), 2722-2737, presents a two-stage diagnostic strategy that is both computationally efficient and accurate. Upputuri, (2019), "Photoacoustic Imaging in the Second Near-Infrared Window: A Review," Journal of Biomedical Optics, Apr. 9, 2019, 24(4), 040901, discusses photoacoustic (PA) imaging that combines optical excitation and ultrasound detection.

Vavadi et al., (2018), "Compact Ultrasound-Guided Diffuse Optical Tomography System for Breast Cancer Imaging," Journal of Biomedical Optics, 2018, 24(2), 1-9, discusses an ultrasound-guided DOT system. Wang et al. (2020), "Development of a Prototype of a Wearable Flexible Electro-Optical Imaging System for the Breast," Biophotonics Congress: Biomedical Optics 2020 (Translational, Microscopy, OCT, OTS, BRAIN), OSA Technical Digest (Optical Society of America, 2020), paper TM4B.4, discloses a wearable breast imaging system which combines a garment and a flexible electronic system. Yu et al. (2010), "Near-Infrared, Broad-Band Spectral Imaging of the Human Breast for Quantitative Oximetry: Applications to Healthy and Cancerous Breasts," Journal of Innovative Optical Health Sciences, October 2010, 03(4):267-277 discusses the examination of ten human subjects with a previously developed instrument for near-infrared diffuse spectral imaging of the female breast.

Yuan et al. (2014), "Light-Emitting Diode-Based Multiwavelength Diffuse Optical Tomography System Guided by Ultrasound," Journal of Biomedical Optics, Dec. 4, 2014, 19(12) 126003, discloses a low-cost DOT system using LEDs of four wavelengths in the NIR spectrum as light sources. Zhang et al., (2020), "Efficacy of Shear-Wave Elastography Versus Dynamic Optical Breast Imaging for Predicting the Pathological Response to Neoadjuvant Chemotherapy in Breast Cancer," European Journal of Radiology, 2020, 129, 109098, discusses the value of shear-wave elastography (SWE) parameters and dynamic optical breast imaging features for predicting pathological responses to neoadjuvant chemotherapy (NACT) in breast cancer (BC). Zhao et al. (2021), "High Resolution, Deep Imaging Using Confocal Time-of-Flight Diffuse Optical Tomography," IEEE Transactions on Pattern Analysis and Machine Intelligence, Jul. 1, 2021, 43(7), 2206-2219, discloses how time-of-flight diffuse optical tomography (ToF-DOT) can achieve millimeter spatial resolution in the highly scattered diffusion regime. Zhao et al. (2022), "MRI-Guided Near-Infrared Spectroscopic Tomography (MRg-NIRST): System Development for Wearable, Simultaneous NIRS and MRI Imaging," Proc. SPIE 11952, Multimodal Biomedical Imaging XVII, Mar. 2, 2022, discloses a novel wearable MRg-NIRST system for breast cancer detection with eight flex circuit strips, each with six photodetectors (PDs) and six source fibers.

Zhu et al. (2020), "A Review of Optical Breast Imaging: Multi-Modality Systems for Breast Cancer Diagnosis," European Journal of Radiology, August 2020, 129:109067, reviews optical breast imaging using multi-modality platforms. Zhu et al., (2021), "Early Assessment Window for Predicting Breast Cancer Neoadjuvant Therapy Using Biomarkers, Ultrasound, and Diffuse Optical Tomography," Breast Cancer Research and Treatment, 2021, assesses the utility of tumor biomarkers, ultrasound (US) and US-guided diffuse optical tomography (DOT) in early prediction of breast cancer response to neoadjuvant therapy (NAT).

SUMMARY OF THE INVENTION

This invention is a wearable device or system for optical analysis of breast tissue which can help in early detection and analysis of abnormal tissue. In an example, this invention can be embodied in a "smart bra." In another example, this invention can be inserted into the cup of a conventional bra. This device or system can have advantages over current screening methods such as conventional mammography because it involves less exposure to potentially-harmful ionizing radiation. It can also enable easier ambulatory longitudinal tracking of tissue changes over time. This device has light emitters which transmit light into breast tissue and light receivers which receive the light after it has been transmitted through the breast tissue. It also has expandable chambers which gently compress a breast to reduce light diffusion and improve optical scanning of breast tissue.

In an example, this wearable device or system for analyzing breast tissue can include: a cup which is worn on a person's breast; a first expandable chamber in a first portion of the cup, wherein the first portion is on a first side of an anterior-to-posterior virtual plane intersecting the cup; a second expandable chamber in a second portion of the cup, wherein the second portion is on a second side of the virtual plane; a plurality of light emitters in the first portion of the cup; and a plurality of light receivers in the second portion of the cup. A portion of the breast which is between the plurality of light emitters and the plurality of light receivers is compressed for optical scanning. Light from light emitters is received by light receivers after the light has passed through the breast and is used to analyze breast tissue.

INTRODUCTION TO THE FIGURES

DETAILED DESCRIPTION OF THE FIGURES

Figure 1:
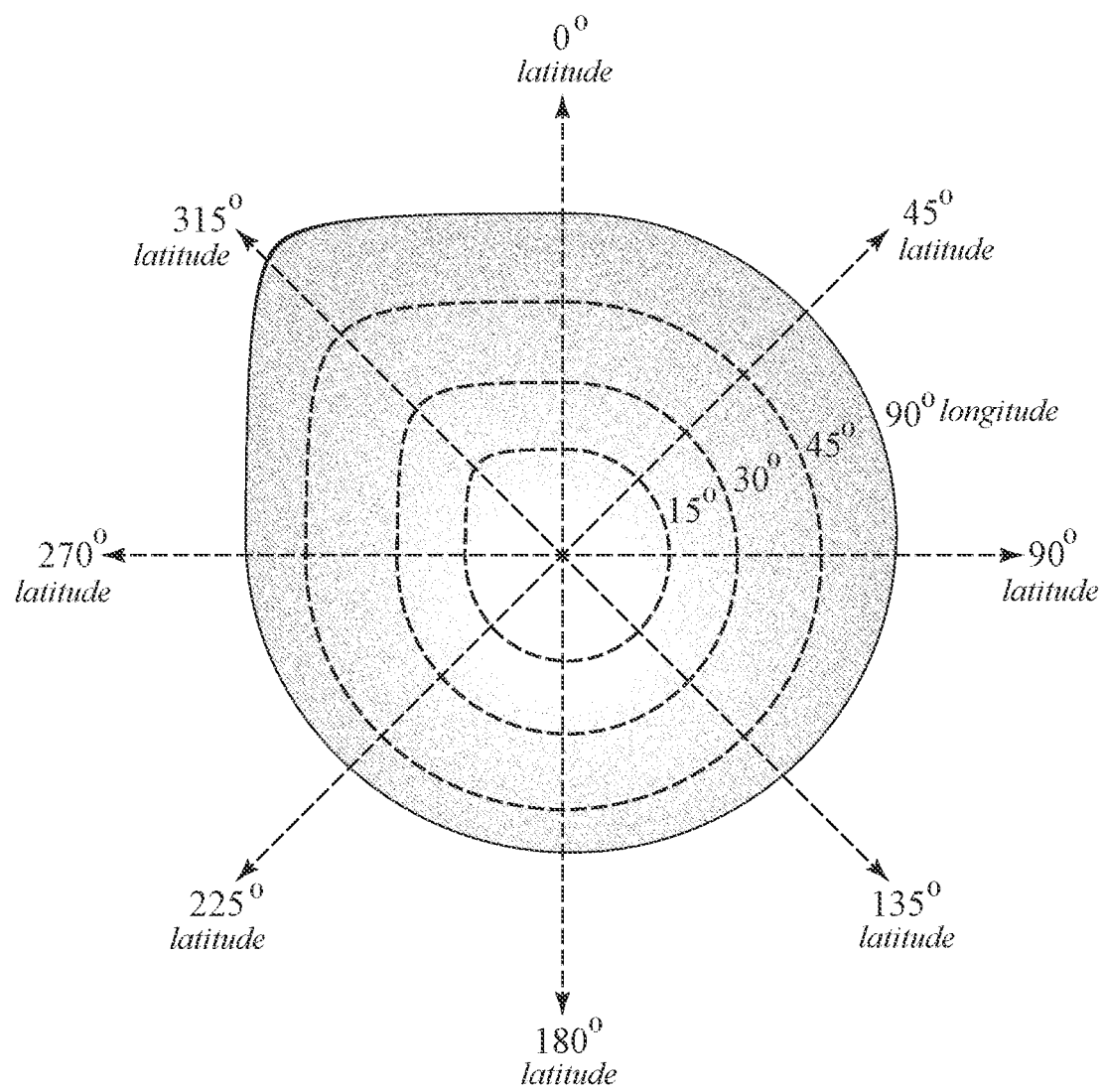
FIG. 1 shows a latitudinal and longitudinal grid on a bra cup which can be used to specify component locations.

FIGS. 2 through 3 and FIGS. 5 through 19 show examples of how a wearable device for analyzing breast tissue can comprise: a cup which is configured to be worn on a person's breast; a first expandable chamber in a first portion of the cup, wherein the first portion is on a first side of an anterior-to-posterior virtual plane intersecting the cup; a second expandable chamber in a second portion of the cup, wherein the second portion is on a second side of the anterior-to-posterior virtual plane intersecting the cup; a plurality of light emitters in the first portion of the cup; and a plurality of light receivers in the second portion of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

In an example, the plane can be parallel to 0-degree and 180-degree latitudinal lines of the cup. In an example, the first portion of the cup can be to the right of the plane and the second portion of the cup can be to the left of the plane. In an example, the first portion of the cup can be to the left of the plane and the second portion of the cup can be to the right of the plane. In an example, the plane can be parallel to 270-degree and 90-degree latitudinal lines of the cup. In an example, the first portion of the cup can be below the plane and the second portion of the cup can be above the plane. In an example, the first portion of the cup can be above the plane and the second portion of the cup can be below the plane.

In an example, the plane can be parallel to 315-degree and 135-degree latitudinal lines of the cup. In an example, the first portion of the cup can be to the lower left of the plane and the second portion of the cup can be to the upper right of the plane. In an example, the first portion of the cup can be to the upper right of the plane and the second portion of the cup can be to the lower left of the plane. In an example, the plane can be parallel to 225-degree and 45-degree latitudinal lines of the cup. In an example, the first portion of the cup can be to the lower right of the plane and the second portion of the cup can be to the upper left of the plane. In an example, the first portion of the cup can be to the upper left of the plane and the second portion of the cup can be to the lower right of the plane.

In an example, the plurality of light emitters are no closer than ¼ inch from the plane and the plurality of light receivers are no closer than ¼ inch from the plane. In an example, the plurality of light emitters are no closer than ½ inch from the plane and the plurality of light receivers are no closer than ½ inch from the plane. In an example, the plurality of light emitters are no closer than 1 inch from the plane and the plurality of light receivers are no closer than 1 inch from the plane.

In an example, the first expandable chamber and the second expandable chamber can be expanded by being filled with a gas. In an example, the first expandable chamber and the second expandable chamber can be expanded by being filled with a liquid. In an example, the wearable device can be a bra. In an example, the wearable device can be inserted into a bra cup.

In an example, a wearable device for analyzing breast tissue can comprise: a cup which is configured to be worn on a person's breast; a first expandable chamber in a first half of the cup, wherein the first half is on a first side of an anterior-to-posterior virtual plane intersecting the cup; a second expandable chamber in a second half of the cup, wherein the second half is on a second side of the anterior-to-posterior virtual plane intersecting the cup; a plurality of light emitters in the first half of the cup; and a plurality of light receivers in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

FIG. 1 shows a coronal (e.g. frontal) view of a latitudinal and longitudinal grid on a breast and/or cup which can be useful for specifying the locations of expandable chambers, light emitters, and light receivers which are part of this device. The breast or cup shown in FIG. 1 is breast or cup on a person's right side, from the person's perspective. It would be on the left from the perspective of person in front of the person. A similar, but symmetric, grid can be defined for a person's left breast or cup, wherein symmetric means reflected across the person's central vertical anterior-to-posterior plane.

As shown in FIG. 1, the polar center of this grid is located on the central apex of the breast or cup. The central apex is the point on the breast or cup which is farthest from the chest wall. The 90-degree longitudinal perimeter line (e.g. ring), which need not be circular, is located where the breast or cup meets the chest wall. The 45-degree longitudinal perimeter line (e.g. ring), which need not be circular, is halfway (along the surface of the breast or cup) between the apex and the 90-degree longitudinal perimeter line. Other longitudinal perimeter lines can be filled in between these perimeter lines and the apex.

In the coronal (e.g. frontal) perspective shown in FIG. 1, the 0-degree latitudinal line (e.g. spoke) points upward from the central apex when the person is standing vertically. The 180-degree latitudinal radial line points downward from the central apex when the person is standing vertically. From a full three-dimensional perspective, the 0-degree latitude can be embodied as a two-dimensional, anterior-to-posterior, virtual plane which intersects the central apex and points directly upward through the 0-latitude point when the person is standing vertically. From a full three-dimensional perspective, the 180-degree latitude can be embodied as a two-dimensional, anterior-to-posterior, virtual plane which intersects the central apex and points directly downward through the 180-latitude point when the person is standing vertically. The 270-degree latitudinal radial line points to the left (in this third-party frontal view, not from the person's perspective) from the central apex. The 90-degree latitudinal radial line points to the right (in this third-party frontal view, not from the person's perspective) from the central apex. Other latitudinal radial lines can be filled in between these radial lines.

In an example, this device can be integrated into a bra. Such a bra can be called a "smart bra" due to the incorporation of sensors and electronic components. In an example, a cup of this device can be an integral part of a smart bra. In an example, this device can be a smart bra with a right-side cup and a left-side cup, each having optical sensors. In an example, this device can be a smart bra with a right-side cup and a left-side cup, each having light emitters and light detectors. In an example, right-side and left-side cups can be integral parts of a bra. In an example, expandable chambers, light emitters, and light receivers can be located within the concavity of a cup in a smart bra. In an example, other components such as a power source, data processor, data transmitter/receiver, and pump can be located within the posterior portion (e.g. back strap) of the bra.

In an example, a wearable device for breast tissue imaging and/or identifying abnormal tissue in a breast can be embodied in a wearable garment (e.g. "smart bra") with a plurality of light emitters and light receivers. Near-infrared light from light emitters can be directed into breast tissue and light receivers can receive the light after it has been transmitted through the tissue. Changes in the intensity and/or spectrum of the light caused by its transmission through the tissue can be analyzed to create an image of the breast tissue and/or identify abnormal tissue in the breast. Since breast tissue scatters light in the infrared range, data from a plurality of light emitters and light receivers is needed to more accurately create an image and/or locate areas of abnormal tissue.

In an example, this device can be embodied in smart bras of different sizes which correspond to conventional bra sizes. The appropriate size smart bra can be selected for a particular person. In an example, this device can be embodied in smart bras of different sizes which correspond to conventional bra sizes when the device is in a first (non-compressive) configuration. In an example, the size of the interior concavity of a smart bra cup can correspond to the cup size of a conventional bra, but the exterior size of the smart bra cup can be larger due to space occupied by expandable chambers, light emitters, and light receivers.

In another example, this device can comprise one or more flexible cup inserts which can be removably attached to (or inserted into) the cup(s) of a conventional bra. In an example, this device can be separate from a bra. In an example, this device can be a bra insert. In an example, this device can be inserted into the concavity of a conventional bra cup. In an example, this device can be inserted between the cup of a conventional bra and a person's breast. In an example, this device can be inserted into a right-side cup of a bra in a first orientation and inserted into a left-side cup of a bra in a second (e.g. reflected) orientation. In an example, this device can be a system comprising a fabric bra with one or more pockets into which expandable chambers, light emitters, and/or light receivers can be removably inserted.

In an example, optical components can be removably-attached to a smart bra by a clip, clasp, or hook-and-eye material so that they can be removed before the bra is washed. In an example, there can be an opaque layer between optical components and an exterior surface of a cup to isolate light receivers from ambient light and to prevent light from light emitters from shining out of the cup. In an example, there can be a waterproof transparent layer between optical components and the interior surface of a cup to protect the optical components from moisture. In an example, an electronics housing and/or an array of light emitters and receivers can be detached from a garment before washing and then reattached after washing.

In an example, optical components can be on the interior surface of a cup. In an example, optical components can be in direct optical communication with the surface of a person's breast. Alternatively, optical components can be separated from the surface of a breast by a transparent layer which transmits light, but protects the optical components when a smart bra is washed. In an example, a transparent layer can be made with a transparent elastomeric material. In an example, a transparent layer can be made with a transparent silicone-based material, such as polydimethylsiloxane (PDMS).

In an example, a smart bra can be worn periodically (e.g. monthly or weekly) in order to obtain a periodic longitudinal time series of optical scans of breast tissue. In an example, a smart bra can be worn for a short period of time on a periodic (e.g. annual, monthly, weekly, or daily) basis in order to obtain a periodic longitudinal time series of optical of breast tissue for identification of possible changes in tissue composition. In an example, data from light receivers in a smart bra can be transmitted to a separate data processor for spectroscopic analysis to identify changes (e.g. trends) in breast tissue composition and configuration to help identify abnormal breast tissue.

In an example, results from optical scanning of right and left breasts can be compared and/or contrasted to each other to help detect abnormal breast tissue. In an example, potential changes in tissue composition over time can be identified which could indicate abnormal tissue growth. In an example, results from more recent scans can be compared and/or contrasted with earlier scans to help detect growth of abnormal breast tissue. In an example, a separate data processor can be in a wearable device (e.g. a smart watch), a mobile device (e.g. a cell phone), or a remote server (e.g. in a healthcare provider's server and/or cloud storage).

In an example, this device can be embodied in a wire support bra, wherein generally elastic fabric cups are reinforced by wires so that the expandable chambers expand predominantly inward toward the center of the bra rather than expanding the cup outward. In an example, this device can be embodied in a wire support bra, wherein generally elastic fabric cups are reinforced by wires so that two expandable chambers expand predominantly toward each other rather than expanding the cup outward. In an example, this device can be embodied in a bra wherein peripheral portions of cups are reinforced by wires and central portions of the cups are not. This causes expansion of the expandable chambers to press inward on the base of a breast, but also allows the breast to expand outward toward the center of the cup into a more-flattened shape. In an example, this device can be embodied in a bra wherein peripheral portions of cups on each side of a cup are reinforced by wires and central portions of the cups are not. This causes expansion of the expandable chambers to press inward on the base of a breast, but also allows the breast to expand into a more-flattened shape.

In an example, a cup can be made from an elastic, flexible, and/or stretchable fabric and/or textile. In an example, a cup can be generally elastic, flexible, and/or stretchable, but also include resilient components in selected locations. In an example, a central portion of a cup can be more elastic (e.g. lower Young's modulus) than peripheral portions of the cup. In an example, portions of the 90-degree longitudinal perimeter of a cup can be reinforced with metal wires and/or rigid polymer components. In an example, perimeter portions of the cup can be less elastic (e.g. higher Young's modulus) in order to provide greater compressive force from the expandable chambers on the breast, but central portions of the cup can be more elastic (e.g. lower Young's modulus) in order to allow the breast to expand outward when compressed laterally. In an example, perimeter portions of a cup can be more rigid in order to provide greater compressive force from the expandable chambers on the breast, but central portions of the cup can be less rigid in order to allow the breast to expand outward when flattened.

In an example, a generally soft and elastic cup can be reinforced by metal wires or resilient polymer strands along peripheral portions between the 90-degree ring and the 35-degree longitudinal ring on the lower and upper halves of the cup. In an example, a generally soft and elastic cup can be reinforced by metal wires or resilient polymer strands along portions of the 90-degree longitudinal perimeter on opposite (axial) quadrants of the cup. In an example, a generally soft and elastic cup can be reinforced by metal wires or resilient polymer strands along peripheral portions between the 90-degree ring and the 35-degree longitudinal ring.

In an example, portions of a cup along the 90-degree longitudinal perimeter can be less elastic (e.g. higher Young's modulus) in order to provide greater compressive force from the expandable chambers on the breast, but portions of the cup along the inner (e.g. less than 30-degree) longitudinal perimeters can be more elastic (e.g. lower Young's modulus) in order to allow the breast to expand outward when flattened. In an example, portions of the cup along the 90-degree longitudinal perimeter can be more rigid in order to provide greater compressive force from the expandable chambers on the breast, but portions of the cup along the inner (e.g. less than 30-degree) longitudinal perimeters can be less rigid in order to allow the breast to expand outward when flattened. In an example, the 15-degree longitudinal perimeter can be more elastic (e.g. lower Young's modulus) than the 45-degree longitudinal perimeter of a cup.

In an example, a generally soft and elastic cup can be reinforced by metal wires or resilient polymer strands along peripheral portions between the 90-degree ring and the 45-degree longitudinal ring on opposite (axial) quadrants of the cup. In an example, a generally soft and elastic cup can be reinforced by metal wires or resilient polymer strands along peripheral portions between the 90-degree ring and the 35-degree longitudinal ring on opposite (axial) quadrants of the cup. In an example, a generally soft and elastic cup can be reinforced by metal wires or resilient polymer strands along portions of the 90-degree longitudinal perimeter on the lower and upper halves of the cup.

In an example, the average elasticity level of the perimeter of the cup along the 90-degree longitudinal line between 0-degrees latitude and 90-degrees latitude can be less than the average elasticity level of the perimeter of the cup along the 90-degree longitudinal line between 90-degrees latitude and 180-degrees latitude. In an example, the average elasticity level of the perimeter of the cup along the 90-degree longitudinal line between 180-degrees latitude and 270-degrees latitude can be less than the average elasticity level of the perimeter of the cup along the 90-degree longitudinal line between 270-degrees latitude and 0-degrees latitude. In an example, portions of the cup along the 315-degree and 135-degree radial lines can be more elastic (e.g. lower Young's modulus) than portions of the cup along the 225-degree and 45-degree radial lines. In an example, portions of the cup along the 225-degree and 45-degree radial lines can be less elastic (e.g. higher Young's modulus) than portions of the cup along the 315-degree and 135-degree radial lines.

In an example, a generally soft and elastic cup can be reinforced by metal wires or resilient polymer strands along peripheral portions between the 90-degree ring and the 45-degree longitudinal ring on the lower and upper halves of the cup. In an example, a generally soft and elastic cup can be reinforced by metal wires or resilient polymer strands along portions of the 90-degree longitudinal perimeter. In an example, a generally soft and elastic cup can be reinforced by metal wires or resilient polymer strands along portions of the 90-degree longitudinal perimeter on the right and left sides of the cup.

In an example, the structure of a fabric cup can include a nested array of elastic rings (e.g. elastic yarns, strands, bands, or strips) which generally align with the longitudinal rings shown FIG. 1. In an example, the structure of a fabric cup can include a nested array of elastic rings (e.g. elastic yarns, strands, bands, or strips) which generally align with the longitudinal rings shown FIG. 1, wherein rings closer to the apex are more elastic than rings farther from the apex. In an example, the structure of a fabric cup can include an array of elastic radial spokes (e.g. elastic yarns, strands, bands, or strips) which generally align with the latitudinal radial lines shown FIG. 1. In an example, the structure of a fabric cup can include an array of elastic radial spokes (e.g. elastic yarns, strands, bands, or strips) which generally align with the latitudinal radial lines shown FIG. 1, wherein spokes closer to the 315-degree-to-135-degree axis are more elastic than rings farther from that axis for a right-side cup.

In an example, a generally soft and elastic cup can be reinforced by metal wires or resilient polymer strands along peripheral portions between the 90-degree ring and the 35-degree longitudinal ring on the right and left sides of the cup. In an example, a generally soft and elastic cup can be reinforced by metal wires or resilient polymer strands along peripheral portions between the 90-degree ring and the 45-degree longitudinal ring. In an example, a generally soft and elastic cup can be reinforced by metal wires or resilient polymer strands along peripheral portions between the 90-degree ring and the 45-degree longitudinal ring on the right and left sides of the cup.

In an example, a cup can be concave. In an example, a right-side cup (from the person's perspective) can have a generally oblate hemispherical shape, being elongated (e.g. having an extension or bulge) along the 315-degree latitudinal line. This elongation, extension, or bulge is designed to better detect abnormal tissue in the upper-left quadrant of the right breast nearest to the arm due to the higher prevalence of abnormal tissue in this area. In an example, a right-side cup can have a tear-drop shaped perimeter, with the spike of the tear-drop shape generally along the 315-degree latitudinal line. In an example, the 90-degree longitudinal perimeter line of a right-side cup can have a tear-drop shape, with the spike of the tear-drop shape generally along the 315-degree latitudinal line.

In an example, a symmetric cup can be designed for the left-side breast when this device is embodied in a complete bra with right-side and left-side cups. In an example, a cup can be rotated or otherwise reoriented for use in the opposite side of a bra when this device is embodied in a bra insert. In an example, a left-side cup (from the person's perspective) can have a generally oblate hemispherical shape, being elongated (e.g. having an extension or bulge) along the 45-degree latitudinal line. This elongation, extension, or bulge is designed to better detect abnormal tissue in the upper-left quadrant of the left breast nearest to the arm due to the higher prevalence of abnormal tissue in this area. In an example, a left-side cup can have a tear-drop shaped perimeter, with the spike of the tear-drop shape generally along the 45-degree latitudinal line. In an example, the 90-degree longitudinal perimeter line of a right-side cup can have a tear-drop shape, with the spike of the tear-drop shape generally along the 45-degree latitudinal line.

In an example, a cup can have mildly-adhesive components on its interior. In an example, a cup can be embodied in a flexible concave bandage, sticker, or patch. Mild adhesion can help to keep the cup in the same position relative to breast tissue during an examination, even during respiratory movement. In an example, a cup can further comprise an array of small-scale suction cups on its interior. These small-scale suction cups can help to keep the cup in the same position relative to breast tissue during an examination, even during respiratory movement.

In an example, this device can comprise two expandable chambers. In an example, an expandable chamber can be expanded by (partially) filling it with a gas (such as air), a liquid (such as water), or a gel. In an example, an expandable chamber can be expanded by being filled with a gas, liquid, or gel. In an example, an expandable chamber can be expanded by pumping air into it. In an example, the device can further comprise an air or liquid pump which is integrated into a bra or is separate and connected to a bra via one or more tubes. In an example, the device can further comprise a data processor which controls the operation of an air or liquid pump. In an example, an expandable chamber can be expanded by a pneumatic mechanism. In an example, an expandable chamber can be expanded by pumping water into it. In an example, an expandable chamber can be expanded by a hydraulic mechanism.

In an example, a cup can have three layers: an interior layer which is closest to the surface of a breast; an exterior layer on the outside of the cup (and farthest from the surface of the breast); and a middle layer between the interior layer and the outer layer. In an example, light emitters and light receivers can be embedded in or attached to the inner surface of the interior layer. In an example, the inner layer can be transparent. In an example, expandable chambers can be in the middle layer. In an example, the outer layer can be made from an elastic and/or stretchable fabric or textile.

In an example, the interior layer of a cup can be the most elastic, the most transparent, and the thinnest layer of the cup. In an example, the interior layer can be made with polydimethylsiloxane (PDMS) or another silicone-based polymer. In an example, an inner layer can comprise an acrylic elastomer. In an example, an inner layer can comprise polyethylene terephthalate (PET). In an example, the interior layer can be between 0.5 mm and 2 mm thick. In an example, the middle layer of the cup can be the thickest layer of the cup. In an example, the interior layer can be between 2 mm and 8 mm thick. In an example, the exterior layer of the cup can be the least elastic and most opaque layer of the cup. In an example, the exterior layer can be between 1 mm and 5 mm thick.

In an example, this device can comprise two expandable chambers, one on either side of a cup. In an example, an expandable chamber can be expanded by filling it with a gas, liquid, or gel. In an example, an expandable chamber can be expanded by pumping air into it. In an example, the device can further comprise an air or liquid pump which is integrated into a bra or is separate and connected to a bra via one or more tubes. In an example, the device can further comprise a data processor which controls the operation of an air or liquid pump. In an example, an expandable chamber can be expanded by a pneumatic mechanism. In an example, an expandable chamber can be expanded by pumping water into it. In an example, an expandable chamber can be expanded by a hydraulic mechanism.

In an example, expansion of first and second expandable chambers can be selectively and individually controlled. In an example, a first expandable chamber can be expanded before the second expandable chamber is expanded. In an example, a first expandable chamber can both be expanded, but by different amounts. In an example, the device can further comprise one or more pressure sensors. In an example, there can be a pressure sensor in fluid communication with an expansion chamber. In an example, expansion of one or both chambers can be adjusted based on internal pressure in one or both chambers. In an example, there can be a pressure sensor between an expansion chamber and the surface of a breast. In an example, expansion of one or both chambers can be adjusted based on pressure between the device and breast tissue.

In an example, a first expandable chamber can be expanded by a greater percentage than a second expandable chamber. In an example, an expandable chamber can have a first non-expanded size and a second expanded size, wherein the second size is at least 25% greater than the first size. In an example, an expandable chamber can have a first non-expanded size and a second expanded size, wherein the second size is at least 50% greater than the first size. In an example, an expandable chamber can have a first non-expanded size and a second expanded size, wherein the second size is at between 40% and 90% greater than the first size. In an example, an expandable chamber can have a first non-expanded size and a second expanded size, wherein the second size is at least twice the first size.

In an example, an expandable chamber can be a balloon. In an example, an expandable chamber can be a chamber with a flexible surface which is impermeable to air. In an example, an expandable chamber can be an air-tight compartment or pocket. In an example, an expandable chamber can be attached to the interior of a cup. In an example, an expandable chamber can be inserted into a pocket in a cap. In an example, an expandable chamber can be inside the concavity of a cup. In an example, an expandable chamber can be within a layer of a cup. In an example, an expandable chamber can have a crescent or banana shape. In an example, an expandable chamber can have a keystone or trapezoidal shape. In an example, an expandable chamber can have a toroidal or doughnut shape.

In an example, an expandable chamber can be a balloon, bladder, or compartment. In an example, an expandable chamber can be a balloon, bladder, or compartment which contains a liquid (e.g. water). In an example, an expandable chamber can be a balloon, bladder, or compartment which contains a gas (e.g. air). In an example, an expandable chamber can be a bladder which is expanded by being filled with a gas or liquid and a smart bra can have a plurality of tubes or channels through which the gas or liquid is delivered into expandable chambers. In an example, each expandable chamber can be in fluid communication with a fluid pump through a separate fluid tube or channel between the fluid pump and the expandable chamber. In an example, some or all of the expandable chambers can be connected to a fluid pump by a common fluid tube or channel, but still be expanded differentially due to different size gaps between their respective optical components and the surface of a breast. In an example, there can be different tubes or channels for different expandable chambers so that a selected subset of expandable chambers can be expanded.

In an example, an expandable chamber can have a disk shape in a first configuration and an ellipsoidal shape in an expanded second configuration. In an example, an expandable chamber can have a disk shape in a first configuration and a cylindrical shape in an expanded second configuration. In an example, an expandable chamber can have a pleated and/or folded shape, like an accordion or bellows. In an example, an expandable chamber can have a pleated configuration, like an accordion or bellows. In an example, an expandable chamber can have a shape which is selected from the group consisting of: pancake, disk, ellipsoidal, oblong, oval, toroidal, hemispherical, and spherical. In an example, an expandable chamber can be flexibly attached to an optical component. In an example, an expandable chamber can be located between an optical component and an exterior layer of a cup on a smart bra. In an example, an expandable chamber can be substantially parallel to an optical component.

In an example, an expandable chamber can have an arcuate shape. In an example, an expandable chamber can be shaped like a section of a circle, ring, or torus. In an example, an expandable chamber can be shaped like a half of a circle, ring, or torus. In an example, an expandable chamber can be shaped like a quarter of a circle, ring, or torus. In an example, there can be a plurality of expandable chambers on each side of a virtual plane through a cup. In an example, expandable chambers on the same side of a virtual plane can be nested and/or concentric.

In an example, an expandable chamber can follow a portion of the perimeter of a cup. In an example, an expandable chamber can follow (e.g. span along) a portion of the 90-degree longitudinal ring. In an example, a first expandable chamber can follow (e.g. span along) between one quarter and one half of the 90-degree longitudinal ring on one side of a cup and a second expandable chamber can follow (e.g. span along) between one quarter and one half of the 90-degree longitudinal ring on the opposite side of the cup.

In an example, a first expandable chamber can be within a first portion of a cup clockwise between the 225-degree and 315-degree latitudinal spokes and between the 30-degree and 90-degree longitudinal rings. In an example, a second expandable chamber can be within a second portion of a cup clockwise between the 45-degree and 135-degree latitudinal spokes and between the 30-degree and 90-degree longitudinal rings. In an example, a first expandable chamber can be within a first portion of a cup clockwise between the 135-degree and 225-degree latitudinal spokes and between the 30-degree and 90-degree longitudinal rings. In an example, a second expandable chamber can be within a second portion of a cup clockwise between the 315-degree and 45-degree latitudinal spokes and between the 30-degree and 90-degree longitudinal rings.

In an example, a first expandable chamber can be within a first portion of a cup clockwise between the 0-degree and 90-degree latitudinal spokes and between the 30-degree and 90-degree longitudinal rings. In an example, a second expandable chamber can be within a second portion of a cup clockwise between the 180-degree and 270-degree latitudinal spokes and between the 30-degree and 90-degree longitudinal rings. In an example, a first expandable chamber can be within a first portion of a cup between the 45-degree and 90-degree longitudinal rings. In an example, a second expandable chamber can be within a second portion of a cup clockwise between the 30-degree and 45-degree longitudinal rings. In an example, a second expandable chamber can be within a second portion of a cup clockwise between the 15-degree and 45-degree longitudinal rings.

In an example, a first expandable chamber can be within a first portion of a cup clockwise between the 225-degree and 315-degree latitudinal spokes. In an example, a second expandable chamber can be within a second portion of a cup clockwise between the 45-degree and 135-degree latitudinal spokes. In an example, a first expandable chamber can be within a first portion of a cup clockwise between the 135-degree and 225-degree latitudinal spokes. In an example, a second expandable chamber can be within a second portion of a cup clockwise between the 315-degree and 45-degree latitudinal spokes. In an example, a first expandable chamber can be within a first portion of a cup clockwise between the 0-degree and 90-degree latitudinal spokes. In an example, a second expandable chamber can be within a second portion of a cup clockwise between the 180-degree and 270-degree latitudinal spokes.

In an example, this device can comprise two expandable chambers which are on either side of a virtual plane which intersects the cup in an anterior-to-posterior direction. In an example, this virtual plane can be a vertical plane which intersects the cup along the 0-degree-to-180-degree latitudinal lines. In an example, this virtual plane can be a horizontal plane which intersects the cup along the 270-degree-to-90-degree latitudinal lines. In an example, for the right-side cup, this virtual plane can be an angular plane which intersects the cup along the 315-degree-to-135-degree latitudinal lines. In an example, for the left-side cup, this virtual plane can be an angular plane which intersects the cup along the 225-degree-to-45-degree latitudinal lines.

In an example, first and second expandable chambers can be located to the left and to the right, respectively, of a vertical anterior-to-posterior virtual plane which intersects the cup. In an example, light emitters and light receivers can be located to the left and to the right, respectively, of a vertical anterior-to-posterior virtual plane which intersects the cup. In an example, first and second expandable chambers can be located below and above, respectively, a horizontal anterior-to-posterior virtual plane which intersects the cup. In an example, light emitters and light receivers can be located below and above, respectively, a horizontal anterior-to-posterior virtual plane which intersects the cup. In an example, first and second expandable chambers can be located to the lower left and to the upper right, respectively, of a 45-degree diagonal anterior-to-posterior virtual plane which intersects the cup. In an example, light emitters and light receivers can be located to the lower left and to the upper right, respectively, of a 45-degree diagonal anterior-to-posterior virtual plane which intersects the cup.

In an example, this device can comprise a first expandable chamber on (or in) the right side of the concave interior of a cup and a second expandable chamber on (or in) the left side of the concave interior of the cup. In an example, this device can comprise a first expandable chamber on (or in) the upper half of the interior of a cup and a second expandable chamber on (or in) the lower half of the interior of the cup. In an example, this device can comprise a first expandable chamber on (or in) the upper right quadrant (from a frontal corona view) of a cup for a right-side breast and a second expandable chamber on (or in) the lower left quadrant (from a frontal corona view) of the interior of the cup. In an example, this device can comprise a first expandable chamber on (or in) the upper left quadrant (from a frontal corona view) of a cup for a left-side breast and a second expandable chamber on (or in) the lower right quadrant (from a frontal corona view) of the interior of the cup.

In an example, a first expandable chamber can be in a first half of the concavity of a cup which is on a first side of an anterior-to-posterior plane which intersects the cup and a second expandable chamber can be in a second half of the concavity of a cup which is on a second side of the plane. In an example, a first expandable chamber can be in a first (e.g. right) half of the concavity of a cup which is on a first side of a vertical anterior-to-posterior plane which intersects the cup and a second expandable chamber can be in a second (e.g. left) half of the concavity of a cup which is on a second side of the plane.

In an example, a first expandable chamber can be in a first (e.g. right) half of the concavity of a cup which is on a first side of an anterior-to-posterior plane which intersects the cup along the 0-degree latitudinal and 180-degree latitudinal lines (or is parallel to those lines) and a second expandable chamber can be in a second (e.g. left) half of the concavity of a cup which is on a second side of the plane. In an example, a first expandable chamber can be in a first (e.g. lower) half of the concavity of a cup which is on a first side of an anterior-to-posterior plane which intersects the cup and a second expandable chamber can be in a second (e.g. upper) half of the concavity of a cup which is on a second side of the plane.

In an example, a first expandable chamber can be in a first (e.g. lower) half of the concavity of a cup which is on a first side of an anterior-to-posterior plane which intersects the cup along the 270-degree latitudinal and 90-degree latitudinal lines (or is parallel to those lines) and a second expandable chamber can be in a second (e.g. upper) half of the concavity of a cup which is on a second side of the plane. In an example, a first expandable chamber can be in a first (e.g. lower-left) half of the concavity of a cup which is on a first side of a diagonal anterior-to-posterior plane which intersects the cup and a second expandable chamber can be in a second (e.g. upper-right) half of the concavity of a cup which is on a second side of the plane.

In an example, a first expandable chamber can be in a first (e.g. lower-left) half of the concavity of a cup which is on a first side of an anterior-to-posterior plane which intersects the cup along the 315-degree latitudinal and 135-degree latitudinal lines (or is parallel to those lines) and a second expandable chamber can be in a second (e.g. upper-right) half of the concavity of a cup which is on a second side of the plane. In an example, a first expandable chamber can be in a first (e.g. lower-right) half of the concavity of a cup which is on a first side of an anterior-to-posterior plane which intersects the cup along the 225-degree latitudinal and 45-degree latitudinal lines (or is parallel to those lines) and a second expandable chamber can be in a second (e.g. upper-left) half of the concavity of a cup which is on a second side of the plane.

In an example, a first expandable chamber can be in a first half of the concavity of a cup which is on a first side of an anterior-to-posterior plane which intersects the cup and no closer than ¼ inch from the plane. In an example, a second expandable chamber can be in a second half of the concavity of a cup which is on a second side of the plane and no closer than ¼ inch from the plane. In an example, a first expandable chamber can be in a first half of the concavity of a cup which is on a first side of an anterior-to-posterior plane which intersects the cup and no closer than ½ inch from the plane. In an example, a second expandable chamber can be in a second half of the concavity of a cup which is on a second side of the plane and no closer than ½ inch from the plane. In an example, a first expandable chamber can be in a first half of the concavity of a cup which is on a first side of an anterior-to-posterior plane which intersects the cup and no closer than 1 inch from the plane. In an example, a second expandable chamber can be in a second half of the concavity of a cup which is on a second side of the plane and no closer than 1 inch from the plane.

In an example, a cup on one side (e.g. the right side or left side) of a bra can have a similar (e.g. same, but symmetric) configuration of expanding chambers, light emitters, and light receivers as a cup on the other side (e.g. the left side or right side) of the bra. In an example, a cup on one side of a bra can have a similar (e.g. same, but reflected across a central vertical plane) configuration of expanding chambers, light emitters, and light receivers as a cup on the other side of the bra.

In an example, the side and/or surface of an expandable chamber which faces toward the center of the breast can be more elastic than the side of the chamber which faces away from the center of the breast. In an example, the side and/or surface of an expandable chamber which faces away from the perimeter of a cup can be more elastic than the side of the chamber which faces toward the perimeter of the cup. In an example, the side and/or surface of an expandable chamber which faces away from the 90-degree longitudinal ring can be less elastic than the side of the chamber which faces away from the from the 90-degree longitudinal ring.

In an example, the side and/or surface of an expandable chamber which faces away from the perimeter of a cup can have a lower Young's modulus than the side of the chamber which faces toward the perimeter of the cup. In an example, the side and/or surface of an expandable chamber which faces toward the center of the breast can have a lower Young's modulus than the side of the chamber which faces away from the center of the breast. In an example, the side and/or surface of an expandable chamber which faces away from the 90-degree longitudinal ring can have a lower Young's modulus than the side of the chamber which faces away from the from the 90-degree longitudinal ring.

In an example, an inelastic portion of a cup can cause an expandable chamber to expand inward into breast tissue (more than outward through expansion of the outer perimeter of the cup). This can help to flatten the breast for improved optical scanning In an example, inelastic portions of a cup can have a higher Young's modulus than the rest of the cup. In an example, inelastic portions of a cup can have a higher Young's modulus than the other portions of the cup. In an example, inelastic portions of a cup can be rigid or inflexible. In an example, inelastic portions of a cup can comprise wire reinforcement of the portion of the cup. In an example, inelastic portions of a cup can comprise reinforcement of the portion of the cup with metal or plastic.

In an example, there can be more than two expandable chambers in the concave interior of a cup. In an example, there can be two or more expandable chambers on each side of the cup. In an example, two or more expandable chambers on the same side of a cup can have different values for Young's modulus. In an example, there can be two or more expandable chambers in the upper right quadrant of a cup and two or more expandable chambers in the lower left quadrant of the cup. In an example, two or more expandable chambers on the same side of a cup can be expanded by different amounts.

In an example, two or more expandable chambers on the same side of a cup can be expanded by different percentages. In an example, two or more expandable chambers on the same side of a cup can have different elasticities. In an example, there can be two or more expandable chambers on the right side of a cup and two or more expandable chambers on the left side of the cup. In an example, there can be two or more expandable chambers in the upper left quadrant of a cup and two or more expandable chambers in the lower right quadrant of the cup.

In an example, expansion of two or more expandable chambers on the same side of a cup can be individually and selectively controlled and/or adjusted. In an example, one chamber on a given side or half can be closer to the apex of the breast or cup and the other chamber on that side or half can be closer to the (90-degree longitudinal) perimeter of the breast or cup. In an example, two or more expandable chambers on the same side of a cup can be expanded simultaneously. In an example, there can be two or more expandable chambers on the upper half of a cup and two or more expandable chambers on the lower half of the cup. In an example, two or more expandable chambers on the same side of a cup can be expanded sequentially.

In an example, there can be different expandable chambers at different longitudes on a side of a cup. In an example, there can be a plurality of expandable chambers located at a plurality of longitudes, respectively, on a side of a cup. In an example, there can be different expandable chambers between different longitudinal rings, respectively, on a side of a cup. In an example, there can be one expandable chamber between the 30-degree and 45-degree longitudinal rings on a side of a cup and another expandable chamber between the 45-degree and 90-degree longitudinal rings on that side of the cup. In an example, these different expandable chambers can have different elasticities and/or be inflated at different times to help compress the breast into a better shape for optical scanning.

In an example, there can be different expandable chambers at different latitudes on a side of a cup. In an example, there can be a plurality of expandable chambers located at a plurality of latitudes, respectively, on a side of a cup. In an example, there can be different expandable chambers between different latitudinal spokes, respectively, on a side of a cup. In an example, these different expandable chambers can have different elasticities and/or be inflated at different times to help compress the breast into a better shape for optical scanning.

In an example, expandable chambers which are closer to the perimeter of a breast can be expanded more in their second configurations than expandable chambers which are closer to the apex of the breast. This can compress a breast into a more-flattened configuration (e.g. more uniform width) for better optical scanning to detect and/or image abnormal breast tissue. In an example, a device can also comprise multiple control mechanisms which enable the person whose breast is being compressed to control the rate and/or amount of compression, including options for stopping further compression. In an example, these control mechanisms can include a voice recognition mechanism and/or a "dead-man's switch" mechanism (which requires continual positive hand squeezing to continue chamber expansion).

In an example, there can be two or more expandable chambers on each side of an anterior-to-posterior virtual plane which intersects a bra cup. In this example, one expandable chamber can be closer to the apex of a cup or breast than another expandable chamber on the same side of a virtual plane. In an example, the centroid of one expandable chamber can be closer to the apex of a cup or breast than the centroid of another expandable chamber on the same side of a virtual plane. In an example, the centroid of one expandable chamber can be closer to the apex of a cup or breast than the centroid of another expandable chamber on the same side of a virtual plane when the device is in the first configuration, in the second configuration, or both.

In an example, one expandable chamber can be closer to the surface of a breast than another expandable chamber on the same side of a virtual plane. In an example, the centroid of one expandable chamber can be closer to the surface of a breast than the centroid of another expandable chamber on the same side of a virtual plane. In an example, the centroid of one expandable chamber can be closer to the surface of a breast than the centroid of another expandable chamber on the same side of a virtual plane when the device is in the first configuration, in the second configuration, or both.

In an example, a first expandable chamber can be expanded before a second chamber on the same side of a virtual plane is expanded. In an example, a first expandable chamber can be expanded more than a second chamber on the same side of a virtual plane is expanded. In an example, a first expandable chamber can be expanded by a greater percentage than a second chamber on the same side of a virtual plane is expanded. In an example, a first expandable chamber can be expanded to a greater pressure than that of a second chamber on the same side of a virtual plane.

In an example, different expandable chambers on the same side of a virtual plane can be expanded by the same amount (e.g. by the same percentage or to the same internal pressure level). In an example, different expandable chambers on the same side can be expanded by different amounts (e.g. by different percentages or to different internal pressure levels). In an example, expandable chambers which are closer to the apex of a cup or breast can be expanded more than expandable chambers which are farther from the apex of a cup or breast. In an example, differential expansion of different chambers in a set of expandable chambers can help to compress a portion of a breast into a shape with more uniform width (e.g. flatter).

In an example, this device can further comprise a plurality of air tubes which conduct a flowable substance (e.g. a gas or liquid) into a plurality of expandable chambers. In an example, this device can further comprise a plurality of air tubes which are in fluid communication with the interiors of a plurality of expandable chambers, respectively. In an example, there can be a separate air tube in fluid communication with the interiors of each expandable chamber. In an example, a smart bra can have ports and/or valves which connect internal air tubes through the body of the bra to external air tubes from a separate air pump. In an example, air tubes from the air pump can be connected to the bra via the ports and/or valves for expanding chambers within the cups of the bra. Alternatively, the back strap of the bra can include a built-in air pump which pumps air into expanding chambers when pressed repeatedly.

In an example, this device can further comprise one or more pressure sensors which measure pressure levels within one or more expandable chambers. In an example, the amount of gas or fluid can be pumped into one or more expandable chambers can be adjusted to achieve one or more selected pressure levels. In an example, expansion of one or more expandable chambers can be adjusted and/or controlled to achieve a desired level of compression of the breast. In an example, expansion of one or more expandable chambers can be adjusted and/or controlled to achieve a desired level of compression of the width of the breast. In an example, expansion of one or more expandable chambers can be adjusted and/or controlled to achieve a desired width of the breast. In an example, expansion of one or more expandable chambers can be adjusted and/or controlled to achieve a desired level of pressure on breast tissue.

In an example, expansion of first and second expandable chambers can compress a portion of a breast between them. This enables more accurate optical scanning of breast tissue because light rays travel a shorter distance through tissue. In an example, the portion of the breast between the first and second expandable chambers has a first width in the first configuration of the device and a second width in the second configuration of the device, wherein the second width is less than the first width. In an example, the portion of the breast between the first and second expandable chambers is made flatter in the second configuration of the device.

In an example, the portion of the breast between the first and second expandable chambers has a first width in the first configuration of the device and a second width in the second configuration of the device, wherein the second width is less than 75% of the first width. In an example, the portion of the breast between the first and second expandable chambers has a first width in the first configuration of the device and a second width in the second configuration of the device, wherein the second width is less than 50% of the first width. In an example, applying greater compression to the base of a breast than to the apex area of a breast can help to flatten the breast more uniformly. This can enable more uniform optical scanning of breast tissue for better detection and/or imaging of abnormal breast tissue.

In an example, the amount of light passing through breast tissue between the plurality of light emitters and the plurality of light receivers can be monitored during expansion of the expandable chambers. In an example, expandable chambers can be expanded until a minimum target level and/or percentage of light emitted from light emitters is received by light receivers after passing through breast tissue. In an example, the expandable chambers are expanded until the amount of light diffusion through breast tissue is reduced to a target level and/or percentage.

In an example, expandable chambers can be expanded until light received by light receivers reaches a minimum target level of resolution and/or a maximum level of scattering. In an example, the expandable chambers are expanded until either a target level of imaging resolution is achieved or the person indicates an unacceptable level of discomfort. In an example, the device can further comprise a microphone which enables the person to control (e.g. stop) expansion of the chambers by verbal commands. In an example, the device can further comprise a remote control which enables the person to control (e.g. stop) expansion of the chambers.

In an example, a light emitter in a plurality of light emitters can be a Light Emitting Diode (LED). In an example, a light emitter can be an Organic Light Emitting Diode (OLED). In an example, a light emitter can be an Active Matrix Organic Light-Emitting Diode (AMOLED). In an example, a light emitter can be a Single Photon Avalanche Diode (SPAD). In an example, a light emitter can be a microscale LED. In an example, a light emitter can be a MicroLED. In an example, a light emitter can be a nanoscale LED. In an example, a light emitter can be a laser. In an example, a light emitter can be a laser LED. In an example, a light emitter can be a Light-Emitting Electrochemical Cell (LEC).

In an example, a light emitter (such as an LED) can be embedded within yarns or fibers used to make a fabric or textile used to make the cup of this device. In an example, a light emitter (such as an LED) can be attached to a fabric or textile which is used to make the cup of this device. In an example, a light emitter can be printed on a fabric or textile. In an example, a light emitter can be made by 3D printing. In an example, a light emitter can be encapsulated with a waterproof coating for protection from moisture. In an example, a light emitter can be encapsulated in acrylic material for protection from moisture.

In an example, light emitters can be located between expandable chambers and the surface of a breast. In an example, a light emitter can be made with polydimethylsiloxane (PDMS) or another silicone-based polymer. In an example, a light emitter can be made with an acrylic elastomer. In an example, a light emitter can be made with polyethylene terephthalate (PET). In an example, a light emitter can be made with poly(3,4-ethylenedioxythiophene) polystyrene sulfonate (PEDOT:PSS). In an example, a light emitter can made with poly(darton).
In an example, a light emitter can be made with a combination of poly(3,4-ethylenedioxythiophene) polystyrene sulfonate (PEDOT:PSS) and carbon nanotubes.

In an example, a light emitter can emit near-infrared light. In an example, a light emitter can emit coherent light. In an example, a light emitter can emit light in pulses. In an example, a light emitter can emit near-infrared light and/or coherent light. In an example, a light emitter can emit polarized light. In an example, light emitters can be lasers. In an example, a light emitter can be an LED (Light Emitting Diode). In an example, an LED can be selected from the group consisting of: encapsulated LED, infrared LED, monochromatic LED, near-infrared LED, organic light emitting diode (OLED), resonant cavity light emitting diode (RCLED), super-luminescent light emitting diode (SLED), and tunable LED. In an example, a laser can be selected from the group consisting of: continuous-wave laser, green-light laser, infrared laser, laser, laser diode, multi-wavelength laser, pulsatile laser, red-light laser, super-luminescent laser, and ultraviolet laser. In an example, a light emitter can be a coherent light emitter, an infrared light emitter, a near-infrared light emitter, and an ultraviolet light emitter.

In an example, a light emitter can emit light with a frequency between 598 and 603 nm. In an example, a light emitter can emit light energy with a wavelength in the range of 600 to 700 nm. In an example, a first light emitter can emit light with a wavelength in the range of 600 to 700 nm at a first time; a second light emitter can emit light with a wavelength in the range of 700 nm to 800 nm at a second time; and a third light emitter can emit light with a wavelength in the range of 800 nm to 900 nm at a third time. In an example, a first light emitter can emit light with a wavelength in the range of 600 to 700 nm; a second light emitter can emit light with a wavelength in the range of 700 nm to 800 nm; and a third light emitter can emit light with a wavelength in the range of 800 nm to 900 nm.

In an example, a light emitter can emit light with a frequency between 658 and 663 nm. In an example, a light emitter can emit light with a frequency between 668 and 673 nm. In an example, a first light emitter can emit light with a wavelength in the range of 650 to 700 nm; a second light emitter can emit light with a wavelength in the range of 700 nm to 750 nm; and a third light emitter can emit light with a wavelength in the range of 750 nm to 800 nm. In an example, a first light emitter on a cup can emit light with a wavelength in the range of 650 to 700 nm; a second light emitter on the cup can emit light with a wavelength in the range of 700 nm to 750 nm; and a third light emitter can emit light with a wavelength in the range of 750 nm to 800 nm.

In an example, a light emitter can emit light with a frequency between 688 and 693 nm. In an example, a first light emitter can emit light with a wavelength in the range of 650 to 750 nm at a first time; a second light emitter can emit light with a wavelength in the range of 750 nm to 850 nm at a second time; and a third light emitter can emit light with a wavelength in the range of 850 nm to 950 nm at a third time. In an example, a first light emitter can emit intensity or amplitude modulated light into the breast with a wavelength in the range of 650 to 750 nm; a second light emitter can emit intensity or amplitude modulated light with a wavelength in the range of 750 nm to 850 nm; and a third light emitter can emit intensity or amplitude modulated light with a wavelength in the range of 850 nm to 950 nm.

In an example, a first light emitter can emit light with a wavelength in the range of 650 to 750 nm; a second light emitter can emit light with a wavelength in the range of 750 nm to 850 nm; and a third light emitter can emit light with a wavelength in the range of 850 nm to 950 nm. In an example, a first light emitter can emit light with a wavelength in the range of 650 to 750 nm; a second light emitter on the (base) perimeter of the cup can emit light with a wavelength in the range of 750 nm to 850 nm; and a third light emitter can emit light with a wavelength in the range of 850 nm to 950 nm.

In an example, a first light emitter can emit light with a wavelength in the range of 600 to 800 nm at a first time; a second light emitter can emit light with a wavelength in the range of 800 nm to 1000 nm at a second time; and a third light emitter can emit light with a wavelength in the range of 1000 nm to 1200 nm at a third time. In an example, a first light emitter can emit light with a wavelength in the range of 600 to 800 nm; a second light emitter can emit light with a wavelength in the range of 800 nm to 1000 nm; and a third light emitter can emit light with a wavelength in the range of 1000 nm to 1200 nm. In an example, a light emitter can emit light with a frequency between 698 and 703 nm.

In an example, a first light emitter can emit light with a wavelength in the range of 600 to 900 nm at a first time and a second light emitter can emit light with a wavelength in the range of 900 nm to 1200 nm at a second time. In an example, a first light emitter can emit light with a wavelength in the range of 600 to 900 nm at a first time; a second light emitter can emit light with a wavelength in the range of 900 nm to 1200 nm at a second time; and a third light emitter can emit light with a wavelength in the range of 1200 nm to 1500 nm at a third time In an example, a first light emitter can emit light with a wavelength in the range of 600 to 900 nm and a second light emitter can emit light with a wavelength in the range of 900 nm to 1200 nm. In an example, a first light emitter on a cup can emit light with a wavelength in the range of 600 to 900 nm; a second light emitter on the cup can emit light with a wavelength in the range of 900 nm to 1200 nm; and a third light emitter can emit light with a wavelength in the range of 1200 nm to 1500 nm.

In an example, a light emitter can emit light with a frequency between 748 and 753 nm. In an example, a light emitter can emit light with a frequency between 763 and 768 nm. In an example, a light emitter can emit light with a frequency between 778 and 783 nm. In an example, a light emitter can emit light with a frequency between 783 and 788 nm. In an example, a light emitter can emit light energy with a wavelength in the range of 600 nm to 1,000 nm. In an example, a light emitter can emit light with a frequency between 798 and 803 nm. In an example, a light emitter can emit light with a frequency between 806 and 811 nm. In an example, a light emitter can emit light with a frequency between 825 and 830 nm. In an example, a light emitter can emit light with a frequency between 828 and 833 nm.

In an example, a light emitter can emit light with a frequency between 848 and 853 nm. In an example, a light emitter can emit light energy with a wavelength in the range of 850 to 950 nm. In an example, a light emitter can emit light with a frequency between 916 and 921 nm. In an example, a light emitter can emit light with a frequency between 978 and 983 nm. In an example, a light emitter can emit light with a frequency between 1098 and 1103 nm. In an example, a light emitter can emit light with a frequency between 1208 and 1213 nm. In an example, a light emitter can emit light with a frequency between 1398 and 1403 nm. In an example, a light emitter can emit light with a frequency between 1501 and 1506 nm. In an example, a light emitter can emit light with a frequency between 1698 and 1703 nm. In an example, a light emitter can emit light with a frequency between 1798 and 1803 nm.

In an example, light emitters can emit light at a constant frequency and/or wavelength. In an example, a light emitter can emit light at a frequency and/or a spectral range which varies over time. In an example, a light emitter can emit light at different wavelengths at different times. In an example, a light emitter can emit light at a constant frequency and/or in a constant spectral range. In an example, different light emitters in an array can emit light at different wavelengths. In an example, different light emitters in a ring can emit light at different wavelengths. In an example, different light emitters can emit light at different wavelengths. In an example, light emitters can emit light at a frequency and/or wavelength which varies over time. In an example, light emitters on a cup can emit frequency and/or wavelength modulated light. In an example, a light emitter can emit intensity or amplitude-modulated light.

In an example, a single light emitter can emit light at a frequency and/or wavelength which varies over time. In an example, a single light emitter can emit light at different wavelengths at different times. In an example, light emitters can all emit light at the same frequency and/or wavelength (or in the same spectral range). In an example, two or more different light emitters in an array or matrix can emit light at different wavelengths. In an example, a first set of light emitters can emit light at a first frequency and/or wavelength (or in a first spectral range), a second set of light emitters can emit light at a second frequency and/or wavelength (or in a second spectral range), and a third set of light emitters can emit light at a third frequency and/or wavelength (or in a third spectral range). In an example, a first set of light emitters on a cup can emit light at a first frequency and/or wavelength (or in a first spectral range) and a second set of light emitters on the cup can emit light at a second frequency and/or wavelength (or in a second spectral range).

In an example, light emitters can all emit a pulse of light at the same time. In an example, light emitters can all emit light at the same intensity or amplitude level (or at the same time). In an example, a first light emitter at a first location can emit (a pulse of) light at a first time and a second light emitter at a second location can emit (a pulse of) light at a second time. In an example, a first light emitter can emit a pulse of light with a first duration and a second light emitter can emit a pulse of light with a second duration, wherein the second duration is greater than the first duration. In an example, a first set of light emitters can emit light at a first intensity or amplitude level (or at a first time) and a second set of light emitters can emit light at a second intensity or amplitude level (or at a second time). In an example, a light emitter can emit a first pulse of light with a first duration followed by a second pulse of light with a second duration, wherein the second duration is greater than the first duration.

In an example, light emitters in a first quadrant of a cup can emit (a pulse of) light at a first time and light emitters in a second quadrant of the cup can emit (a pulse of) light at a second time. In an example, light emitters on the right side of a cup can emit (a pulse of) light at a first time and light emitters on the left side of the cup can emit (a pulse of) light at a second time, or vice versa. In an example, light emitters on the top half of a cup can emit (a pulse of) light at a first time and light emitters on the bottom half of the cup can emit (a pulse of) light at a second time, or vice versa In an example, light emitters one a first of light emitters can emit (a pulse of) light at a first time and light emitters on a second ring of light emitters can emit (a pulse of) light at a second time.

In an example, an array of light emitters can comprise an array of near-infrared, continuous wave light emitters. In an example, light can be emitted from light emitters in very short pulses. In an example, light emitters can be continuous wave light emitters. In an example, light emitters can emit short pulses of light. In an example, a light emitter can be a laser with a narrow pulse width. In an example, different light emitters in an array of light emitters can emit light at different times. In an example, light emission from light emitters can be multiplexed.

In an example, a light emitter can emit light with a variable frequency. In an example, a light emitter can emit light with a wavelength and/or frequency which changes over time. In an example, a light emitter can emit light with a wavelength and/or frequency which changes in a repeated cyclical pattern over time. In an example, a light emitter can emit coherent light. In an example, a light emitter can emit light pulses. In an example, a light emitter can emit light via Alternating Current Electroluminescence (ACEL).

In an example, a light emitter can emit light at an angle and/or along a focal vector which varies over time. In an example, an optical component can include an electromagnetic actuator which changes the angle and/or focal vector of light emission over time. In an example, angles between the focal vectors of light beams emitted from light emitters and the surface of a breast or cup can vary with the distance of those light emitters from the apex of a cup. In an example, a light emitter can be positioned so as to emit light along a vector which is substantially perpendicular to a breast or cup surface. In an example, angles between the focal vectors of light emitted from light emitters and the surface of a breast or cup can increase with the distance of the light emitters from the apex of the concave surface of a breast or cup.

In an example, angles between the focal vectors of light emitted from light emitters and the surface of a breast or cup can decrease with the distance of the light emitters from the apex of a cup. In an example, angles between the focal vectors of light emitted from light emitters which are closer to the apex of a cup can be more perpendicular relative to the surface of a breast or cup than the focal vectors of light emitted from light emitters which are farther from the apex of the cup. In an example, a light emitter can emit light along a vector which: perpendicular to a breast or cup surface; toward a breast or cup centroid; and/or toward a particular light receiver.

In an example, the focal vectors of light emitted from light emitters which are farther from the apex of the concave surface of a breast or cup can be closer to perpendicular to that surface than the focal vectors of light emitted from light emitters which are closer to the apex of the concave surface of the breast or cup. In an example, these angles can be correlated with, or even proportional to, this distance. In an example, a light emitter can emit light at a constant angle and/or focal vector. In an example, a light emitter can be oriented to emit light along a vector which is substantially perpendicular to a breast or cup surface.

In an example, a light emitter can be positioned so as to emit light along a vector which is: substantially perpendicular to a breast or cup surface; directed toward a breast or cup centroid; and/or directed toward a particular light receiver. In an example, angles between the focal vectors of light beams emitted from light emitters and the surface of a breast or cup can vary with the distance of the light emitters from the apex of the concave surface of a breast or cup. In an example, a light emitter can be positioned so as to emit light toward a particular light receiver. In an example, a light emitter can emit a radially-rotating beam of light. In an example, a light emitter can be oriented to emit light toward the center of the breast or cup. In an example, a light emitter can be positioned so as to emit light toward the centroid of a breast or cup.

In an example, a light emitter can be flexible. In an example, an LED light emitter can be flexible. In an example, a light emitter can be made with a flexible and/or elastomeric material. In an example, a light emitter can be made with polydimethylsiloxane (PDMS). In an example, an LED can be made with polydimethylsiloxane (PDMS). In an example, an ACEL-based light emitter can be made with polydimethylsiloxane (PDMS). In an example, an OLED light emitter can be made with polydimethylsiloxane (PDMS).

In an example, light emitters can receive power from flexible electroconductive pathways in a cup. In an example, light emitters can receive power from undulating (e.g. sinusoidal) electroconductive pathways in a cup. In an example, light emitters can receive power from undulating (e.g. sinusoidal) wires in a cup. In an example, light emitters can receive power from electroconductive yarn pathways in a cup. In an example, each light emitter in an array can be powered by a separate electroconductive pathway.

In an example, an array of light emitters can comprise nested rings of light emitters. In an example, an array of light emitters can comprise concentric rings of light emitters. In an example, an array of light emitters can comprise an orthogonal matrix (e.g. quadrilateral grid) of light emitters. In an example, an array of light emitters can comprise a row-and-column matrix (e.g. grid) of light emitters. In an example, an array of light emitters can comprise a hub-and-spoke array of light emitters. In an example, an array of light emitters can comprise a start burst array of light emitters.

In an example, an array of light emitters can comprise a honeycomb (e.g. hexagonal grid) array of light emitters. In an example, an array of light emitters can comprise a checkerboard array of light emitters. In an example, the number of latitudinal lines populated by light emitters can increase with distance from the apex of a cup. In an example, light emitters can be arranged in a spiral or helical pattern. In an example, light emitters can be arranged in a star-shaped pattern. In an example, the number of latitudinal lines populated by light emitters can decrease with distance from the apex of a cup.

In an example, an array of light emitters can have a helical or half-helical shape. In an example, an array of light emitters can be distributed along a helical or half-helical elastic conductive pathway. In an example, an array of light emitters can have an undulating/sinusoidal shape. In an example, an array of light emitters can be distributed along an undulating/sinusoidal elastic conductive pathway. In an example, an array of light emitters can comprise light emitters along radial strips which extend outward from the apex of a breast or cup. In an example, an array of light emitters can comprise light emitters along radial strips which extend outward from a central (e.g. <25 degree) longitudinal ring of a breast or cup.

In an example, a light emitter can be adhered to a fabric or textile using a transparent adhesive substance. In an example, a light emitter can be deposited on a fabric and/or textile by screen printing. In an example, a light emitter can be deposited on a fabric and/or textile by 3D printing. In an example, a light emitter can be encapsulated in an acrylic elastomer to protect it from moisture. In an example, light emitters can be attached to a pre-made electroconductive circuit on a cup. In an example, light emitters can be attached to a printed electroconductive circuit on a cup.

In an example, light emitters can be embedded in a flexible transparent layer between expandable chambers and the breast. In an example, light emitters can be embedded in a flexible elastic layer between expandable chambers and the breast. In an example, light emitters can be part of a flexible elastic layer between expandable chambers and the breast. In an example, light emitters can be woven into a fabric or textile which is used to make a cup. In an example, light emitters on a cup can be encapsulated to protect them from moisture. In an example, light emitters can be located along the surfaces and/or sides of the expandable chambers which face the breast.

In an example, light emitters can be equally distributed over a given area of a cup. In an example, light emitters can be equally distributed on a given side (e.g. right or left, lower or upper) of a cup. In an example, light emitters can be equally distributed on the breast-facing side of an expandable chamber. In an example, light emitters can be farther apart toward the apex of a cup and closer together toward the periphery of the cup. In an example, light emitters along longitudinal lines can be farther apart closer to the apex of a cup. In an example, light emitters can be evenly spaced along longitudinal lines. In an example, light emitters can be evenly spaced along latitudinal lines.

In an example, a greater number of latitudinal lines can be populated by light emitters in areas of the cup which are farther from the apex of the cup. In an example, light emitters can be closer together toward the apex of a cup and farther apart toward the periphery of the cup. In an example, light emitters can be closer together near the 315-degree to 135-degree latitudinal lines on a cup, as compared to other areas on the cup. In an example, light emitters can be closer together in the upper-left quadrant of the cup on right breast, as compared to other quadrants on that cup. In an example, light emitters along latitudinal lines can be father apart closer to the apex of a cup. In an example, light emitters can be closer together in the upper-right quadrant of the cup on left breast, as compared to other quadrants on that cup.

In an example, in an example, there can be equal numbers of light emitters on either side of an anterior-to-posterior plane which is parallel to the line connecting 0-degrees and 180-degrees in a coronal (e.g. frontal) view. In an example, in an example, there can be equal numbers of light emitters on either side of an anterior-to-posterior plane which is parallel to the line connecting 270-degrees and 90-degrees in a coronal (e.g. frontal) view. In an example, in an example, there can be equal numbers of light emitters on either side of an anterior-to-posterior plane which is parallel to the line connecting 315-degrees and 135-degrees in a coronal (e.g. frontal) view.

In an example, light emitters can all be in space on the same side of an anterior-to-posterior plane which is parallel to the line connecting 0-degrees and 180-degrees in a coronal (e.g. frontal) view. In an example, light emitters can all be in space on the same side of an anterior-to-posterior plane which is parallel to the line connecting 270-degrees and 90-degrees in a coronal (e.g. frontal) view. In an example, light emitters can all be in space on the same side of an anterior-to-posterior plane which is parallel to the line connecting 315-degrees and 135-degrees in a coronal (e.g. frontal) view.

In an example, the device can further comprise end-emitting optical fibers which guide light from light emitters to one or more emission points on the interior concave surface of a bra cup. In an example, the device can further comprise flexible and/or elastic optical fibers which guide light from a light emitter to one or more locations on the interior of the cup. In an example, the device can further comprise optical fibers which guide light from light emitters to one or more emission points on the interior concave surface of a bra cup. In an example, the device can further comprise optical fibers which guide light from a light emitter to one or more locations on the interior of the cup. In an example, the device can further comprise undulating (e.g. sinusoidal) optical fibers which guide light from a light emitter to one or more locations on the interior of the cup. In an example, the device can further comprise side-emitting optical fibers which guide light from light emitters to one or more emission points on the interior concave surface of a bra cup.

In an example, a light receiver can be a photoreceptor. In an example, a light receiver can be a photodiode. In an example, a light receiver can be a photoconductor. In an example, a light receiver can be a thin-film photoreceptor. In an example, a light receiver can be an organic phototransistor. In an example, a light receiver can comprise a fast-gated detector. In an example, a light receiver can have an organic photoactive channel layer, a dielectric layer, and electrodes. In an example, a light receiver can be an organic photodiode. In an example, light from light emitters which has passed breast tissue can be filtered through pinholes before being received by light receivers. In an example, a light receiver can be encapsulated in transparent waterproof material to protect it from moisture.

In an example, a light receiver can be selected from the group consisting of: photodetector, photoresistor, avalanche photodiode (APD), charge-coupled device (CCD), complementary metal-oxide semiconductor (CMOS), infrared detector, infrared photoconductor, infrared photodiode, light dependent resistor (LDR), optoelectric sensor, photoconductor, photodiode, photomultiplier, and phototransistor. In an example, a smart bra can comprise a plurality of stacked photodetectors, multi-layer photodetectors, and/or vertical nanowire arrays which receive light after it has passed through breast tissue. In an example, a light receiver can be a avalanche photo diode (APDs) or PIN photodiode. In an example, a light emitter and a light receiver can combine to form a surface plasmon resonance sensor. In an example, a light receiver can be made with polydimethylsiloxane (PDMS) or another silicone-based polymer. In an example, a light receiver can be made with an acrylic elastomer. In an example, a light receiver can be made with polyethylene terephthalate (PET).

In an example, a light receiver can be made from silicon. In an example, a light receiver can be made from semiconducting polymer. In an example, a light receiver can be made from PEDOT:PSS. In an example, a light receiver can be made from Germanium. In an example, a light receiver can be made from carbon nanotubes. In an example, a light receiver can be made from silver nanowires. In an example, a light receiver can be flexible. In an example, a light receiver can be made from polydimethylsiloxane (PDMS). In an example, a light receiver can be made with polyethylene naphthalate. In an example, a light receiver can be printed on a fabric or textile. In an example, a light receiver can be 3D printed. In an example, a light receiver can be a flexible organic photodetector (OPD). In an example, a light receiver can comprise a bulk heterojunction structure. In an example, a light receiver can comprise a bicontinuous interpenetrating network of donor and acceptor materials. In an example, a light emitter and light receiver can comprise a fluorescence sensor for detecting abnormal breast tissue. In an example, a light receiver can comprise a Bragg grating.

In an example, light receivers can be equally distributed over a given area of a cup. In an example, light receivers can be equally distributed on a given side (e.g. right or left, lower or upper) of a cup. In an example, light receivers can be equally distributed on the breast-facing side of an expandable chamber. In an example, light receivers can be farther apart toward the apex of a cup and closer together toward the periphery of the cup. In an example, light receivers along longitudinal lines can be farther apart closer to the apex of a cup. In an example, light receivers can be evenly spaced along longitudinal lines. In an example, light receivers can be evenly spaced along latitudinal lines.

In an example, light receivers can be evenly spaced along latitudinal lines. In an example, light receivers can be farther apart toward the apex of a cup and closer together toward the periphery of the cup. In an example, a greater number of latitudinal lines can be populated by light receivers in areas of the cup which are farther from the apex of the cup. In an example, light receivers can be closer together in the upper-right quadrant of the cup on left breast, as compared to other quadrants on that cup. In an example, light receivers can be closer together in the upper-left quadrant of the cup on right breast, as compared to other quadrants on that cup. In an example, light receivers can be evenly spaced along longitudinal lines.

In an example, the number of latitudinal lines populated by light receivers can increase with distance from the apex of a cup. In an example, light receivers along latitudinal lines can be father apart closer to the apex of a cup. In an example, light receivers can be evenly distributed (e.g. substantially equidistant from each other) in a cup. In an example, light receivers along longitudinal lines can be farther apart closer to the apex of a cup. In an example, light receivers can be closer together near the 315-degree to 135-degree latitudinal lines on a cup, as compared to other areas on the cup. In an example, light receivers can be between expandable chambers and the breast. In an example, light receivers can be closer together toward the apex of a cup and farther apart toward the periphery of the cup.

In an example, light receivers can be embedded in a flexible transparent layer between expandable chambers and the breast. In an example, light receivers can be embedded in a flexible elastic layer between expandable chambers and the breast. In an example, light receivers can be part of a flexible elastic layer between expandable chambers and the breast. In an example, light receivers can be woven into a fabric or textile which is used to make a cup. In an example, light receivers on a cup can be encapsulated to protect them from moisture.

In an example, an array of light receivers can comprise nested rings of light receivers. In an example, an array of light receivers can comprise an orthogonal matrix (e.g. quadrilateral grid) of light receivers. In an example, an array of light receivers can comprise a hub-and-spoke array of light receivers. In an example, an array of light receivers can comprise a honeycomb (e.g. hexagonal grid) array of light receivers. In an example, an array of light receivers can comprise a checkerboard array of light receivers. In an example, light receivers can be arranged in a spiral or helical pattern. In an example, light receivers can be arranged in a star-shaped pattern. In an example, light receivers can be arranged in a star burst pattern.

In an example, in an example, there can be equal numbers of light receivers on either side of an anterior-to-posterior plane which is parallel to the line connecting 315-degrees and 135-degrees in a coronal (e.g. frontal) view. In an example, in an example, there can be equal numbers of light receivers on either side of an anterior-to-posterior plane which is parallel to the line connecting 0-degrees and 180-degrees in a coronal (e.g. frontal) view. In an example, light receivers can all be in space on the same side of an anterior-to-posterior plane which is parallel to the line connecting 0-degrees and 180-degrees in a coronal (e.g. frontal) view. In an example, light receivers can all be in space on the same side of an anterior-to-posterior plane which is parallel to the line connecting 270-degrees and 90-degrees in a coronal (e.g. frontal) view.

In an example, light receivers can be located along the surfaces and/or sides of the expandable chambers which face the breast. In an example, in an example, there can be equal numbers of light receivers on either side of an anterior-to-posterior plane which is parallel to the line connecting 270-degrees and 90-degrees in a coronal (e.g. frontal) view. In an example, light receivers can all be in space on the same side of an anterior-to-posterior plane which is parallel to the line connecting 315-degrees and 135-degrees in a coronal (e.g. frontal) view.

In an example, there can be a first average distance between light emitters and light receivers when the device is in a first configuration (wherein the chambers are not expanded) and a second average distance between light emitters and light receivers when the device is in a second configuration (wherein the chambers are expanded to compress the breast), wherein the second average distance is less than the first average distance. In an example, there can be pairs of light emitters and light receivers. In an example, the first average distance can be the first average distance between pairs of light emitters and light receivers. In another example, there may not be explicit pair relationships between specific light emitters and light receivers. In this other example, the first average distance can be the average distance between all possible combinations between light emitters and light receivers.

In an example, light emitters and receivers which are closer to the 90-degree longitudinal ring can be farther apart than light emitters and receiver which are closer to the apex of the breast and/or cup. In an example, light emitters and receivers which are closer to the 90-degree longitudinal ring can be farther apart than light emitters and receiver which are closer to the apex of the breast and/or cup in the first configuration of the device. In an example, light emitters and receivers which are closer to the 90-degree longitudinal ring can be farther apart than light emitters and receiver which are closer to the apex of the breast and/or cup in both the first and second configurations of the device, but this difference is less in the second configuration than in the first configuration.

In an example, light emitters or receivers in a longitudinal ring can be equidistant from each other. In an example, light emitters or receivers in a ring which is closer to the center of an array can be closer together than those in a ring which is farther from the center of the array. In an example, light emitters or receiver in a ring which is farther from the center of the array can be closer together than those in a ring which is closer to the center of the array.

In an example, an array of light receivers can have a helical or half-helical shape. In an example, an array of light receivers can be distributed along a helical or half-helical elastic conductive pathway. In an example, an array of light receivers can have an undulating/sinusoidal shape. In an example, an array of light receivers can be distributed along an undulating/sinusoidal elastic conductive pathway. In an example, an array of light receivers can comprise light receivers along radial strips which extend outward from the apex of a breast or cup. In an example, an array of light receivers can comprise light receivers along radial strips which extend outward from a central (e.g. <25 degree) longitudinal ring of a breast or cup.

In an example, there can be first number of light emitters and a second number of light receivers in a cup, wherein the first number is at least four times the second number. Light emitters and receivers in a cup on the left breast can be in a symmetric configuration to light emitters and receivers in a cup on the right breast, wherein symmetric is reflected across the central anterior-to-posterior (e.g. axial) plane of a person's body. In an example, there a first number of light emitters and a second number of light receivers in a cup, wherein the second number is at least four times the first number. In an example, there can be an equal number of light emitters and light receivers in a cup. In an example, there can be more light emitters than light receivers in a cup. In an example, there a first number of light emitters and a second number of light receivers in a cup, wherein the first number is at least twice the second number. In an example, there can be more light receivers than light emitters in a cup.

In an example, this device can comprise a cup with an array of light emitters and light receivers which are distributed along the lower perimeter of the cup spanning the 150-degree latitude and 210-degree latitude locations on the perimeter. In an example, this device can comprise a cup with an array of matched pairs of light emitters and light receivers which is distributed around between 25% and 50% of the (base) perimeter of the cup. In an example, this device can comprise a cup with an array of light emitters and light receivers which are distributed along the lower perimeter of the cup between the 120-degree latitude and 240-degree latitude locations on the perimeter. In an example, this device can comprise a cup with an array of matched pairs of light emitters and light receivers which is distributed around at least 50% of the (base) perimeter of the cup.

In an example, this device can comprise a cup with an array of light emitters and light receivers which are distributed along the lower perimeter of the cup spanning the 90-degree latitude and 270-degree latitude locations on the perimeter. In an example, this device can comprise a cup with an array of matched pairs of light emitters and light receivers which is distributed around between 45% and 75% of the (base) perimeter of the cup. In an example, this device can comprise a cup with an array of light emitters and light receivers which are distributed along the lower perimeter of the cup between the 90-degree latitude and 270-degree latitude locations on the perimeter. In an example, this device can comprise a cup with an array of light emitters and light receivers which are distributed along the lower perimeter of the cup spanning the 120-degree latitude and 240-degree latitude locations on the perimeter.

In an example, a plurality of light emitters can be in a first half of the concavity of a cup which is on a first side of an anterior-to-posterior plane which intersects the cup and a plurality of light receivers can be in a second half of the concavity of a cup which is on a second side of the plane. In an example, a plurality of light emitters can be in a first (e.g. right or left) half of the concavity of a cup which is on a first side of a vertical anterior-to-posterior plane which intersects the cup and a plurality of light receivers can be in a second (e.g. left or right) half of the concavity of a cup which is on a second side of the plane.

In an example, a plurality of light emitters can be in a first (e.g. right or left) half of the concavity of a cup which is on a first side of an anterior-to-posterior plane which intersects the cup along the 0-degree latitudinal and 180-degree latitudinal lines (or is parallel to those lines) and a plurality of light receivers can be in a second (e.g. left or right) half of the concavity of a cup which is on a second side of the plane. In an example, a plurality of light emitters can be in a first (e.g. lower or upper) half of the concavity of a cup which is on a first side of an anterior-to-posterior plane which intersects the cup and a plurality of light receivers can be in a second (e.g. upper or lower) half of the concavity of a cup which is on a second side of the plane.

In an example, a plurality of light emitters can be in a first (e.g. lower or upper) half of the concavity of a cup which is on a first side of an anterior-to-posterior plane which intersects the cup along the 270-degree latitudinal and 90-degree latitudinal lines (or is parallel to those lines) and a plurality of light receivers can be in a second (e.g. upper or lower) half of the concavity of a cup which is on a second side of the plane. In an example, a plurality of light emitters can be in a first (e.g. lower-left) half of the concavity of a cup which is on a first side of a diagonal anterior-to-posterior plane which intersects the cup and a plurality of light receivers can be in a second (e.g. upper-right) half of the concavity of a cup which is on a second side of the plane.

In an example, a plurality of light emitters can be in a first (e.g. lower-left) half of the concavity of a cup which is on a first side of an anterior-to-posterior plane which intersects the cup along the 315-degree latitudinal and 135-degree latitudinal lines (or is parallel to those lines) and a plurality of light receivers can be in a second (e.g. upper-right) half of the concavity of a cup which is on a second side of the plane. In an example, a plurality of light emitters can be in a first (e.g. lower-right) half of the concavity of a cup which is on a first side of an anterior-to-posterior plane which intersects the cup along the 225-degree latitudinal and 45-degree latitudinal lines (or is parallel to those lines) and a plurality of light receivers can be in a second (e.g. upper-left) half of the concavity of a cup which is on a second side of the plane.

In an example, a plurality of light emitters can be in a first half of the concavity of a cup which is on a first side of an anterior-to-posterior plane which intersects the cup and no closer than ¼ inch from the plane. In an example, a plurality of light receivers can be in a second half of the concavity of a cup which is on a second side of the plane and no closer than ¼ inch from the plane. In an example, a plurality of light emitters can be in a first half of the concavity of a cup which is on a first side of an anterior-to-posterior plane which intersects the cup and no closer than ½ inch from the plane. In an example, a plurality of light receivers can be in a second half of the concavity of a cup which is on a second side of the plane and no closer than ½ inch from the plane. In an example, a plurality of light emitters can be in a first half of the concavity of a cup which is on a first side of an anterior-to-posterior plane which intersects the cup and no closer than 1 inch from the plane. In an example, a plurality of light receivers can be in a second half of the concavity of a cup which is on a second side of the plane and no closer than 1 inch from the plane.

Although light energy is significantly diffused through the depth of breast tissue, joint three-dimensional analysis of light transmitted through multiple intersecting vectors between multiple pairs of light emitters and light receivers can increase the accuracy and locational precision of spectroscopic analysis in order to identify and locate abnormal tissue. Joint analysis of the spectral changes of light beams traveling through the breast tissue along different three-dimensional vectors can identify whether there is abnormal tissue within the breast and, if so, where the abnormal tissue is located. In an example, light which has been transmitted through breast tissue between different pairs of light emitters and light receivers (at different times) can be triangulated in order to identify the presence, composition, shape, size, and/or location of abnormal tissue. In an example, light which has been transmitted through breast tissue between different pairs of light emitters and light receivers (at different times) can be jointly analyzed using multivariate analysis in order to identify the presence, composition, shape, size, and/or location of abnormal tissue. In an example, the intersection of light beams traveling along different vectors through breast tissue can be used to triangulate the location (and size and shape) of abnormal breast tissue.

In an example, a device can further comprise flexible electroconductive pathways on a cup can be made from an elastomeric polymer (such as PDMS) which has been impregnated with conductive material. These electroconductive pathways can provide power to light emitters and receivers, as well as transmit data from light receivers to a data processor. In an example, flexible electroconductive pathways on a cup can be made from an elastomeric polymer (such as PDMS) which has been impregnated with silver particles. In an example, electroconductive pathways which provide power to light emitters and receivers can be embroidered onto fabric. In an example, electroconductive yarns which provide power to light emitters and receivers can be embroidered onto fabric. In an example, electroconductive yarns which provide power to light emitters and receivers can be woven or knitted into fabric.

In an example, the device can further comprise flexible elastic conductive pathways which are in electrical communication with light emitters and light receivers on a cup. In an example, there a first number of light emitters and a second number of light receivers in a cup, wherein the second number is at least twice the first number. In an example, flexible electroconductive pathways on a cup can be made from an elastomeric polymer (such as PDMS) which has been impregnated with conductive metal particles. In an example, flexible electroconductive pathways on a cup can be made from an elastomeric polymer (such as PDMS) which has been impregnated with metal particles.

In an example, a cup can further comprise flexible electroconductive pathways which are in electrical communication with light emitters and light receivers. In an example, a cup can further comprise undulating (e.g. sinusoidal or zigzag) wires which are in electrical communication with light emitters and light receivers. In an example, flexible electroconductive pathways on a cup can be made from an elastomeric polymer (such as PDMS) which has been impregnated with carbon nanotubes. In an example, a cup can further comprise undulating (e.g. sinusoidal or zigzag) electroconductive pathways which are in electrical communication with light emitters and light receivers.

In an example, electromagnetic energy can be transmitted to a light emitter or light emitter through an undulating wire, conductive thread, or conductive yarn. In an example, light emitters and/or light receivers can be located where linear elements (e.g. rows and columns) in a grid of electroconductive pathways intersect. In an example, application of electromagnetic energy to two intersecting pathways in a grid can activate a light emitter at the intersection of those two pathways. In an example, a grid can have quadrilateral elements. In an example, intersecting rows and columns in a grid can form quadrilateral openings. In an example, a grid can have hexagonal elements. In an example, intersecting linear elements in a grid can form hexagonal openings. In an example, light emitters and/or light receivers which are closer to the center of a cup can be closer together than those which are farther from the center of the cup (or the center of the grid).

In an example, light which has passed through breast tissue and been received by light receivers can be analyzed to detect levels and/or locations of one or more biological compounds which are associated with abnormal breast tissue. In an example, light receiver by light receivers which has passed through breast tissue can be analyzed to detect levels and/or locations of deoxyhemoglobin. In an example, light receiver by light receivers which has passed through breast tissue can be analyzed to detect levels and/or locations of lipid content. In an example, light receiver by light receivers which has passed through breast tissue can be analyzed to detect levels and/or locations of water. In an example, light receiver by light receivers which has passed through breast tissue can be analyzed to detect levels and/or locations of oxygenated hemoglobin.

In an example, changes in light which has passed through breast tissue and been received by light receivers can be analyzed to detect levels and/or locations of one or more biological compounds which are associated with abnormal breast tissue. In an example, changes in light caused by passage through breast tissue can be analyzed to detect levels and/or locations of deoxyhemoglobin. In an example, changes in light caused by passage through breast tissue can be analyzed to detect levels and/or locations of lipid content. In an example, changes in light caused by passage through breast tissue can be analyzed to detect levels and/or locations of water. In an example, changes in light caused by passage through breast tissue can be analyzed to detect levels and/or locations of oxygenated hemoglobin.

In an example, changes in light intensity or spectral distribution caused by passage through breast tissue can be analyzed to detect levels and/or locations of deoxyhemoglobin. In an example, changes in light intensity or spectral distribution caused by passage through breast tissue can be analyzed to detect levels and/or locations of lipid content. In an example, changes in light intensity or spectral distribution caused by passage through breast tissue can be analyzed to detect levels and/or locations of water. In an example, changes in light intensity or spectral distribution caused by passage through breast tissue can be analyzed to detect levels and/or locations of oxygenated hemoglobin.

In an example, spectroscopic analysis of light transmitted through breast tissue can detect spectral troughs caused by absorption of light by unusual concentrations of collagen, hemoglobin, deoxyhemoglobin, oxyhemoglobin, lipids, and/or oxygen. In an example, light which has been transmitted through breast tissue and received by light receivers can be analyzed to identify the presence, composition, shape, size, and/or location of abnormal tissue in the breast based on analysis of one or more of the following biometric markers: hemoglobin, deoxyhemoglobin, and/or oxyhemoglobin, lipids composition, collagen composition, lymphatics and/or lymphamatics, oxygen saturation, water composition, extracellular matrix, and vasculature configuration and/or sprouting. In an example, light which has been transmitted through breast tissue and received by light receivers can be analyzed to identify the presence, composition, shape, size, and/or location of abnormal tissue in the breast based on analysis of changes in one or more of the following biometric markers: hemoglobin, deoxyhemoglobin, and/or oxyhemoglobin, lipids composition, collagen composition, lymphatics and/or lymphamatics, oxygen saturation, water composition, extracellular matrix, and vasculature configuration and/or sprouting.

In an example, the intensity of light emitted from light emitters and received by light receivers can be analyzed to detect abnormal breast tissue. In an example, the intensity of light emitted from light emitters and received by light receivers can be analyzed to image breast tissue. In an example, the intensity of light emitted from light emitters and received by light receivers can be analyzed to evaluate the size, shape, density, and/or location of abnormal breast tissue. In an example, the intensity of light emitted from light emitters and received by light receivers can be analyzed to evaluate the molecular composition of breast tissue and detect abnormal breast tissue. In an example, the intensity of light emitted from light emitters and received by light receivers can be analyzed to detect tumors. In an example, the intensity of light emitted from light emitters and received by light receivers can be analyzed to detect malignancies.

In an example, changes in the intensity of light emitted from light emitters and received by light receivers which are caused by passage of the light through breast tissue can be analyzed to detect abnormal breast tissue. In an example, changes in the intensity of light emitted from light emitters and received by light receivers which are caused by passage of the light through breast tissue can be analyzed to image breast tissue. In an example, changes in the intensity of light emitted from light emitters and received by light receivers which are caused by passage of the light through breast tissue can be analyzed to evaluate the size, shape, density, and/or location of abnormal breast tissue.

In an example, changes in the intensity of light emitted from light emitters and received by light receivers which are caused by passage of the light through breast tissue can be analyzed to evaluate the molecular composition of breast tissue and detect abnormal breast tissue. In an example, changes in the intensity of light emitted from light emitters and received by light receivers which are caused by passage of the light through breast tissue can be analyzed to detect tumors. In an example, changes in the intensity of light emitted from light emitters and received by light receivers which are caused by passage of the light through breast tissue can be analyzed to detect malignancies.

In an example, the spectral distribution of light emitted from light emitters and received by light receivers can be analyzed to detect abnormal breast tissue. In an example, the spectral distribution of light emitted from light emitters and received by light receivers can be analyzed to image breast tissue. In an example, the spectral distribution of light emitted from light emitters and received by light receivers can be analyzed to evaluate the size, shape, density, and/or location of abnormal breast tissue.

In an example, changes in the spectral distribution of light emitted from light emitters and received by light receivers which are caused by passage of the light through breast tissue can be analyzed to detect abnormal breast tissue. In an example, changes in the spectral distribution of light emitted from light emitters and received by light receivers which are caused by passage of the light through breast tissue can be analyzed to image breast tissue. In an example, changes in the spectral distribution of light emitted from light emitters and received by light receivers which are caused by passage of the light through breast tissue can be analyzed to evaluate the size, shape, density, and/or location of abnormal breast tissue.

In an example, changes in the spectral distribution of light emitted from light emitters and received by light receivers which are caused by passage of the light through breast tissue can be analyzed to evaluate the molecular composition of breast tissue and detect abnormal breast tissue. In an example, changes in the spectral distribution of light emitted from light emitters and received by light receivers which are caused by passage of the light through breast tissue can be analyzed to detect tumors. In an example, changes in the spectral distribution of light emitted from light emitters and received by light receivers which are caused by passage of the light through breast tissue can be analyzed to detect malignancies.

In an example, light from a light emitter which has been transmitted through breast tissue and received by a light receiver can be spectroscopically analyzed to detect the presence, composition, shape, size, and/or location of abnormal breast tissue. In an example, changes in the spectral distribution and/or spectrum of transmitted light can be analyzed to detect the presence, composition, shape, size, and/or location of abnormal breast tissue. In an example, spectral changes of light transmitted between a plurality of pairs of light emitters and light receivers can be collectively analyzed (e.g. triangulated) in order to identify the likely location of abnormal breast tissue.

In an example, the direction of light emitted from light emitters and received by light receivers can be analyzed to detect abnormal breast tissue. In an example, the direction of light emitted from light emitters and received by light receivers can be analyzed to image breast tissue. In an example, the direction of light emitted from light emitters and received by light receivers can be analyzed to evaluate the size, shape, density, and/or location of abnormal breast tissue.

In an example, changes in the direction of light emitted from light emitters and received by light receivers which are caused by passage of the light through breast tissue can be analyzed to detect abnormal breast tissue. In an example, changes in the direction of light emitted from light emitters and received by light receivers which are caused by passage of the light through breast tissue can be analyzed to image breast tissue. In an example, changes in the direction of light emitted from light emitters and received by light receivers which are caused by passage of the light through breast tissue can be analyzed to evaluate the size, shape, density, and/or location of abnormal breast tissue.

In an example, changes in the direction of light emitted from light emitters and received by light receivers which are caused by passage of the light through breast tissue can be analyzed to evaluate the molecular composition of breast tissue and detect abnormal breast tissue. In an example, changes in the direction of light emitted from light emitters and received by light receivers which are caused by passage of the light through breast tissue can be analyzed to detect tumors. In an example, changes in the direction of light emitted from light emitters and received by light receivers which are caused by passage of the light through breast tissue can be analyzed to detect malignancies.

In an example, the timing of light emitted from light emitters and received by light receivers can be analyzed to detect abnormal breast tissue. In an example, the timing of light emitted from light emitters and received by light receivers can be analyzed to image breast tissue. In an example, the timing of light emitted from light emitters and received by light receivers can be analyzed to evaluate the size, shape, density, and/or location of abnormal breast tissue.

In an example, changes in the timing of light emitted from light emitters and received by light receivers which are caused by passage of the light through breast tissue can be analyzed to detect abnormal breast tissue. In an example, changes in the timing of light emitted from light emitters and received by light receivers which are caused by passage of the light through breast tissue can be analyzed to image breast tissue. In an example, changes in the timing of light emitted from light emitters and received by light receivers which are caused by passage of the light through breast tissue can be analyzed to evaluate the size, shape, density, and/or location of abnormal breast tissue.

In an example, changes in the timing of light emitted from light emitters and received by light receivers which are caused by passage of the light through breast tissue can be analyzed to evaluate the molecular composition of breast tissue and detect abnormal breast tissue. In an example, changes in the timing of light emitted from light emitters and received by light receivers which are caused by passage of the light through breast tissue can be analyzed to detect tumors. In an example, changes in the timing of light emitted from light emitters and received by light receivers which are caused by passage of the light through breast tissue can be analyzed to detect malignancies.

In an example, light from light emitters which has passed through breast tissues can be analyzed using diffuse optical imaging. In an example, light from light emitters which has passed through breast tissues can be analyzed using near-infrared spectroscopy. In an example, light from light emitters which has passed through breast tissues can be analyzed using diffuse optical tomography. In an example, light from light emitters which has passed through breast tissues can be analyzed using time of flight diffuse optical tomography. In an example, light from light emitters which has passed through breast tissues can be analyzed using Raman scattering.

In an example, this device can use diffuse optical imaging to analyze the molecular composition of breast tissue, detect abnormal breast tissue, evaluate the size and shape of abnormal breast tissue, identify selected biometric parameters in breast tissue, identify the location of abnormal breast tissue, and/or image breast tissue. In an example, this device can use near-infrared spectroscopy to analyze the molecular composition of breast tissue, detect abnormal breast tissue, evaluate the size and shape of abnormal breast tissue, identify selected biometric parameters in breast tissue, identify the location of abnormal breast tissue, and/or image breast tissue.

In an example, this device can use diffuse optical tomography to analyze the molecular composition of breast tissue, detect abnormal breast tissue, evaluate the size and shape of abnormal breast tissue, identify selected biometric parameters in breast tissue, identify the location of abnormal breast tissue, and/or image breast tissue. In an example, this device can use time of flight diffuse optical tomography to analyze the molecular composition of breast tissue, detect abnormal breast tissue, evaluate the size and shape of abnormal breast tissue, identify selected biometric parameters in breast tissue, identify the location of abnormal breast tissue, and/or image breast tissue.

In an example, this device can use Raman scattering to analyze the molecular composition of breast tissue, detect abnormal breast tissue, evaluate the size and shape of abnormal breast tissue, identify selected biometric parameters in breast tissue, identify the location of abnormal breast tissue, and/or image breast tissue. In an example, this device can use spectroscopic analysis to analyze the molecular composition of breast tissue, detect abnormal breast tissue, evaluate the size and shape of abnormal breast tissue, identify selected biometric parameters in breast tissue, identify the location of abnormal breast tissue, and/or image breast tissue.

In an example, light which has been transmitted through breast tissue and received by light receivers can be analyzed using one or more methods selected from the group consisting of: Time Reversal Optical Tomography (TROT), changes in the frequency spectrum of light transmitted through a breast, Diffuse Optical Imaging (DOI), Diffuse Optical Tomography (DOT), spectroscopic analysis, analysis of absorption and/or scattering of light transmitted through a breast, near-infrared spectroscopy, changes in the intensity or amplitude of light transmitted through a breast, changes in the phase of light transmitted through a breast, Diffuse Correlation Spectroscopy (DCS), Carlavian Curve Analysis (CCA), machine learning, neural network analysis, broadband spectroscopy, and/or changes in the spectral distribution of light transmitted through a breast.

In various examples, light which has been transmitted through breast tissue and received by light receivers can be analyzed to: create an image (e.g. scan or map) which shows variation in breast tissue density; identify the location of abnormal breast tissue; create an image (e.g. scan or map) which shows abnormal tissue within a breast; identify the molecular and/or cellular composition of the breast; identify the presence of abnormal breast tissue; identify the shape of abnormal breast tissue; create an image (e.g. scan or map) which shows the size of abnormal tissue within a breast; identify the structure of abnormal breast tissue; create an image (e.g. scan or map) which shows the structure of abnormal tissue within a breast; create an image (e.g. scan or map) which variation in breast tissue composition; create a three-dimensional image of a breast; create an image (e.g. scan or map) which shows blood flow within a breast; identify the composition of abnormal breast tissue; create an image (e.g. scan or map) which shows metabolic processes within a breast; create an image (e.g. scan or map) which shows the shape of abnormal tissue within a breast; create a two-dimensional image of a breast; and/or create an image (e.g. scan or map) which shows the concentrations of a substance within a breast.

In an example, changes and/or differences in the intensity and/or spectral distribution of light received by light receivers after traveling through breast tissue along different light path vectors and/or between different pairs of light emitters and light receivers can be analyzed to create a (3D) image which shows (variation in) breast tissue density and/or composition. In an example, changes and/or differences in the intensity and/or spectral distribution of light received by light receivers after traveling through breast tissue can be analyzed to create a (3D) image which shows (variation in) breast tissue density and/or composition. In an example, changes and/or differences in the intensity of light received by light receivers after traveling through breast tissue along different light path vectors and/or between different pairs of light emitters and light receivers can be analyzed to create a (3D) image which shows (variation in) breast tissue density. In an example, changes and/or differences in the spectrum of light received by light receivers after traveling through breast tissue along different light path vectors and/or between different pairs of light emitters and light receivers can be analyzed to create a (3D) image which shows (variation in) breast tissue composition. In an example, changes and/or differences in the spectrum of light received by light receivers after traveling through breast tissue can be analyzed to identify (potentially) abnormal tissue.

In an example, a device and/or system can further comprise one or more other components selected from the group consisting of: a power source, a data processor, a wireless data transmitter, and a wireless data receiver. In an example, these other components can be integrated into a smart bra. In an example, some of these components can be integrated into a smart bra and others can be located remotely. In an example, a system can comprise a local power source, local data processor, local data transmitter, remote data receiver, and remote data processor.

In an example, this device (or a system embodiment of it with multiple components) can further comprise electronic or mechanical components selected from the group consisting of: an electronics housing, a data processor, a mirror, an air impeller, a data receiver, an air pump, an air reservoir, an electromagnetic actuator, a liquid pump, a liquid reservoir, a micromirror array, a battery, a data transmitter, a motion sensor, a prism, a lens, a light receiver, and a light emitter. In an example, one or more of these components can be located on the back strap of a smart bra. In an example, one or more of these components can be removably connected to a smart bra. A system can comprise a smart bra in wireless communication with a cell phone, smart watch, smart glasses, tablet computer, or laptop computer.

In an example, a power source can be a battery. In an example, a power source which powers light emitters and receivers can be an integral part of a smart bra. In an example, a power source which powers light emitters and receivers can be located on the posterior portion of a smart bra. In an example, a power source which powers light emitters and receivers can be located on the back strap of a smart bra.

In an example, this device can further comprise a data processor which is an integral part of a smart bra. In an example, this device can further comprise a data processor which is located on the posterior portion of a smart bra. In an example, this device can further comprise a data processor which is located on the back strap of a smart bra. In an example, a data processor can control the light emitters and light receivers. In an example, a data processor can receive data from the light receivers.

In an example, a system can comprise a local data processor which is part of a smart bra and a remote data processor which receives data from the local data processor. In an example, a system can comprise a local data processor and data transmitter which are part of a smart bra and a remote data processor which receives data from the local data processor via the data transmitter. In an example, analysis of changes in light intensity and/or spectral distribution can be analyzed in the remote data processor.

In an example, a separate data processor can be in a wearable device (e.g. a smart watch), a mobile device (e.g. a cell phone), or a remote server (e.g. in a healthcare provider's server and/or cloud storage). In an example, data from this device can be (wirelessly) transmitted to a data processor in a different wearable device (e.g. a smart watch), a handheld device (e.g. a cell phone), or a remote server (e.g. in a healthcare provider's server and/or cloud storage). In an example, data from light receivers this device can be transmitted to a separate data processor for spectroscopic analysis to identify changes in breast tissue composition and/or help identify abnormal breast tissue.

In an example, a device can further comprise a liquid pump on the back strap of the bra, wherein the liquid pump is manually operated to expand one or more expandable chambers to improve the fit of optical components on the contour of a breast. In an example, a device can include an air pump on the back strap of the bra, wherein the air pump is manually operated to inflate one or more expandable chambers to improve the fit of optical components relative to the contour of a breast. In an example, an air pump can be operated by the person pressing the pump with their hand. In an example, a liquid pump can be automatically operated by an impellor which is rotated by an electromagnetic motor. In an example, an air pump can be automatically operated by an air impeller which is rotated by electromagnetic motor.

In an example, a wearable device for analyzing breast tissue can comprise: a cup worn on a person's breast; a first expandable chamber in a first half of the cup, wherein the first half is on a first side of an anterior-to-posterior virtual plane intersecting the cup; a second expandable chamber in a second half of the cup, wherein the second half is on a second side of the anterior-to-posterior virtual plane intersecting the cup; a plurality of light emitters in the first half of the cup; and a plurality of light receivers in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

A wearable device for analyzing breast tissue can comprise: a cup which is worn on (e.g. on and/or over) a person's breast; a first expandable chamber inside (e.g. within the concavity of) the cup; a second expandable chamber inside (e.g. within the concavity of) the cup; wherein there is a portion of the breast between the first expandable chamber and the second expandable chamber, wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein the device is changed from the first configuration to the second configuration by the first expandable chamber and the second expandable chamber by pumping a gas or liquid into the first expandable chamber and the second expandable chamber, and wherein the portion of the breast is compressed between the first expandable chamber and the second expandable chamber in the second configuration; a plurality of light emitters inside (e.g. within the concavity of) the cup; and a plurality of light receivers inside (e.g. within the concavity of) the cup; wherein light from light emitters in the plurality of light emitters is received by light receivers in the plurality of light receivers after the light has passed through the portion of the breast, wherein light received by the light receivers is evaluated to analyze and/or image breast tissue, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein there is an anterior-to-posterior virtual plane which intersects the cup, wherein the virtual plane is between the first expandable chamber and the second expandable chamber in the first configuration, and wherein the virtual plane is between the plurality of light emitters and the plurality of light receivers in the first configuration.

In an example, a wearable device for analyzing breast tissue can comprise: a cup which is configured to be worn on a person's breast; a first expandable chamber inside (the concavity of) the cup; a second expandable chamber inside (the concavity of) the cup; a plurality of light emitters inside (the concavity of) the cup; and a plurality of light receivers inside (the concavity of) the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein the device is changed from the first configuration to the second configuration by filling the first expandable chamber and the second expandable chamber with a gas or liquid, wherein a portion of the breast is between the first expandable chamber and the second expandable chamber, wherein the portion of the breast is compressed in the second configuration, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein light from light emitters in the plurality of light emitters is received by light receivers in the plurality of light receivers after the light has passed through the portion of the breast wherein analysis of light received by the light receivers is used to analyze breast tissue, and wherein there is an anterior-to-posterior virtual plane which intersects the cup, wherein the virtual plane is between the first expandable chamber and the second expandable chamber in at least the first configuration, wherein the virtual plane is between the plurality of light emitters and the plurality of light receivers in at least the first configuration.

In an example, a wearable device for analyzing breast tissue can comprise: a cup worn on a person's breast; a first expandable chamber on (e.g. on or inside) a first half of the cup divided by a diagonal plane (e.g. an anterior-to-posterior plane intersecting the 315-degree latitude and 135-degree latitude lines); a second expandable chamber on (e.g. on or inside) a second (the opposite) half of the cup divided by the diagonal plane; a plurality of light emitters on (e.g. on or inside) the first half of the cup; and a plurality of light receivers on (e.g. on or inside) the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein a portion of the breast is between the first expandable chamber and the second expandable chamber, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein light from light emitters in the plurality of light emitters is received by light receivers in the plurality of light receivers after the light has passed through the portion of the breast, and wherein analysis of light received by the light receivers is used to analyze breast tissue.

In an example, a wearable device for analyzing breast tissue can comprise: a cup worn on a person's breast; a first expandable chamber on (e.g. on or inside) a first half of the cup divided by a diagonal plane (e.g. an anterior-to-posterior plane intersecting the 45-degree latitude and 225-degree latitude lines); a second expandable chamber on (e.g. on or inside) a second (the opposite) half of the cup divided by the diagonal plane; a plurality of light emitters on (e.g. on or inside) the first half of the cup; and a plurality of light receivers on (e.g. on or inside) the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein a portion of the breast is between the first expandable chamber and the second expandable chamber, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein light from light emitters in the plurality of light emitters is received by light receivers in the plurality of light receivers after the light has passed through the portion of the breast, and wherein analysis of light received by the light receivers is used to analyze breast tissue.

In an example, a wearable device for analyzing breast tissue can comprise: a cup worn on a person's breast; a first expandable chamber on (e.g. on or inside) a first half (e.g. the lower half) of the cup; a second expandable chamber on (e.g. on or inside) a second half (e.g. the upper half) of the cup; a plurality of light emitters on (e.g. on or inside) the first half of the cup; and a plurality of light receivers on (e.g. on or inside) the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein a portion of the breast is between the first expandable chamber and the second expandable chamber, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein light from light emitters in the plurality of light emitters is received by light receivers in the plurality of light receivers after the light has passed through the portion of the breast, and wherein analysis of light received by the light receivers is used to analyze breast tissue.

In an example, a wearable device for analyzing breast tissue can comprise: a cup worn on a person's breast; a first expandable chamber in the cup; a second expandable chamber in the cup; a plurality of light emitters in the cup; and a plurality of light receivers in the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein a portion of the breast is between the first expandable chamber and the second expandable chamber, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein light from light emitters in the plurality of light emitters is received by light receivers in the plurality of light receivers after the light has passed through the portion of the breast, and wherein analysis of light received by the light receivers is used to analyze breast tissue.

In an example, a wearable device for analyzing breast tissue can comprise: a cup worn on a person's breast; a first expandable chamber on (e.g. on or inside) a first side (e.g. the right side) of the cup; a second expandable chamber on (e.g. on or inside) a second side (e.g. the left side) of the cup; a plurality of light emitters on (e.g. on or inside) the first side of the cup; and a plurality of light receivers on the second side of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein a portion of the breast is between the first expandable chamber and the second expandable chamber, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein light from light emitters in the plurality of light emitters is received by light receivers in the plurality of light receivers after the light has passed through the portion of the breast, and wherein analysis of light received by the light receivers is used to analyze breast tissue.

A wearable device for analyzing breast tissue can comprise: a cup which is worn on (e.g. on and/or over) a person's breast; a first expandable chamber inside (e.g. within the concavity of) the cup; a second expandable chamber inside (e.g. within the concavity of) the cup; wherein there is a portion of the breast between the first expandable chamber and the second expandable chamber, wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein the device is changed from the first configuration to the second configuration by the first expandable chamber and the second expandable chamber by pumping a gas or liquid into the first expandable chamber and the second expandable chamber, and wherein the portion of the breast is compressed between the first expandable chamber and the second expandable chamber in the second configuration; a plurality of light emitters inside (e.g. within the concavity of) the cup; and a plurality of light receivers inside (e.g. within the concavity of) the cup; wherein light from light emitters in the plurality of light emitters is received by light receivers in the plurality of light receivers after the light has passed through the portion of the breast, wherein light received by the light receivers is evaluated to analyze and/or image breast tissue, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein there is an anterior-to-posterior virtual plane which intersects the apex of the cup, wherein the virtual plane is between the first expandable chamber and the second expandable chamber in the first configuration, and wherein the virtual plane is between the plurality of light emitters and the plurality of light receivers in the first configuration.

In an example, a wearable device for analyzing breast tissue can comprise: a cup which is worn on a person's breast; a first expandable chamber within the cup; a second expandable chamber within the cup; wherein there is a portion of the breast between the first expandable chamber and the second expandable chamber, wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein the device is changed from the first configuration to the second configuration by inflating the first expandable chamber and the second expandable chamber, and wherein the portion of the breast is compressed in the second configuration; a plurality of light emitters within the cup; and a plurality of light receivers within the cup; wherein light from light emitters in the plurality of light emitters is received by light receivers in the plurality of light receivers after the light has passed through the portion of the breast, wherein light received by the light receivers is analyzed to get information about abnormal breast tissue, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein there is an anterior-to-posterior virtual plane which intersects the cup, wherein the virtual plane is between the first expandable chamber and the second expandable chamber in the first configuration, and wherein the virtual plane is between the plurality of light emitters and the plurality of light receivers in the first configuration.

In an example, a wearable device for detection and/or imaging of abnormal breast tissue can comprise: a cup which is worn on a person's breast; a first expandable chamber within the cup, wherein the first expandable chamber is expanded by being filled with a gas or liquid; a plurality of light emitters within the cup which are moved by expansion of the first expandable chamber; a second expandable chamber within the cup, wherein the second expandable chamber is expanded by being filled with a gas or liquid; and a plurality of light receivers within the cup which are moved by expansion of the second expandable chamber; wherein there is an anterior-to-posterior virtual plane which intersects the cup, wherein the virtual plane is between the first expandable chamber and the second expandable chamber, wherein the virtual plane is between the plurality of light emitters and the plurality of light receivers, wherein a portion of the breast is between the first expandable chamber and the second expandable chamber, wherein the portion of the breast is compressed when the first expandable chamber and the second expandable chamber are expanded, wherein light from light emitters in the plurality of light emitters is received by light receivers in the plurality of light receivers after the light has passed through the portion of the breast, and wherein light received by the light receivers is analyzed to detect and/or image abnormal breast tissue.

In an example, a wearable device for analyzing breast tissue can comprise: a cup which is worn on a person's breast; a first expandable chamber inside (the concavity of)

the cup; a second expandable chamber inside (the concavity of) the cup; wherein a portion of the breast is between the first expandable chamber and the second expandable chamber, wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein the device is changed from the first configuration to the second configuration by filling the first expandable chamber and the second expandable chamber with a gas or liquid, and wherein the portion of the breast is compressed in the second configuration; a plurality of light emitters inside (the concavity of) the cup; and a plurality of light receivers inside (the concavity of) the cup; wherein light from light emitters in the plurality of light emitters is received by light receivers in the plurality of light receivers after the light has passed through the portion of the breast, wherein analysis of light received by the light receivers is used to analyze breast tissue, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein there is an anterior-to-posterior virtual plane which intersects the cup, wherein the virtual plane is between the first expandable chamber and the second expandable chamber in at least the first configuration, and wherein the virtual plane is between the plurality of light emitters and the plurality of light receivers in at least the first configuration.

In an example, a wearable device for analyzing breast tissue can comprise: a cup worn on a person's breast; a first expandable chamber in a first half of the cup, wherein the first half is on a first side of an anterior-to-posterior virtual plane intersecting the cup; a second expandable chamber in a second half of the cup, wherein the second half is on a second side of the anterior-to-posterior virtual plane intersecting the cup; a plurality of light emitters in the first half of the cup; and a plurality of light receivers in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

In an example, a wearable device for analyzing breast tissue can comprise: a cup which is configured to be worn on a person's breast; a first expandable chamber in a first portion of the cup, wherein the first portion is on a first side of an anterior-to-posterior virtual plane intersecting the cup; a second expandable chamber in a second portion of the cup, wherein the second portion is on a second side of the anterior-to-posterior virtual plane intersecting the cup; a plurality of light emitters in the first portion of the cup; and a plurality of light receivers in the second portion of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

In an example, the plane can be parallel to 0-degree and 180-degree latitudinal lines of the cup. In an example, the first portion of the cup can be to the right of the plane and the second portion of the cup can be to the left of the plane. In an example, the first portion of the cup can be to the left of the plane and the second portion of the cup can be to the right of the plane. In an example, the plane can be parallel to 270-degree and 90-degree latitudinal lines of the cup. In an example, the first portion of the cup can be below the plane and the second portion of the cup can be above the plane. In an example, the first portion of the cup can be above the plane and the second portion of the cup can be below the plane.

In an example, the plane can be parallel to 315-degree and 135-degree latitudinal lines of the cup. In an example, the first portion of the cup can be to the lower left of the plane and the second portion of the cup can be to the upper right of the plane. In an example, the first portion of the cup can be to the upper right of the plane and the second portion of the cup can be to the lower left of the plane. In an example, the plane can be parallel to 225-degree and 45-degree latitudinal lines of the cup. In an example, the first portion of the cup can be to the lower right of the plane and the second portion of the cup can be to the upper left of the plane. In an example, the first portion of the cup can be to the upper left of the plane and the second portion of the cup can be to the lower right of the plane.

In an example, the plurality of light emitters are no closer than ¼ inch from the plane and the plurality of light receivers are no closer than ¼ inch from the plane. In an example, the plurality of light emitters are no closer than ½ inch from the plane and the plurality of light receivers are no closer than ½ inch from the plane. In an example, the plurality of light emitters are no closer than 1 inch from the plane and the plurality of light receivers are no closer than 1 inch from the plane.

In an example, the first expandable chamber and the second expandable chamber can be expanded by being filled with a gas. In an example, the first expandable chamber and the second expandable chamber can be expanded by being filled with a liquid. In an example, the wearable device can be a bra. In an example, the wearable device can be inserted into a bra cup.

Figure 2:
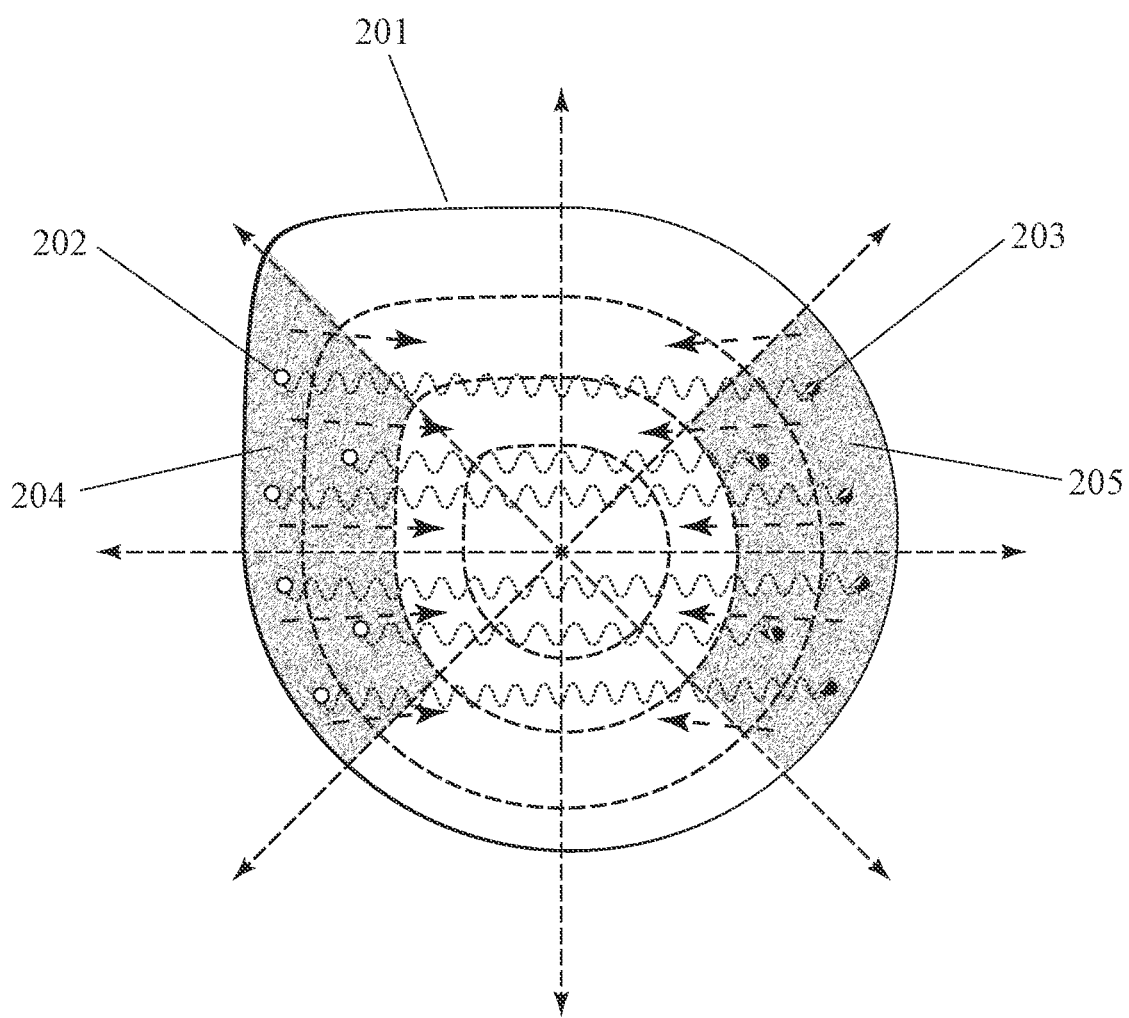
FIG. 2 shows a wearable bra cup for optical analysis of breast tissue with expandable chambers, and light emitters and receivers, to the right and left of a vertical plane.

FIG. 2 shows a coronal (e.g. frontal) cross-sectional view of an example of a wearable device for analyzing breast tissue comprising: a cup which is configured to be worn on a person's breast; a first expandable chamber in a first portion of the cup, wherein the first portion is on a first side of an anterior-to-posterior virtual plane intersecting the cup; a second expandable chamber in a second portion of the cup, wherein the second portion is on a second side of the anterior-to-posterior virtual plane intersecting the cup; a plurality of light emitters in the first portion of the cup; and a plurality of light receivers in the second portion of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

FIG. 2 also shows a coronal (e.g. frontal) cross-sectional view of an example of a wearable device for analyzing breast tissue comprising: a cup worn on a person's breast; a first expandable chamber in a first half of the cup, wherein the first half is on a first side of an anterior-to-posterior virtual plane intersecting the cup; a second expandable chamber in a second half of the cup, wherein the second half is on a second side of the anterior-to-posterior virtual plane intersecting the cup; a plurality of light emitters in the first half of the cup; and a plurality of light receivers in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

With respect to specific components, FIG. 2 shows an example of a wearable device for analyzing breast tissue comprising: a cup 201 worn on a person's breast; a first expandable chamber 204 in a first half of the cup, wherein the first half is on a first side of an anterior-to-posterior virtual plane intersecting the cup; a second expandable chamber 205 in a second half of the cup, wherein the second half is on a second side of the anterior-to-posterior virtual plane intersecting the cup; a plurality of light emitters (including light emitter 202) in the first half of the cup; and a plurality of light receivers (including light receiver 203) in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters (shown in the figure by undulating dotted-line waves) in the plurality of light emitters is received by light receivers in the plurality of light receivers after the light has passed through the portion of the breast, and wherein analysis of light received by the light receivers is used to analyze breast tissue.

In this example, the anterior-to-posterior virtual plane which divides the cup into two sides intersects the 0-degree latitudinal and 180-degree latitudinal lines. In this example, the first expandable chamber and the light emitters are (clockwise) between the 225-degree latitudinal and 315-degree latitudinal lines and between the 90-degree longitudinal and 30-degree longitudinal lines. In this example, the second expandable chamber and the light receivers are (clockwise) between the 45-degree latitudinal and 135-degree latitudinal lines and between the 90-degree longitudinal and 30-degree longitudinal lines. In an example, a symmetric variation of this example can be created by reflecting the expandable chambers and optical components across the virtual plane. In this example, a cup for a person's right breast is shown. In an example, a symmetric variation can be used for a cup on a breast on the other side (e.g. right vs. left) of a person's chest. Example variations discussed elsewhere in this disclosure or in priority-linked disclosures can be applied to this example where relevant.

Figure 3:
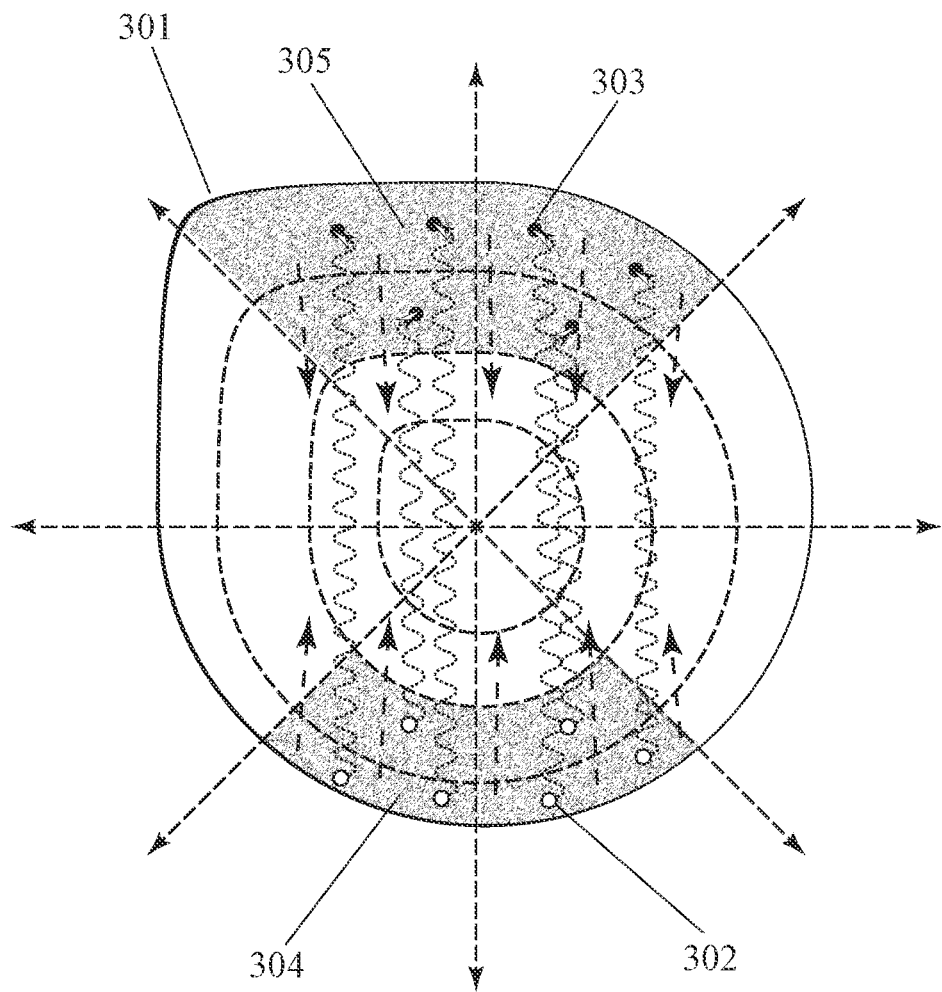
FIG. 3 shows a wearable bra cup for optical analysis of breast tissue with expandable chambers, and light emitters and receivers, below and above a horizontal plane.

FIG. 3 shows a coronal (e.g. frontal) cross-sectional view of an example of a wearable device for analyzing breast tissue comprising: a cup which is configured to be worn on a person's breast; a first expandable chamber in a first portion of the cup, wherein the first portion is on a first side of an anterior-to-posterior virtual plane intersecting the cup; a second expandable chamber in a second portion of the cup, wherein the second portion is on a second side of the anterior-to-posterior virtual plane intersecting the cup; a plurality of light emitters in the first portion of the cup; and a plurality of light receivers in the second portion of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

FIG. 3 also shows a coronal (e.g. frontal) cross-sectional view of an example of a wearable device for analyzing breast tissue comprising: a cup worn on a person's breast; a first expandable chamber in a first half of the cup, wherein the first half is on a first side of an anterior-to-posterior virtual plane intersecting the cup; a second expandable chamber in a second half of the cup, wherein the second half is on a second side of the anterior-to-posterior virtual plane intersecting the cup; a plurality of light emitters in the first half of the cup; and a plurality of light receivers in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

With respect to specific components, FIG. 3 shows an example of a wearable device for analyzing breast tissue comprising: a cup 301 worn on a person's breast; a first expandable chamber 304 in a first half of the cup, wherein the first half is on a first side of an anterior-to-posterior virtual plane intersecting the cup; a second expandable chamber 305 in a second half of the cup, wherein the second half is on a second side of the anterior-to-posterior virtual plane intersecting the cup; a plurality of light emitters (including light emitter 302) in the first half of the cup; and a plurality of light receivers (including light receiver 303) in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters (shown in the figure by undulating dotted-line waves) in the plurality of light emitters is received by light receivers in the plurality of light receivers after the light has passed through the portion of the breast, and wherein analysis of light received by the light receivers is used to analyze breast tissue.

In this example, the anterior-to-posterior virtual plane which divides the cup into two sides intersects the 270-degree latitudinal and 90-degree latitudinal lines. In this example, the first expandable chamber and the light emitters are (clockwise) between the 135-degree latitudinal and 225-degree latitudinal lines and between the 90-degree longitudinal and 30-degree longitudinal lines. In this example, the second expandable chamber and the light receivers are (clockwise) between the 315-degree latitudinal and 45-degree latitudinal lines and between the 90-degree longitudinal and 30-degree longitudinal lines. In an example, a symmetric variation of this example can be created by reflecting the expandable chambers and optical components across the virtual plane. In this example, a cup for a person's right breast is shown. In an example, a symmetric variation can be used for a cup on a breast on the other side (e.g. right vs. left) of a person's chest. Example variations discussed elsewhere in this disclosure or in priority-linked disclosures can be applied to this example where relevant.

Figure 4:
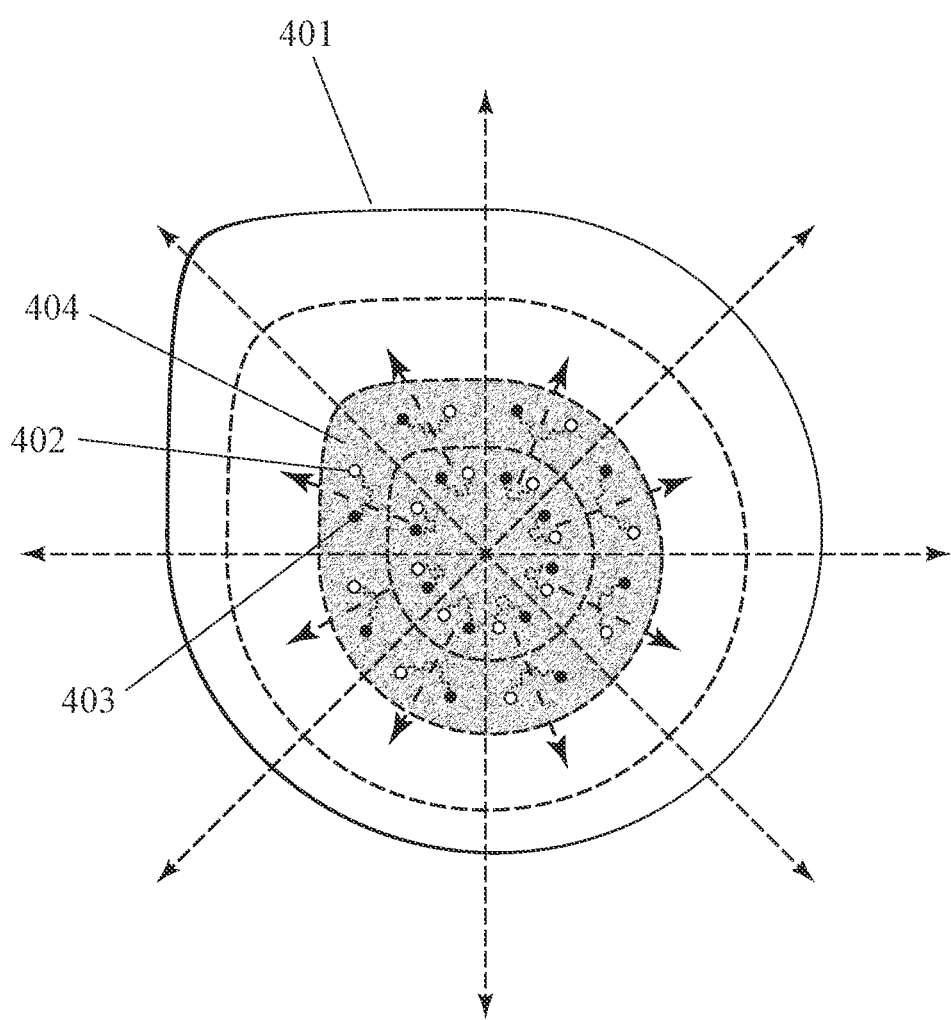
FIG. 4 shows a wearable bra cup for optical analysis of breast tissue with an expandable chamber, light emitters, and light receivers on a central portion of the cup.

FIG. 4 shows a coronal (e.g. frontal) cross-sectional view of an example of a wearable device for analyzing breast tissue comprising: a cup worn on a person's breast; an expandable chamber in a central region of the cup; and a plurality of light emitters and a plurality of light receivers in the central region of the cup; wherein light from light emitters in the plurality of light emitters is received by light receivers in the plurality of light receivers after the light has been reflected by breast tissue, and wherein analysis of light received by the light receivers is used to analyze breast tissue.

With respect to specific components, FIG. 4 shows a coronal (e.g. frontal) cross-sectional view of an example of a wearable device for analyzing breast tissue comprising: a cup 401 worn on a person's breast; an expandable chamber 404 in a central region of the cup; and a plurality of light emitters (including light emitter 402) and a plurality of light receivers (including light receiver 403) in the central region of the cup; wherein light from light emitters in the plurality of light emitters is received by light receivers in the plurality of light receivers after the light has been reflected by breast tissue, and wherein analysis of light received by the light receivers is used to analyze breast tissue. In this example, the central region of the cup is between the apex of the cup and the 30-degree longitudinal line. Example variations discussed elsewhere in this disclosure or in priority-linked disclosures can be applied to this example where relevant.

Figure 5:
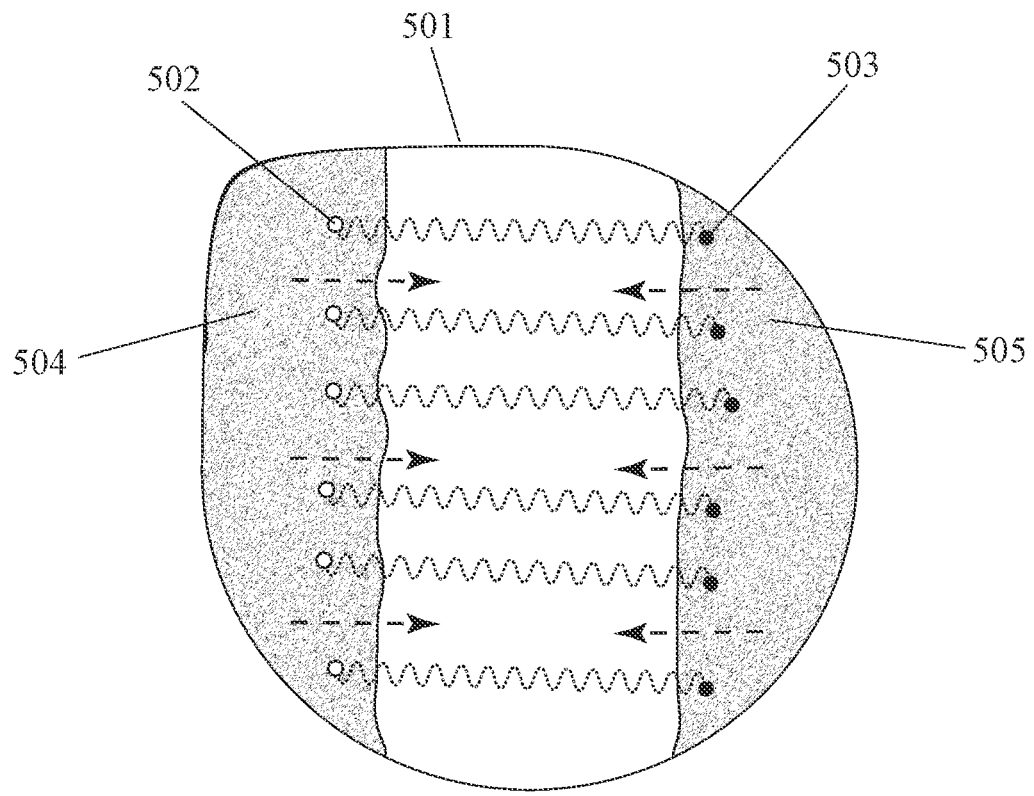
FIG. 5 shows a wearable bra cup for optical analysis of breast tissue with expandable chambers, and light emitters and receivers, on right and left portions of the cup.

FIG. 5 shows a coronal (e.g. frontal) cross-sectional view of an example of a wearable device for analyzing breast tissue comprising: a cup which is configured to be worn on a person's breast; a first expandable chamber in a first portion of the cup, wherein the first portion is on a first side of an anterior-to-posterior virtual plane intersecting the cup; a second expandable chamber in a second portion of the cup, wherein the second portion is on a second side of the anterior-to-posterior virtual plane intersecting the cup; a plurality of light emitters in the first portion of the cup; and a plurality of light receivers in the second portion of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

FIG. 5 also shows a coronal (e.g. frontal) cross-sectional view of an example of a wearable device for analyzing breast tissue comprising: a cup worn on a person's breast; a first expandable chamber in a first half of the cup, wherein the first half is on a first side of an anterior-to-posterior virtual plane intersecting the cup; a second expandable chamber in a second half of the cup, wherein the second half is on a second side of the anterior-to-posterior virtual plane intersecting the cup; a plurality of light emitters in the first half of the cup; and a plurality of light receivers in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

With respect to specific components, FIG. 5 shows an example of a wearable device for analyzing breast tissue comprising: a cup 501 worn on a person's breast; a first expandable chamber 504 in a first half of the cup, wherein the first half is on a first side of an anterior-to-posterior virtual plane intersecting the cup; a second expandable chamber 505 in a second half of the cup, wherein the second half is on a second side of the anterior-to-posterior virtual plane intersecting the cup; a plurality of light emitters (including light emitter 502) in the first half of the cup; and a plurality of light receivers (including light receiver 503) in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters (shown in the figure by undulating dotted-line waves) in the plurality of light emitters is received by light receivers in the plurality of light receivers after the light has passed through the portion of the breast, and wherein analysis of light received by the light receivers is used to analyze breast tissue.

In this example, the anterior-to-posterior virtual plane which divides the cup into two sides intersects the 0-degree latitudinal and 180-degree latitudinal lines. In this example, the first expandable chamber and the light emitters are on the left side of the cup in this coronal/frontal view. In this example, the second expandable chamber and the light receivers are on the right side of the cup in this coronal/frontal view. In an example, a symmetric variation of this example can be created by reflecting the expandable chambers and optical components across the virtual plane. In this example, a cup for a person's right breast is shown. In an example, a symmetric variation can be used for a cup on a breast on the other side (e.g. right vs. left) of a person's chest.

In this diagram, light emitters are represented by open (e.g. white interior) circles, light receivers are represented by closed (e.g. black interior) circles, light rays from the light emitters are represented by undulating dotted lines, and directional expansion of the expandable chambers is represented by straight dotted line arrows. Example variations discussed elsewhere in this disclosure or in priority-linked disclosures can be applied to this example where relevant.

Figure 6:
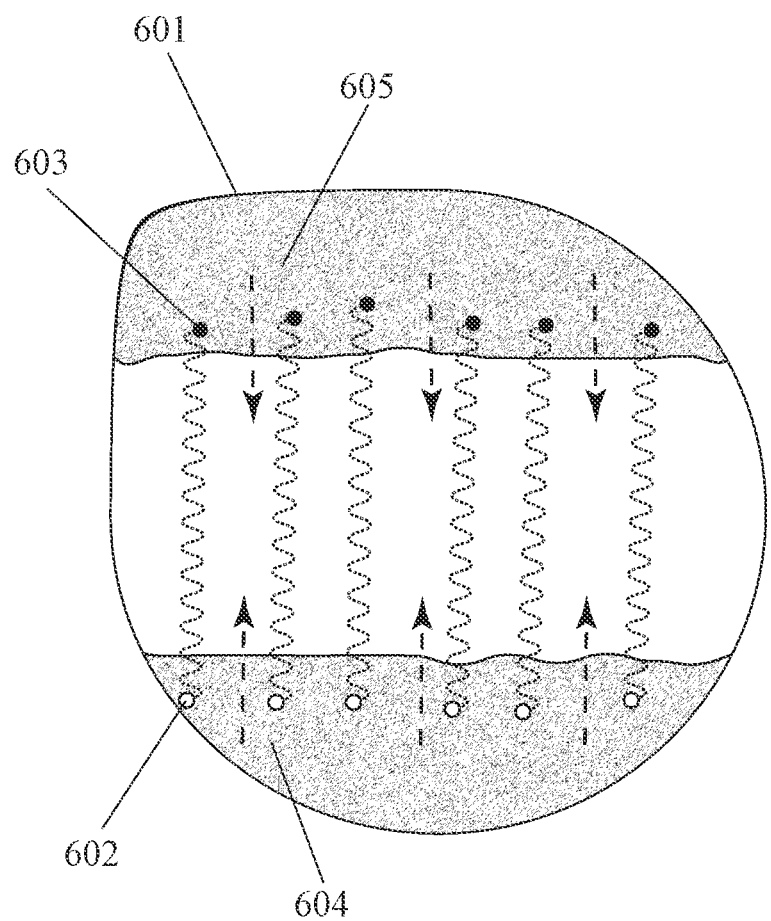
FIG. 6 shows a wearable bra cup for optical analysis of breast tissue with expandable chambers, and light emitters and receivers, on lower and upper portions of the cup.

FIG. 6 shows a coronal (e.g. frontal) cross-sectional view of an example of a wearable device for analyzing breast tissue comprising: a cup which is configured to be worn on a person's breast; a first expandable chamber in a first portion of the cup, wherein the first portion is on a first side of an anterior-to-posterior virtual plane intersecting the cup; a second expandable chamber in a second portion of the cup, wherein the second portion is on a second side of the anterior-to-posterior virtual plane intersecting the cup; a plurality of light emitters in the first portion of the cup; and a plurality of light receivers in the second portion of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

FIG. 6 also shows a coronal (e.g. frontal) cross-sectional view of an example of a wearable device for analyzing breast tissue comprising: a cup worn on a person's breast; a first expandable chamber in a first half of the cup, wherein the first half is on a first side of an anterior-to-posterior virtual plane intersecting the cup; a second expandable chamber in a second half of the cup, wherein the second half is on a second side of the anterior-to-posterior virtual plane intersecting the cup; a plurality of light emitters in the first half of the cup; and a plurality of light receivers in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

With respect to specific components, FIG. 6 shows an example of a wearable device for analyzing breast tissue comprising: a cup 601 worn on a person's breast; a first expandable chamber 604 in a first half of the cup, wherein the first half is on a first side of an anterior-to-posterior virtual plane intersecting the cup; a second expandable chamber 605 in a second half of the cup, wherein the second half is on a second side of the anterior-to-posterior virtual plane intersecting the cup; a plurality of light emitters (including light emitter 602) in the first half of the cup; and a plurality of light receivers (including light receiver 603) in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters (shown in the figure by undulating dotted-line waves) in the plurality of light emitters is received by light receivers in the plurality of light receivers after the light has passed through the portion of the breast, and wherein analysis of light received by the light receivers is used to analyze breast tissue.

In this example, the anterior-to-posterior virtual plane which divides the cup into two sides intersects the 270-degree latitudinal and 90-degree latitudinal lines. In this example, the first expandable chamber and the light emitters are on the bottom side (e.g. bottom half) of the cup in this coronal/frontal view. In this example, the second expandable chamber and the light receivers are on the top side (e.g. top half) of the cup in this coronal/frontal view. In an example, a symmetric variation of this example can be created by reflecting the expandable chambers and optical components across the virtual plane. In this example, a cup for a person's right breast is shown. In an example, a symmetric variation can be used for a cup on a breast on the other side (e.g. right vs. left) of a person's chest.

In this diagram, light emitters are represented by open (e.g. white interior) circles, light receivers are represented by closed (e.g. black interior) circles, light rays from the light emitters are represented by undulating dotted lines, and directional expansion of the expandable chambers is represented by straight dotted line arrows. Example variations discussed elsewhere in this disclosure or in priority-linked disclosures can be applied to this example where relevant.

Figure 7:
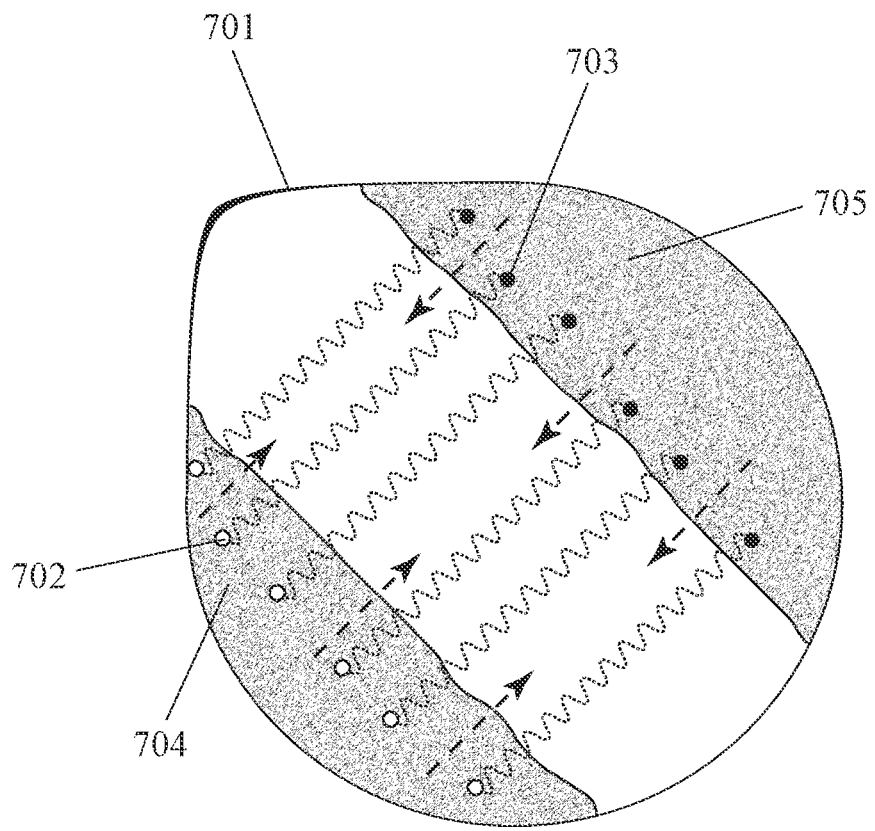
FIG. 7 shows a wearable bra cup for optical analysis of breast tissue with expandable chambers, and light emitters and receivers, on lower-left and upper-right portions of the cup.

FIG. 7 shows a coronal (e.g. frontal) cross-sectional view of an example of a wearable device for analyzing breast tissue comprising: a cup which is configured to be worn on a person's breast; a first expandable chamber in a first portion of the cup, wherein the first portion is on a first side of an anterior-to-posterior virtual plane intersecting the cup; a second expandable chamber in a second portion of the cup, wherein the second portion is on a second side of the anterior-to-posterior virtual plane intersecting the cup; a plurality of light emitters in the first portion of the cup; and a plurality of light receivers in the second portion of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

FIG. 7 also shows a coronal (e.g. frontal) cross-sectional view of an example of a wearable device for analyzing breast tissue comprising: a cup worn on a person's breast; a first expandable chamber in a first half of the cup, wherein the first half is on a first side of an anterior-to-posterior virtual plane intersecting the cup; a second expandable chamber in a second half of the cup, wherein the second half is on a second side of the anterior-to-posterior virtual plane intersecting the cup; a plurality of light emitters in the first half of the cup; and a plurality of light receivers in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

With respect to specific components, FIG. 7 shows an example of a wearable device for analyzing breast tissue comprising: a cup 701 worn on a person's breast; a first expandable chamber 704 in a first half of the cup, wherein the first half is on a first side of an anterior-to-posterior virtual plane intersecting the cup; a second expandable chamber 705 in a second half of the cup, wherein the second half is on a second side of the anterior-to-posterior virtual plane intersecting the cup; a plurality of light emitters (including light emitter 702) in the first half of the cup; and a plurality of light receivers (including light receiver 703) in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters (shown in the figure by undulating dotted-line waves) in the plurality of light emitters is received by light receivers in the plurality of light receivers after the light has passed through the portion of the breast, and wherein analysis of light received by the light receivers is used to analyze breast tissue.

In this example, the anterior-to-posterior virtual plane which divides the cup into two sides intersects the 315-degree latitudinal and 135-degree latitudinal lines. In this example, the first expandable chamber and the light emitters are on the lower-left side of the cup in this coronal/frontal view. In this example, the second expandable chamber and the light receivers are on the upper-right side of the cup in this coronal/frontal view. In an example, a symmetric variation of this example can be created by reflecting the expandable chambers and optical components across the virtual plane. In an example, a vertically-symmetric variation of this example can be created by reflecting the expandable chambers and optical components across a central vertical plane. In this example, a cup for a person's right breast is shown. In an example, a vertically-symmetric variation can be used for a cup on a breast on the other side (e.g. right vs. left) of a person's chest.

In this diagram, light emitters are represented by open (e.g. white interior) circles, light receivers are represented by closed (e.g. black interior) circles, light rays from the light emitters are represented by undulating dotted lines, and directional expansion of the expandable chambers is represented by straight dotted line arrows. Example variations discussed elsewhere in this disclosure or in priority-linked disclosures can be applied to this example where relevant.

Figure 8:
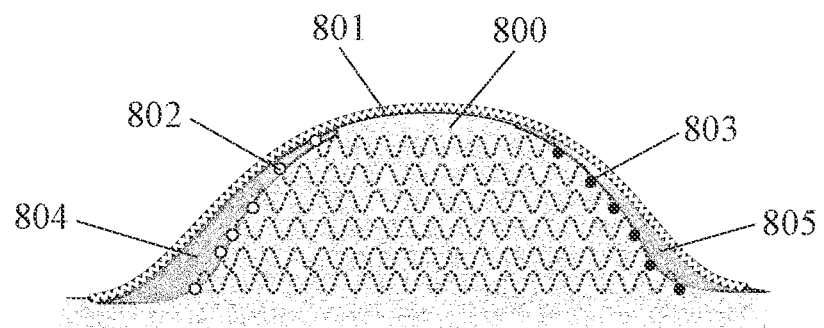
FIGS. 8 and 9 show how a wearable cup for optical analysis of breast tissue with expandable chambers can compress a breast for improved optical scanning.
Figure 9:
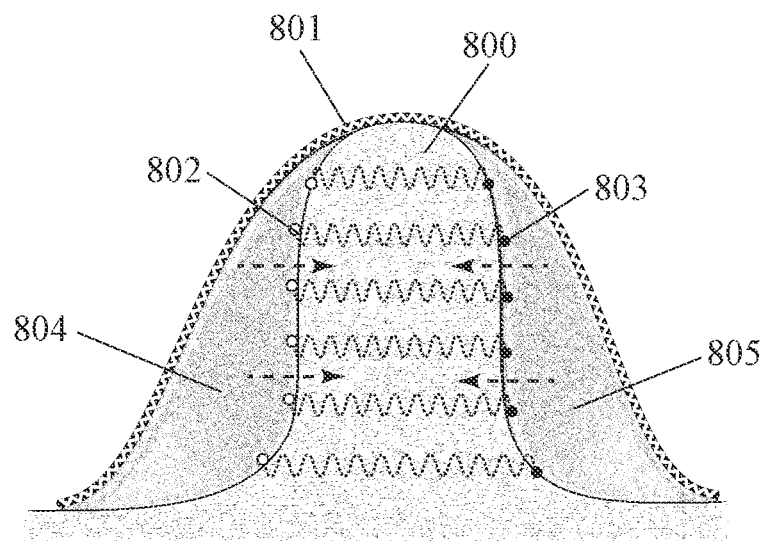

FIGS. 8 and 9 show an example of a wearable device for analyzing breast tissue comprising: a cup which is configured to be worn on a person's breast; a first expandable chamber in a first portion of the cup, wherein the first portion is on a first side of an anterior-to-posterior virtual plane intersecting the cup; a second expandable chamber in a second portion of the cup, wherein the second portion is on a second side of the anterior-to-posterior virtual plane intersecting the cup; a plurality of light emitters in the first portion of the cup; and a plurality of light receivers in the second portion of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

FIGS. 8 and 9 also show two cross-sectional views, at two different times, of an example of a wearable device for analyzing breast tissue comprising: a cup worn on a person's breast; a first expandable chamber in a first half of the cup, wherein the first half is on a first side of an anterior-to-posterior virtual plane intersecting the cup; a second expandable chamber in a second half of the cup, wherein the second half is on a second side of the anterior-to-posterior virtual plane intersecting the cup; a plurality of light emitters in the first half of the cup; and a plurality of light receivers in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

With respect to specific components, FIGS. 8 and 9 show an example of a wearable device for analyzing breast tissue comprising: a cup 801 worn on a person's breast 800; a first expandable chamber 804 in a first half of the cup, wherein the first half is on a first side of an anterior-to-posterior virtual plane intersecting the cup; a second expandable chamber 805 in a second half of the cup, wherein the second half is on a second side of the anterior-to-posterior virtual plane intersecting the cup; a plurality of light emitters (including light emitter 802) in the first half of the cup; and a plurality of light receivers (including light receiver 803) in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters (shown in the figure by undulating dotted-line waves) in the plurality of light emitters is received by light receivers in the plurality of light receivers after the light has passed through the portion of the breast, and wherein analysis of light received by the light receivers is used to analyze breast tissue.

FIG. 8 shows this device at a first point in time when the expandable chambers are not expanded and the device is in the first configuration. FIG. 9 shows this device at a second point in time when the expandable chambers have been expanded and the device is in the second configuration. In the second configuration, expansion of the expandable chambers on either side of a portion of the breast has compressed this portion of the breast into a flatter but more-protruding, shape. This decreases the distance through breast tissue between light emitters and light receivers, thereby decreasing light diffusion and enabling more accurate imaging and/or analysis of breast tissue.

In this diagram, light emitters are represented by open (e.g. white interior) circles, light receivers are represented by closed (e.g. black interior) circles, light rays from the light emitters are represented by undulating dotted lines, and directional expansion of the expandable chambers is represented by straight dotted line arrows. Example variations discussed elsewhere in this disclosure or in priority-linked disclosures can be applied to this example where relevant.

Figure 10:
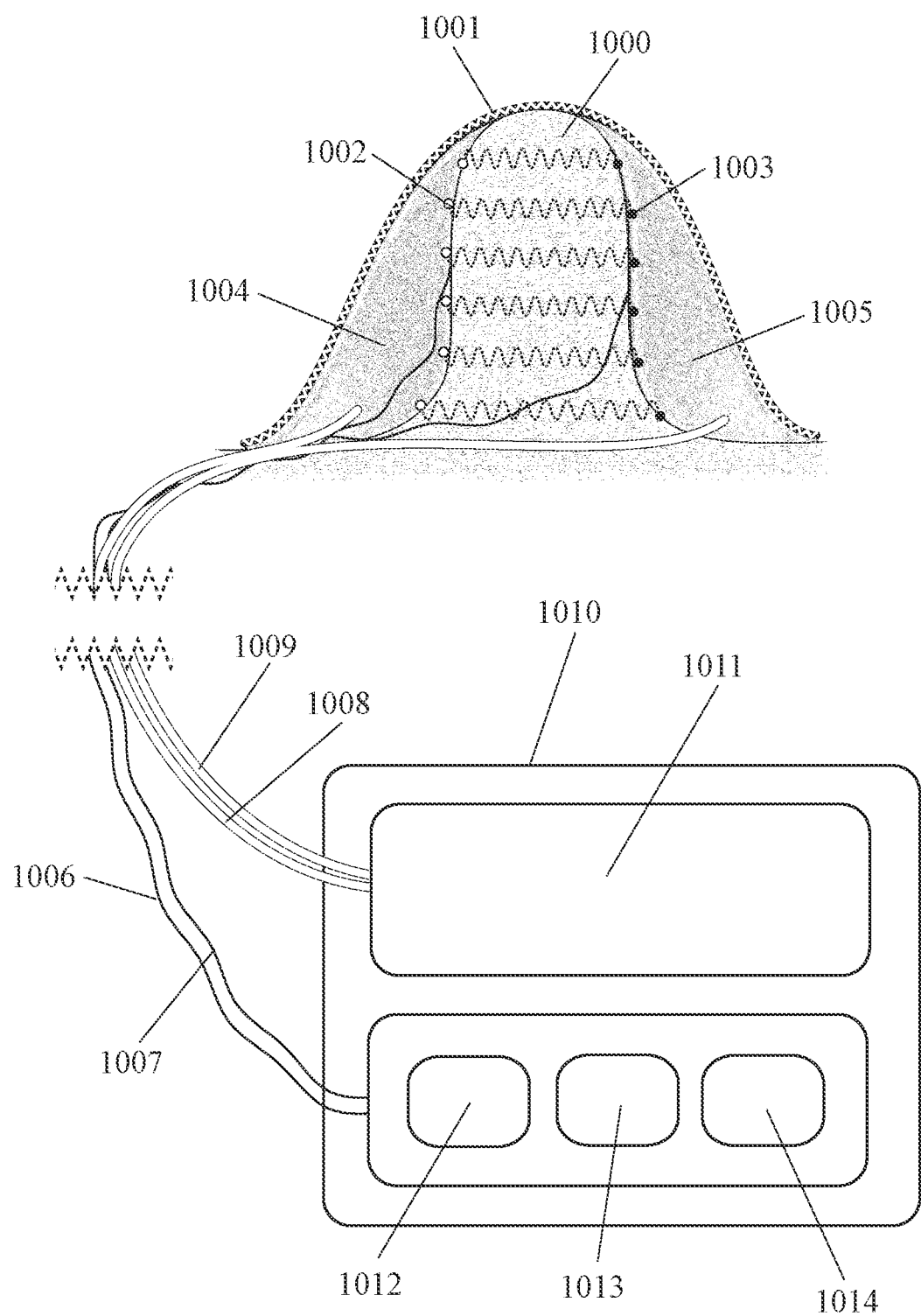
FIG. 10 shows a wearable bra cup for optical analysis of breast tissue with expandable chambers, light emitters and receivers, a pump, and electronic components.

FIG. 10 shows an example of a wearable device for analyzing breast tissue comprising: a cup which is configured to be worn on a person's breast; a first expandable chamber in a first portion of the cup, wherein the first portion is on a first side of an anterior-to-posterior virtual plane intersecting the cup; a second expandable chamber in a second portion of the cup, wherein the second portion is on a second side of the anterior-to-posterior virtual plane intersecting the cup; a plurality of light emitters in the first portion of the cup; and a plurality of light receivers in the second portion of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

FIG. 10 also shows a cross-sectional view of an example of a wearable device or system for analyzing breast tissue comprising: a cup worn on a person's breast; a first expandable chamber in a first half of the cup, wherein the first half is on a first side of an anterior-to-posterior virtual plane intersecting the cup; a second expandable chamber in a second half of the cup, wherein the second half is on a second side of the anterior-to-posterior virtual plane intersecting the cup; a plurality of light emitters in the first half of the cup; a plurality of light receivers in the second half of the cup; a first tube connected to the first expandable chamber; a second tube connected to the second expandable chamber; a first electroconductive pathway connected to light emitters in the plurality of light emitters; a second electroconductive pathway connected to light receivers in the plurality of light receivers; a housing; a pump; a data processor; a data transmitter; and a battery; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein the first expandable chamber is expanded from the first configuration to the second configuration by being filled with a flowable substance from the pump via the first tube, wherein the second expandable chamber is expanded from the first configuration to the second configuration by being filled with a flowable substance from the pump via the second tube, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

With respect to specific components, FIG. 10 shows an example of a wearable device or system for analyzing breast tissue comprising: a cup 1001 worn on a person's breast 1000; a first expandable chamber 1004 in a first half of the cup, wherein the first half is on a first side of an anterior-to-posterior virtual plane intersecting the cup; a second expandable chamber 1005 in a second half of the cup, wherein the second half is on a second side of the anterior-to-posterior virtual plane intersecting the cup; a plurality of light emitters (including light emitter 1002) in the first half of the cup; a plurality of light receivers (including light receiver 1003) in the second half of the cup; a first tube 1008 connected to the first expandable chamber; a second tube 1009 connected to the second expandable chamber; a first electroconductive pathway (e.g. wire) 1006 connected to light emitters in the plurality of light emitters; a second electroconductive pathway (e.g. wire) 1007 connected to light receivers in the plurality of light receivers; a housing 1010; a pump 1011; a data processor 1012; a data transmitter 1013; and a battery 1014; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein the first expandable chamber is expanded from the first configuration to the second configuration by being filled with a flowable substance from the pump via the first tube, wherein the second expandable chamber is expanded from the first configuration to the second configuration by being filled with a flowable substance from the pump via the second tube, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

The upper portion of FIG. 10 shows a cross-sectional view of the cup. The lower portion of FIG. 10 shows a housing containing a pump, data processor, data transmitter, and battery. Zigzag dotted lines indicate diagrammatic discontinuity between the upper and lower portions of the diagram. The housing in the lower portion of FIG. 10 need not be physically below the cup in the upper portion of the diagram. In an example, the housing can be located in a rear (e.g. strap) portion of a smart bra. In an example, the housing can be separate from, and removably connected to, a smart bra and/or bra insert.

In FIG. 10, expandable chambers have been expanded and the device is in the second configuration. Light emitters are represented by open (e.g. white interior) circles, light receivers are represented by closed (e.g. black interior) circles, and light rays from the light emitters are represented by undulating dotted lines. Example variations discussed elsewhere in this disclosure or in priority-linked disclosures can be applied to this example where relevant.

Figure 11:
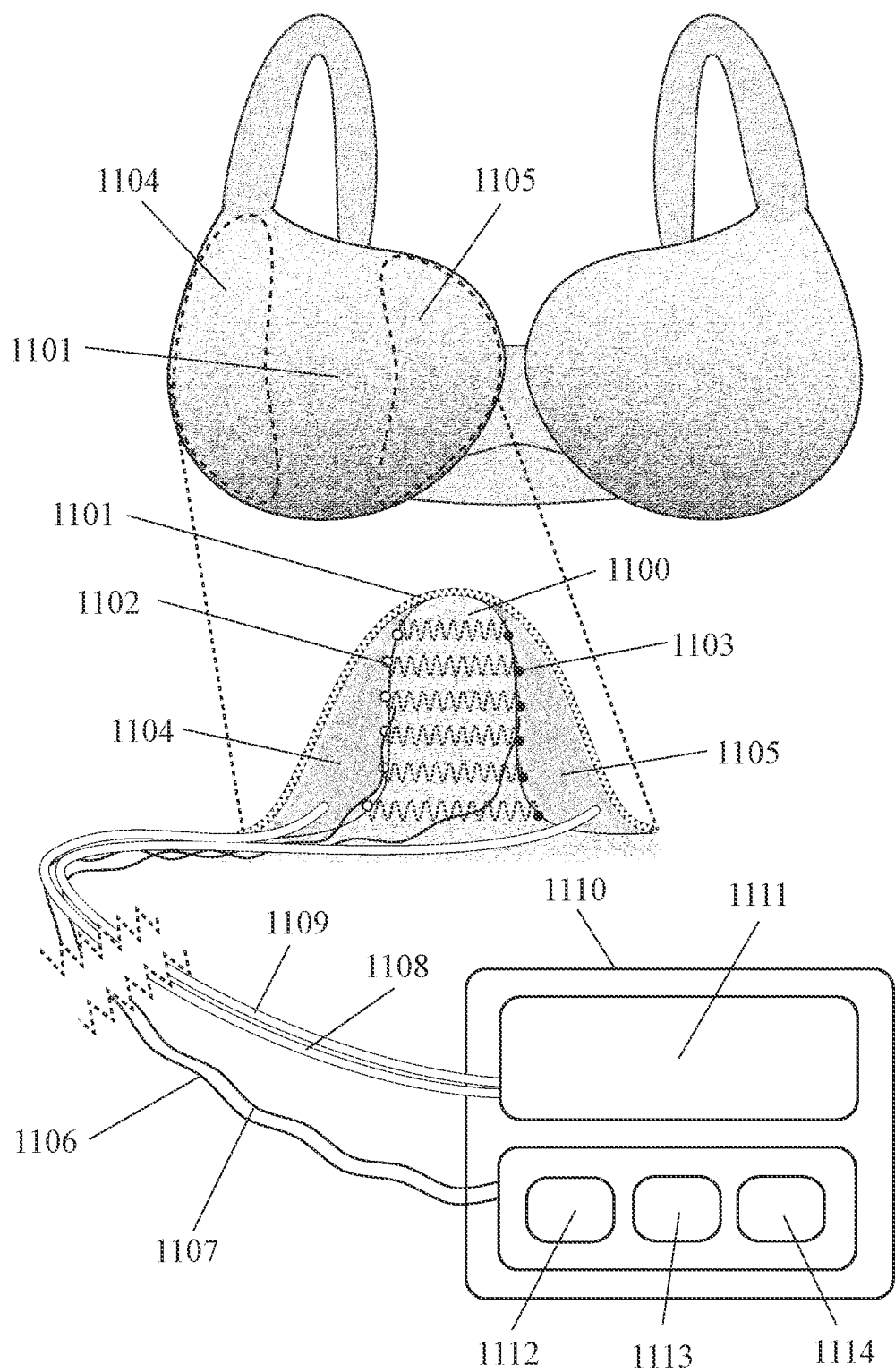
FIG. 11 shows a bra with a cup for optical analysis of breast tissue with expandable chambers, light emitters and receivers, a pump, and electronic components.

FIG. 11 shows an example of a wearable device for analyzing breast tissue comprising: a cup which is configured to be worn on a person's breast; a first expandable chamber in a first portion of the cup, wherein the first portion is on a first side of an anterior-to-posterior virtual plane intersecting the cup; a second expandable chamber in a second portion of the cup, wherein the second portion is on a second side of the anterior-to-posterior virtual plane intersecting the cup; a plurality of light emitters in the first portion of the cup; and a plurality of light receivers in the second portion of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

FIG. 11 also shows an example of a wearable device or system for analyzing breast tissue comprising: a bra cup on a person's breast; a first expandable chamber in a first half of the cup, wherein the first half is on a first side of an anterior-to-posterior virtual plane intersecting the cup; a second expandable chamber in a second half of the cup, wherein the second half is on a second side of the anterior-to-posterior virtual plane intersecting the cup; a plurality of light emitters in the first half of the cup; a plurality of light receivers in the second half of the cup; a first tube connected to the first expandable chamber; a second tube connected to the second expandable chamber; a first electroconductive pathway connected to light emitters in the plurality of light emitters; a second electroconductive pathway connected to light receivers in the plurality of light receivers; a housing; a pump; a data processor; a data transmitter; and a battery; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein the first expandable chamber is expanded from the first configuration to the second configuration by being filled with a flowable substance from the pump via the first tube, wherein the second expandable chamber is expanded from the first configuration to the second configuration by being filled with a flowable substance from the pump via the second tube, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

With respect to specific components, FIG. 11 shows an example of a wearable device or system for analyzing breast tissue comprising: a bra cup 1101 on a person's breast 1100; a first expandable chamber 1104 in a first half of the cup, wherein the first half is on a first side of an anterior-to-posterior virtual plane intersecting the cup; a second expandable chamber 1105 in a second half of the cup, wherein the second half is on a second side of the anterior-to-posterior virtual plane intersecting the cup; a plurality of light emitters (including light emitter 1102) in the first half of the cup; a plurality of light receivers (including light receiver 1103) in the second half of the cup; a first tube 1108 connected to the first expandable chamber; a second tube 1109 connected to the second expandable chamber; a first electroconductive pathway (e.g. wire) 1106 connected to light emitters in the plurality of light emitters; a second electroconductive pathway (e.g. wire) 1107 connected to light receivers in the plurality of light receivers; a housing 1110; a pump 1111; a data processor 1112; a data transmitter 1113; and a battery 1114; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein the first expandable chamber is expanded from the first configuration to the second configuration by being filled with a flowable substance from the pump via the first tube, wherein the second expandable chamber is expanded from the first configuration to the second configuration by being filled with a flowable substance from the pump via the second tube, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

The upper portion of FIG. 11 shows a coronal/frontal view of an overall bra of which the cup is a part. The middle portion of FIG. 11 shows a cross sectional view of the cup. Straight dotted lines connecting the upper and middle portions of FIG. 11 show that the middle portion is an exploded cross-sectional view of one of the bra cups shown in the upper portion. The lower portion of FIG. 11 shows a housing containing a pump, data processor, data transmitter, and battery. Zigzag dotted lines between the middle and lower portions indicate diagrammatic discontinuity between the middle and lower portions of the diagram. The housing in the lower portion of FIG. 11 need not be physically below the cup in the upper portion of the diagram. In an example, the housing can be located in a rear (e.g. strap) portion of the bra. In an example, the housing can be separate from, and removably connected to, the bra.

In FIG. 11, expandable chambers have been expanded and the device is in the second configuration. In FIG. 11, light emitters are represented by open (e.g. white interior) circles, light receivers are represented by closed (e.g. black interior) circles, and light rays from the light emitters are represented by undulating dotted lines. In an example, the cup on the other side of the bra can have a similar (e.g. same, but vertically symmetric) configuration of expanding chambers, light emitters, and light receivers.

In this example, first and second expandable chambers are located to the left and to the right, respectively, of a vertical anterior-to-posterior virtual plane which intersects the cup. In this example, light emitters and light receivers are located to the left and to the right, respectively, of a vertical anterior-to-posterior virtual plane which intersects the cup. In an alternative example, first and second expandable chambers can be located below and above, respectively, a horizontal anterior-to-posterior virtual plane which intersects the cup. In an alternative example, light emitters and light receivers can be located below and above, respectively, a horizontal anterior-to-posterior virtual plane which intersects the cup.

In an alternative example, first and second expandable chambers can be located to the lower left and to the upper right, respectively, of a 45-degree diagonal anterior-to-posterior virtual plane which intersects the cup. In an alternative example, light emitters and light receivers can be located to the lower left and to the upper right, respectively, of a 45-degree diagonal anterior-to-posterior virtual plane which intersects the cup. Example variations discussed elsewhere in this disclosure or in priority-linked disclosures can be applied to this example where relevant.

Figure 12:
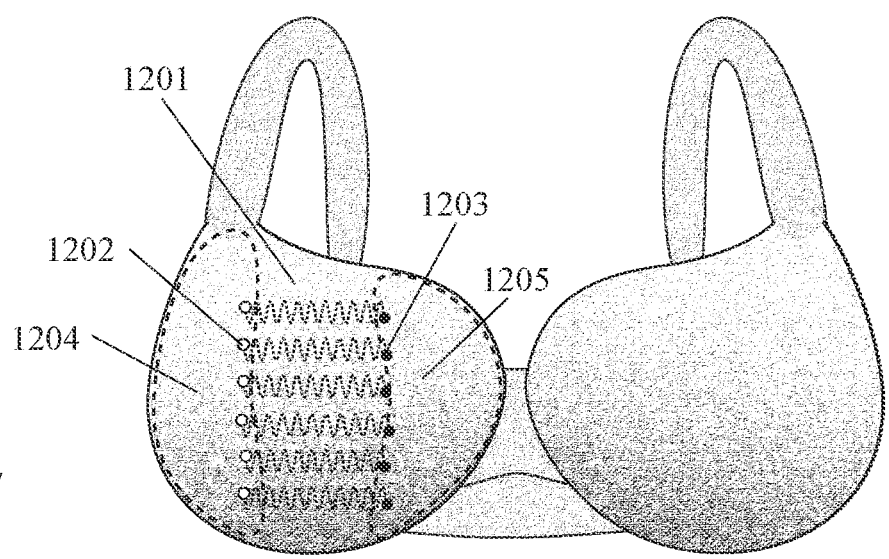
FIG. 12 shows a bra with a cup for optical analysis of breast tissue with expandable chambers to the left and to the right, respectively, of a vertical plane which intersects the cup.

FIG. 12 shows a coronal (e.g. frontal) view of an example of a wearable device for analyzing breast tissue comprising: a cup which is configured to be worn on a person's breast; a first expandable chamber in a first portion of the cup, wherein the first portion is on a first side of an anterior-to-posterior virtual plane intersecting the cup; a second expandable chamber in a second portion of the cup, wherein the second portion is on a second side of the anterior-to-posterior virtual plane intersecting the cup; a plurality of light emitters in the first portion of the cup; and a plurality of light receivers in the second portion of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

FIG. 12 also shows an example of a wearable device for analyzing breast tissue comprising: a bra cup on a person's breast; a first expandable chamber in a first half of the cup, wherein the first half is on a first side of an anterior-to-posterior virtual plane intersecting the cup; a second expandable chamber in a second half of the cup, wherein the second half is on a second side of the anterior-to-posterior virtual plane intersecting the cup; a plurality of light emitters in the first half of the cup; a plurality of light receivers in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

With respect to specific components, FIG. 12 shows an example of a wearable device for analyzing breast tissue comprising: a bra cup 1201 on a person's breast; a first expandable chamber 1204 in a first half of the cup, wherein the first half is on a first side of an anterior-to-posterior virtual plane intersecting the cup; a second expandable chamber 1205 in a second half of the cup, wherein the second half is on a second side of the anterior-to-posterior virtual plane intersecting the cup; a plurality of light emitters (including light emitter 1202) in the first half of the cup; and a plurality of light receivers (including light receiver 1203) in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

FIG. 12 shows a coronal/frontal view of an overall bra of which the cup is a part. Light emitters are represented by open (e.g. white interior) circles, light receivers are represented by closed (e.g. black interior) circles, and light rays from the light emitters are represented by undulating dotted lines. In an example, the cup on the other side of the bra can have a similar (e.g. same, but vertically symmetric) configuration of expanding chambers, light emitters, and light receivers. In this example, first and second expandable chambers are located to the left and to the right, respectively, of a vertical anterior-to-posterior virtual plane which intersects the cup. In this example, light emitters and light receivers are located to the left and to the right, respectively, of a vertical anterior-to-posterior virtual plane which intersects the cup.

In an alternative example, first and second expandable chambers can be located below and above, respectively, a horizontal anterior-to-posterior virtual plane which intersects the cup. In an alternative example, light emitters and light receivers can be located below and above, respectively, a horizontal anterior-to-posterior virtual plane which intersects the cup. In an alternative example, first and second expandable chambers can be located to the lower left and to the upper right, respectively, of a 45-degree diagonal anterior-to-posterior virtual plane which intersects the cup. In an alternative example, light emitters and light receivers can be located to the lower left and to the upper right, respectively, of a 45-degree diagonal anterior-to-posterior virtual plane which intersects the cup. Example variations discussed elsewhere in this disclosure or in priority-linked disclosures can be applied to this example where relevant.

Figure 13:
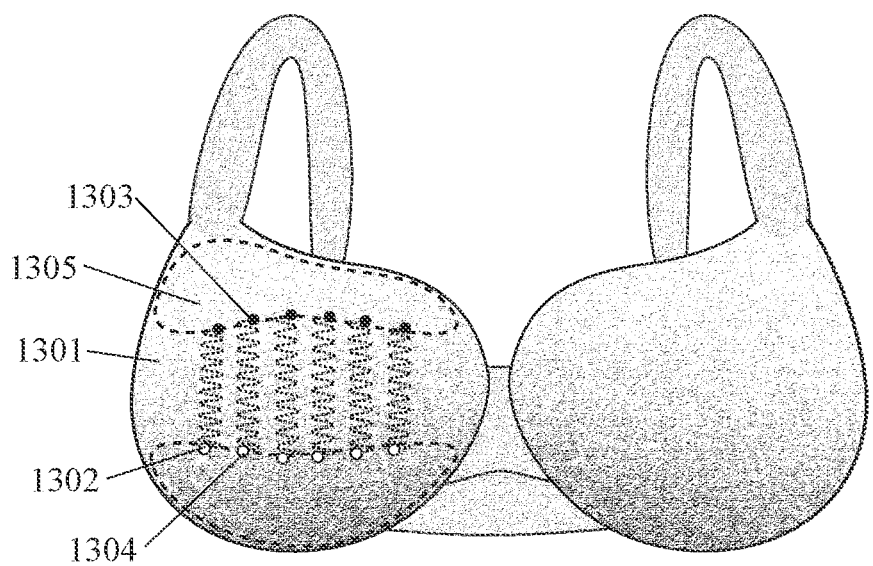
FIG. 13 shows a bra with a cup for optical analysis of breast tissue with expandable chambers below and above, respectively, a horizontal plane which intersects the cup.

FIG. 13 shows a coronal (e.g. frontal) view of an example of a wearable device for analyzing breast tissue comprising: a cup which is configured to be worn on a person's breast;

a first expandable chamber in a first portion of the cup, wherein the first portion is on a first side of an anterior-to-posterior virtual plane intersecting the cup; a second expandable chamber in a second portion of the cup, wherein the second portion is on a second side of the anterior-to-posterior virtual plane intersecting the cup; a plurality of light emitters in the first portion of the cup; and a plurality of light receivers in the second portion of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

FIG. 13 also shows an example of a wearable device for analyzing breast tissue comprising: a bra cup on a person's breast; a first expandable chamber in a first half of the cup, wherein the first half is on a first side of an anterior-to-posterior virtual plane intersecting the cup; a second expandable chamber in a second half of the cup, wherein the second half is on a second side of the anterior-to-posterior virtual plane intersecting the cup; a plurality of light emitters in the first half of the cup; a plurality of light receivers in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

With respect to specific components, FIG. 13 shows an example of a wearable device for analyzing breast tissue comprising: a bra cup 1301 on a person's breast; a first expandable chamber 1304 in a first half of the cup, wherein the first half is on a first side of an anterior-to-posterior virtual plane intersecting the cup; a second expandable chamber 1305 in a second half of the cup, wherein the second half is on a second side of the anterior-to-posterior virtual plane intersecting the cup; a plurality of light emitters (including light emitter 1302) in the first half of the cup; and a plurality of light receivers (including light receiver 1303) in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

FIG. 13 shows a coronal/frontal view of an overall bra of which the cup is a part. Light emitters are represented by open (e.g. white interior) circles, light receivers are represented by closed (e.g. black interior) circles, and light rays from the light emitters are represented by undulating dotted lines. In an example, the cup on the other side of the bra can have a similar (e.g. same, but vertically symmetric) configuration of expanding chambers, light emitters, and light receivers. In this example, first and second expandable chambers are located below and above, respectively, a horizontal anterior-to-posterior virtual plane which intersects the cup. In this example, light emitters and light receivers are located below and above, respectively, a horizontal anterior-to-posterior virtual plane which intersects the cup.

In an alternative example, first and second expandable chambers can be located to the left and to the right, respectively, of a vertical anterior-to-posterior virtual plane which intersects the cup. In an alternative example, light emitters and light receivers can be located to the left and to the right, respectively, of a vertical anterior-to-posterior virtual plane which intersects the cup. In an alternative example, first and second expandable chambers can be located to the lower left and to the upper right, respectively, of a 45-degree diagonal anterior-to-posterior virtual plane which intersects the cup. In an alternative example, light emitters and light receivers can be located to the lower left and to the upper right, respectively, of a 45-degree diagonal anterior-to-posterior virtual plane which intersects the cup. Example variations discussed elsewhere in this disclosure or in priority-linked disclosures can be applied to this example where relevant.

Figure 14:
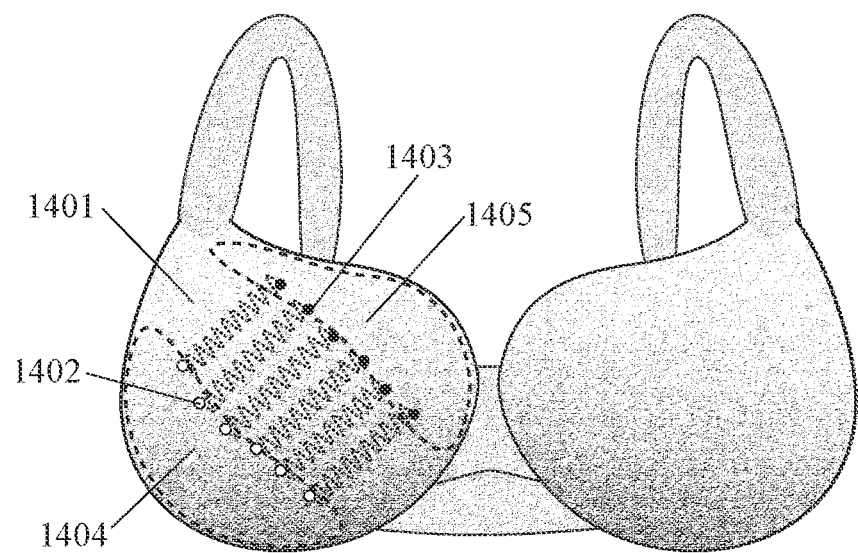
FIG. 14 shows a bra with a cup for optical analysis of breast tissue with expandable chambers on either side, respectively, of a diagonal plane which intersects the cup.

FIG. 14 shows a coronal (e.g. frontal) view of an example of a wearable device for analyzing breast tissue comprising: a cup which is configured to be worn on a person's breast; a first expandable chamber in a first portion of the cup, wherein the first portion is on a first side of an anterior-to-posterior virtual plane intersecting the cup; a second expandable chamber in a second portion of the cup, wherein the second portion is on a second side of the anterior-to-posterior virtual plane intersecting the cup; a plurality of light emitters in the first portion of the cup; and a plurality of light receivers in the second portion of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

FIG. 14 also shows an example of a wearable device for analyzing breast tissue comprising: a bra cup on a person's breast; a first expandable chamber in a first half of the cup, wherein the first half is on a first side of an anterior-to-posterior virtual plane intersecting the cup; a second expandable chamber in a second half of the cup, wherein the second half is on a second side of the anterior-to-posterior virtual plane intersecting the cup; a plurality of light emitters in the first half of the cup; a plurality of light receivers in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

With respect to specific components, FIG. 14 shows an example of a wearable device for analyzing breast tissue comprising: a bra cup 1401 on a person's breast; a first expandable chamber 1404 in a first half of the cup, wherein the first half is on a first side of an anterior-to-posterior virtual plane intersecting the cup; a second expandable chamber 1405 in a second half of the cup, wherein the second half is on a second side of the anterior-to-posterior virtual plane intersecting the cup; a plurality of light emitters (including light emitter 1402) in the first half of the cup; and a plurality of light receivers (including light receiver 1403) in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

FIG. 14 shows a coronal/frontal view of an overall bra of which the cup is a part. Light emitters are represented by open (e.g. white interior) circles, light receivers are represented by closed (e.g. black interior) circles, and light rays from the light emitters are represented by undulating dotted lines. In an example, the cup on the other side of the bra can have a similar (e.g. same, but vertically symmetric) configuration of expanding chambers, light emitters, and light receivers. In this example, first and second expandable chambers are located to the lower left and to the upper right, respectively, of a 45-degree diagonal anterior-to-posterior virtual plane which intersects the cup. In this example, light emitters and light receivers are located to the lower left and to the upper right, respectively, of a 45-degree diagonal anterior-to-posterior virtual plane which intersects the cup.

In an alternative example, first and second expandable chambers can be located below and above, respectively, a horizontal anterior-to-posterior virtual plane which intersects the cup. In an alternative example, light emitters and light receivers can be located below and above, respectively, a horizontal anterior-to-posterior virtual plane which intersects the cup. In an alternative example, first and second expandable chambers can be located to the left and to the right, respectively, of a vertical anterior-to-posterior virtual plane which intersects the cup. In an alternative example, light emitters and light receivers can be located to the left and to the right, respectively, of a vertical anterior-to-posterior virtual plane which intersects the cup. Example variations discussed elsewhere in this disclosure or in priority-linked disclosures can be applied to this example where relevant.

Figure 15:
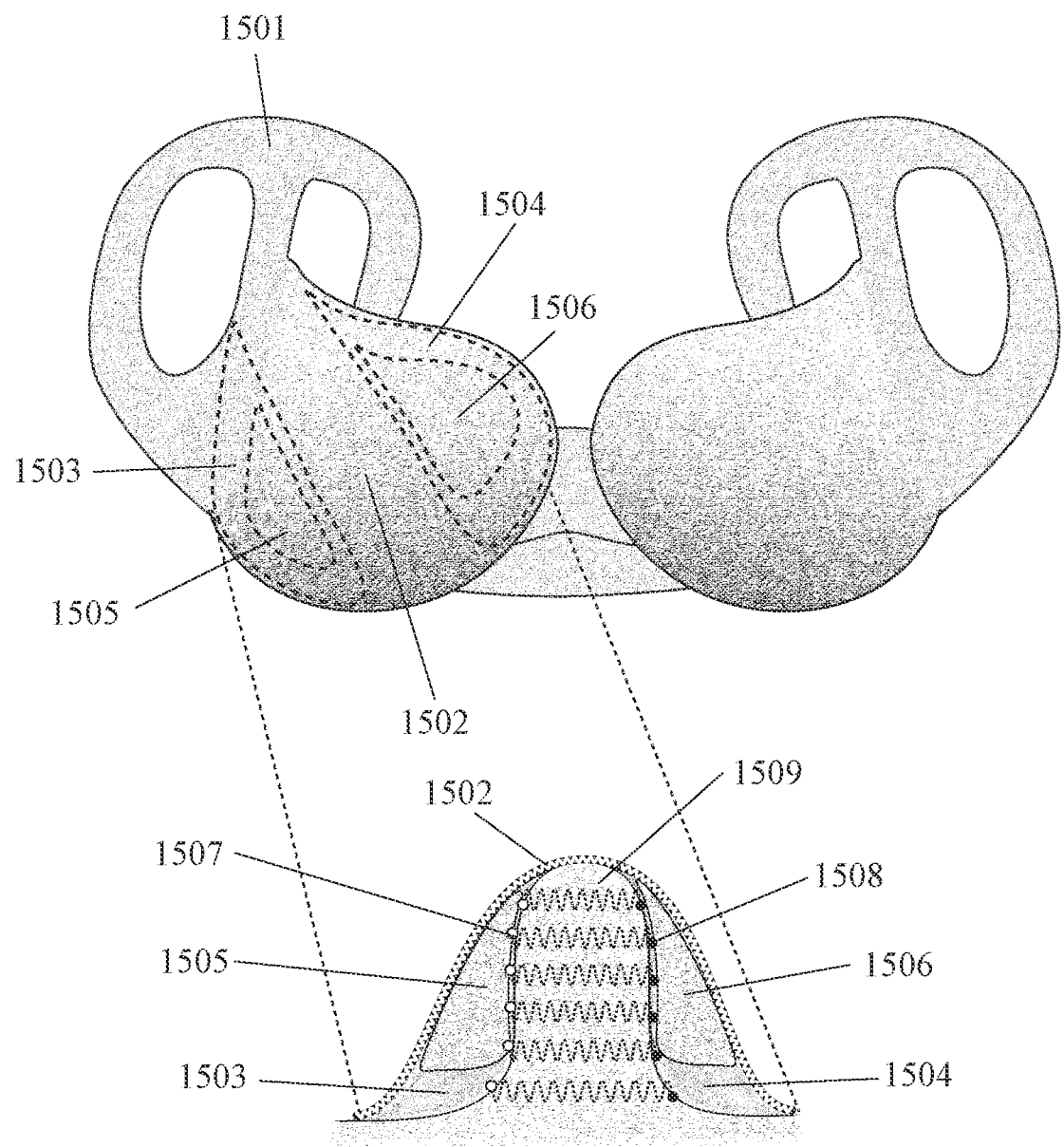
FIG. 15 shows a bra with a cup for optical analysis of breast tissue with two expandable chambers on each side of a diagonal plane which intersects the cup.

FIG. 15 shows an example of a wearable device for analyzing breast tissue comprising: a cup which is configured to be worn on a person's breast; a first expandable chamber in a first portion of the cup, wherein the first portion is on a first side of an anterior-to-posterior virtual plane intersecting the cup; a second expandable chamber in a second portion of the cup, wherein the second portion is on a second side of the anterior-to-posterior virtual plane intersecting the cup; a plurality of light emitters in the first portion of the cup; and a plurality of light receivers in the second portion of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

FIG. 15 also shows an example of a wearable device for analyzing breast tissue comprising: a bra cup on a person's breast; a first expandable chamber in a first half of the cup, wherein the first half is on a first side of an anterior-to-posterior virtual plane intersecting the cup; a second expandable chamber in a second half of the cup, wherein the second half is on a second side of the anterior-to-posterior virtual plane intersecting the cup; a third expandable chamber in the first half of the cup, wherein the third expandable chamber is closer to the apex of the cup than the first expandable chamber; a fourth expandable chamber in the second half of the cup, wherein the fourth expandable chamber is closer to the apex of the cup than the second expandable chamber; a plurality of light emitters in the first half of the cup; a plurality of light receivers in the second half of the cup; wherein the device has a first configuration in which the first, second, third, and fourth expandable chambers are not expanded; wherein the device has a second configuration in which the first, second, third, and fourth expandable chambers are expanded; wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

With respect to specific components, FIG. 15 shows an example of a wearable device for analyzing breast tissue comprising: a cup 1502 on bra 1501 on a person's breast 1509; a first expandable chamber 1503 in a first half of the cup, wherein the first half is on a first side of an anterior-to-posterior virtual plane intersecting the cup; a second expandable chamber 1504 in a second half of the cup, wherein the second half is on a second side of the anterior-to-posterior virtual plane intersecting the cup; a third expandable chamber 1505 in the first half of the cup, wherein the third expandable chamber is closer to the apex of the cup than the first expandable chamber; a fourth expandable chamber 1506 in the second half of the cup, wherein the fourth expandable chamber is closer to the apex of the cup than the second expandable chamber; a plurality of light emitters (including light emitter 1507) in the first half of the cup; a plurality of light receivers (including light receiver 1508) in the second half of the cup; wherein the device has a first configuration in which the first, second, third, and fourth expandable chambers are not expanded; wherein the device has a second configuration in which the first, second, third, and fourth expandable chambers are expanded; wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

The upper portion of FIG. 15 shows a coronal/frontal view of an overall bra of which the cup is a part. The lower portion of FIG. 15 shows a cross sectional view of the cup. Straight dotted lines connecting the upper and lower portions of FIG. 15 show that the lower portion is an exploded cross-sectional view of one of the bra cups shown in the upper portion. Light emitters are represented by open (e.g. white interior) circles, light receivers are represented by closed (e.g. black interior) circles, and light rays from the light emitters are represented by undulating dotted lines. In an example, the cup on the other side of the bra can have a similar (e.g. same, but vertically symmetric) configuration of expanding chambers, light emitters, and light receivers.

In this example, first and second expandable chambers are located to the lower left and to the upper right, respectively, of a 45-degree diagonal anterior-to-posterior virtual plane which intersects the cup. In this example, third and fourth expandable chambers are located to the lower left and to the upper right, respectively, of the 45-degree diagonal anterior-to-posterior virtual plane. In this example, light emitters and light receivers are located to the lower left and to the upper right, respectively, of a 45-degree diagonal anterior-to-posterior virtual plane which intersects the cup.

In this example, there are two expandable chambers on each side of an anterior-to-posterior virtual plane which intersects a bra cup. In this example, one expandable chamber is closer to the apex of a cup or breast than the other expandable chamber on the same side of a virtual plane. In this example, the centroid of one expandable chamber is closer to the apex of a cup or breast than the centroid of the other expandable chamber on the same side of a virtual plane. In this example, the centroid of one expandable chamber is closer to the apex of a cup or breast than the centroid of the other expandable chamber on the same side of a virtual plane when the device is in the first configuration, in the second configuration, or both.

In an example, one expandable chamber can be closer to the surface of a breast than another expandable chamber on the same side of a virtual plane. In an example, the centroid of one expandable chamber can be closer to the surface of a breast than the centroid of another expandable chamber on the same side of a virtual plane. In an example, the centroid of one expandable chamber can be closer to the surface of a breast than the centroid of another expandable chamber on the same side of a virtual plane when the device is in the first configuration, in the second configuration, or both.

In an example, a first expandable chamber can be expanded before a second chamber on the same side of a virtual plane is expanded. In an example, a first expandable chamber can be expanded more than a second chamber on the same side of a virtual plane is expanded. In an example, a first expandable chamber can be expanded by a greater percentage than a second chamber on the same side of a virtual plane is expanded. In an example, a first expandable chamber can be expanded to a greater pressure than that of a second chamber on the same side of a virtual plane. Example variations discussed elsewhere in this disclosure or in priority-linked disclosures can be applied to this example where relevant.

Figure 16:
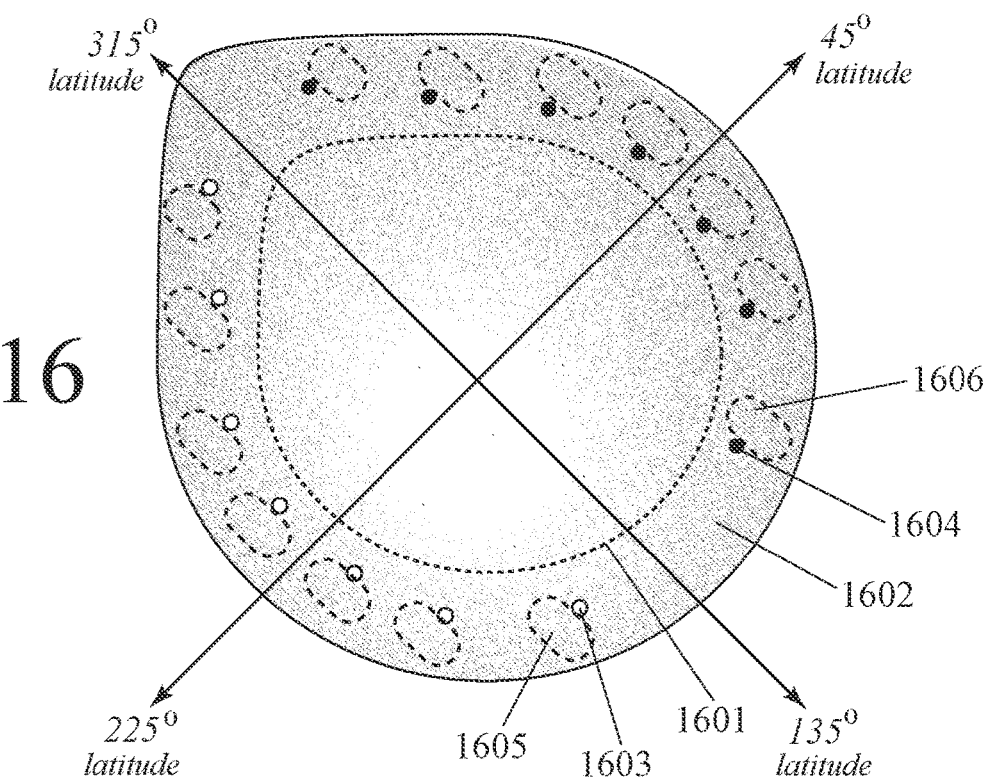
FIGS. 16 and 17 show how a wearable cup for optical analysis of breast tissue with two sets of expandable chambers can compress the breast for improved optical scanning.
Figure 17:
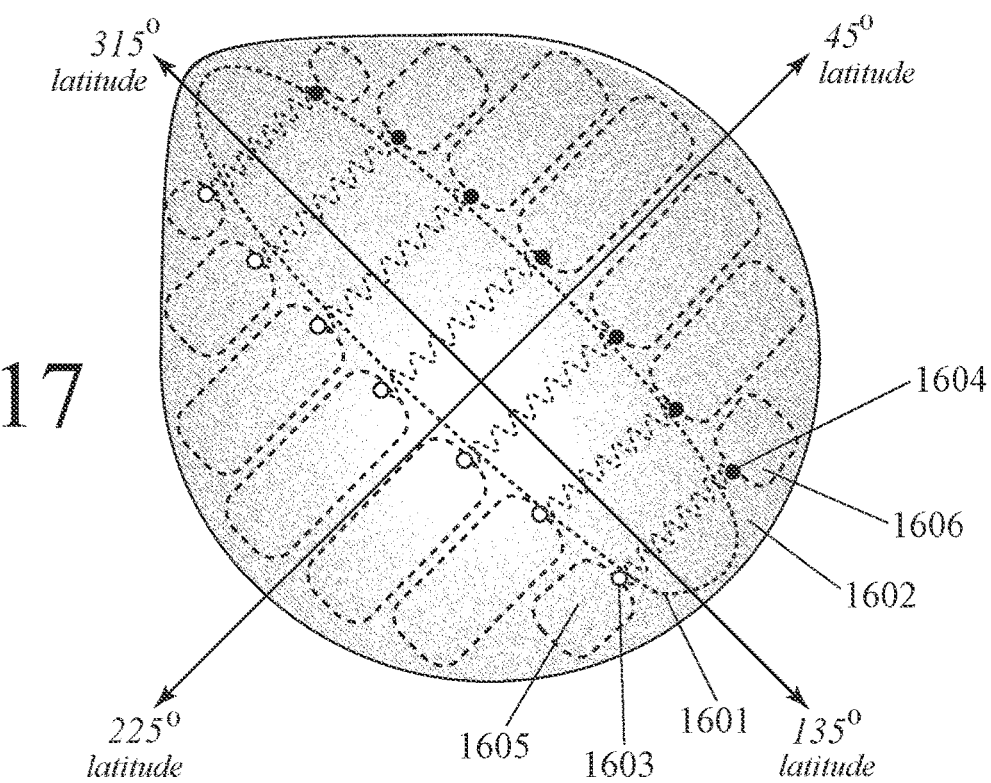

FIGS. 16 and 17 show coronal (e.g. frontal) cross-sectional views of an example of a wearable device for analyzing breast tissue comprising: a cup which is configured to be worn on a person's breast; a first expandable chamber in a first portion of the cup, wherein the first portion is on a first side of an anterior-to-posterior virtual plane intersecting the cup; a second expandable chamber in a second portion of the cup, wherein the second portion is on a second side of the anterior-to-posterior virtual plane intersecting the cup; a plurality of light emitters in the first portion of the cup; and a plurality of light receivers in the second portion of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

FIGS. 16 and 17 also show two cross-sectional views, at two different times, of an example of a wearable device for analyzing breast tissue comprising: a cup worn on a person's breast; a first set of expandable chambers in a first half of the cup, wherein the first half is on a first side of an anterior-to-posterior virtual plane intersecting the cup; a second set of expandable chambers in a second half of the cup, wherein the second half is on a second side of the anterior-to-posterior virtual plane intersecting the cup; a plurality of light emitters in the first half of the cup; and a plurality of light receivers in the second half of the cup; wherein the device has a first configuration in which expandable chambers in the first set and expandable chambers in the second set are not expanded; wherein the device has a second configuration in which expandable chambers in the first set and expandable chambers in the second set are expanded; wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the first set of expandable chambers and the second set of expandable chambers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

With respect to specific components, FIGS. 16 and 17 show two cross-sectional views, at two different times, of an example of a wearable device for analyzing breast tissue comprising: a cup 1602 worn on a person's breast 1601; a first set of expandable chambers (including chamber 1605) in a first half of the cup, wherein the first half is on a first side of an anterior-to-posterior virtual plane intersecting the cup; a second set of expandable chambers (including chamber 1606) in a second half of the cup, wherein the second half is on a second side of the anterior-to-posterior virtual plane intersecting the cup; a plurality of light emitters (including light emitter 1603) in the first half of the cup; and a plurality of light receivers (including light receiver 1604) in the second half of the cup; wherein the device has a first configuration in which expandable chambers in the first set and expandable chambers in the second set are not expanded; wherein the device has a second configuration in which expandable chambers in the first set and expandable chambers in the second set are expanded; wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the first set of expandable chambers and the second set of expandable chambers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

FIG. 16 shows this device at a first point in time when the expandable chambers are not expanded and the device is in the first configuration. FIG. 17 shows this device at a second point in time when the expandable chambers have been expanded and the device is in the second configuration. In the second configuration, expansion of the sets of expandable chambers on either side of a portion of the breast has compressed this portion of the breast into a flatter but more-protruding, shape. This decreases the distance through breast tissue between light emitters and light receivers, thereby decreasing light diffusion and enabling more accurate imaging and/or analysis of breast tissue. Light emitters are represented by open (e.g. white interior) circles, light receivers are represented by closed (e.g. black interior) circles, and light rays from the light emitters are represented by undulating dotted lines.

In this example, first and second sets of expandable chambers are located to the lower left and to the upper right, respectively, of a 45-degree diagonal anterior-to-posterior virtual plane which intersects the cup. In this example, light emitters and light receivers are located to the lower left and to the upper right, respectively, of a 45-degree diagonal anterior-to-posterior virtual plane which intersects the cup.

In this example, first and second sets of expandable chambers are located to the lower left and to the upper right, respectively, of an anterior-to-posterior virtual plane which intersects the cup along the 315-degree latitudinal line and the 135-degree latitudinal line. In this example, light emitters and light receivers are located to the lower left and to the upper right, respectively, of an anterior-to-posterior virtual plane which intersects the cup along the 315-degree latitudinal line and the 135-degree latitudinal line. In an example, the cup on the other side of the bra can have a similar (e.g. same, but vertically symmetric) configuration of expanding chambers, light emitters, and light receivers.

In an example, all expandable chambers in a set of expandable chambers on the same side of a virtual plane can be expanded by the same amount (e.g. by the same percentage or to the same internal pressure level). In an example, different expandable chambers in a set of expandable chambers on the same side of a virtual plane can be expanded by different amounts (e.g. by different percentages or to different internal pressure levels). In an example, expandable chambers which are closer to the apex of a cup or breast can be expanded more than expandable chambers which are farther from the apex of a cup or breast. As shown in FIG. 17, differential expansion of different chambers in a set of expandable chambers can help to compress a portion of a breast into a shape with a more-uniform width (e.g. a flatter shape). In an example, expandable chambers in a set of expandable chambers on the same side of a virtual plane can expand along parallel vectors. Alternatively, expandable chambers in a set of expandable chambers can expand along non-parallel vectors. Example variations discussed elsewhere in this disclosure or in priority-linked disclosures can be applied to this example where relevant.

Figure 18:
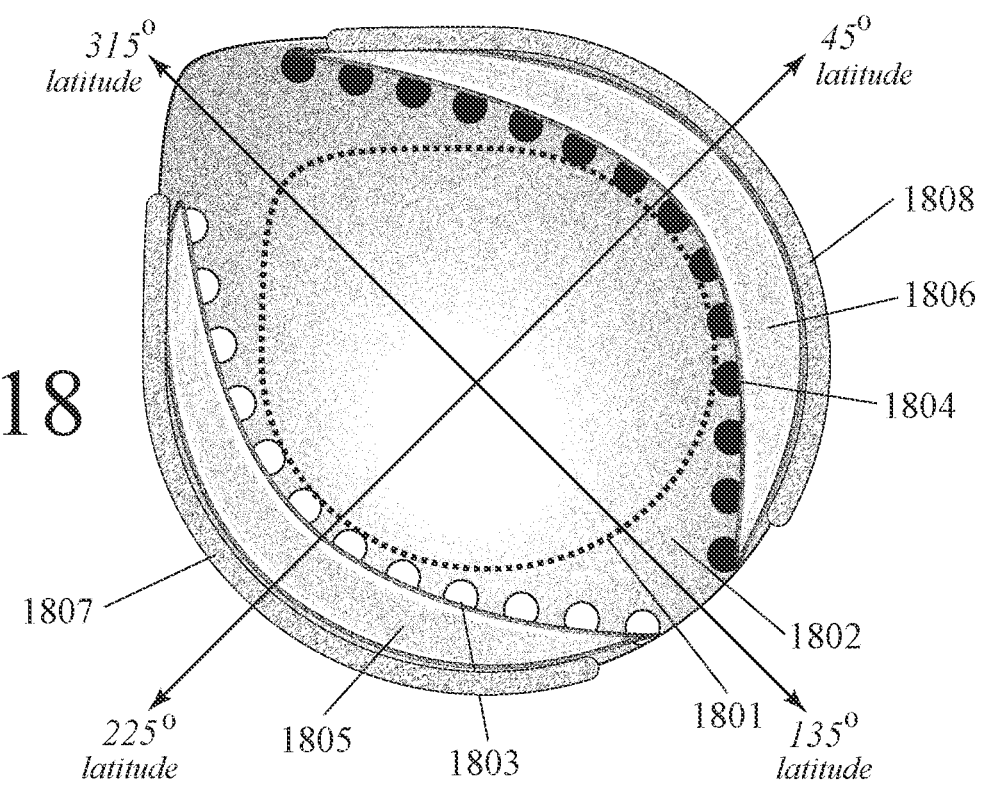
FIGS. 18 and 19 show a wearable cup for optical analysis of breast tissue with inflexible peripheral sections for directed breast compression for improved optical scanning.
Figure 19:
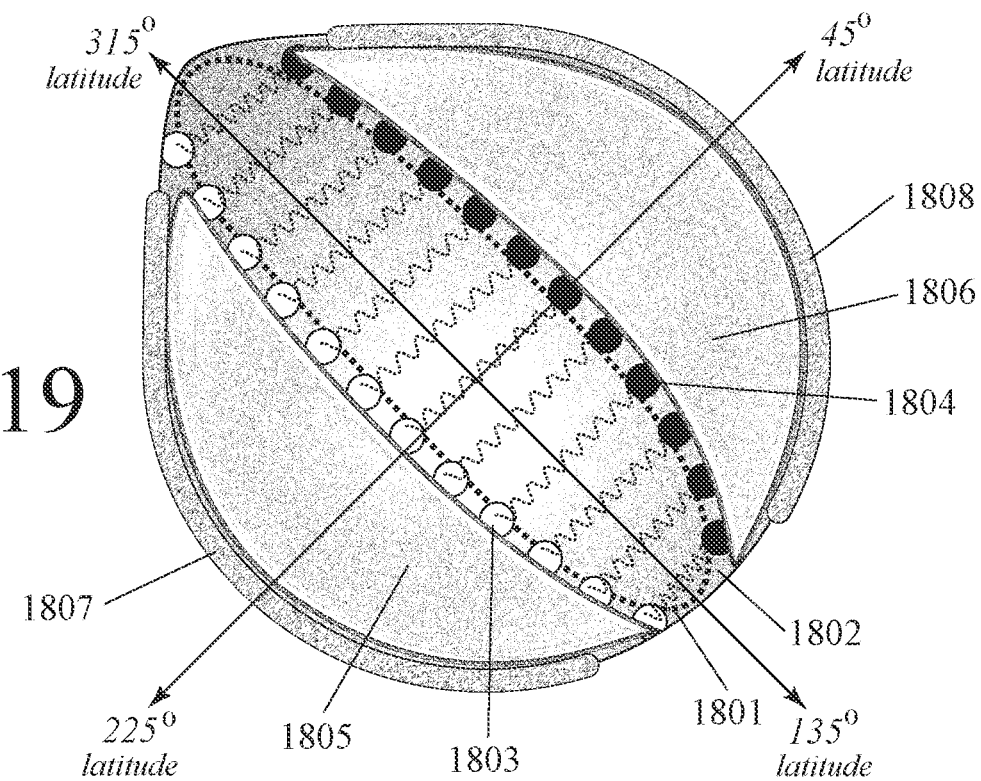

FIGS. 18 and 19 show coronal (e.g. frontal) cross-sectional views of an example of a wearable device for analyzing breast tissue comprising: a cup which is configured to be worn on a person's breast; a first expandable chamber in a first portion of the cup, wherein the first portion is on a first side of an anterior-to-posterior virtual plane intersecting the cup; a second expandable chamber in a second portion of the cup, wherein the second portion is on a second side of the anterior-to-posterior virtual plane intersecting the cup; a plurality of light emitters in the first portion of the cup; and a plurality of light receivers in the second portion of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

FIGS. 18 and 19 also show two cross-sectional views, at two different times, of an example of a wearable device for analyzing breast tissue comprising: a generally-elastic cup worn on a person's breast; a first inelastic section of the cup around part of the perimeter of a first half of the cup, wherein the first half is on a first side of an anterior-to-posterior virtual plane intersecting the cup; a second inelastic section of the cup around part of the perimeter of a second half of the cup, wherein the second half is on a second side of the anterior-to-posterior virtual plane intersecting the cup; a first expandable chamber in the first half of the cup; a second expandable chamber in the second half of the cup; a plurality of light emitters in the first half of the cup; and a plurality of light receivers in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

With respect to specific components, FIGS. 18 and 19 show an example of a wearable device for analyzing breast tissue comprising: a generally-elastic cup 1802 worn on a person's breast 1801; a first inelastic section 1807 of the cup around part of the perimeter of a first half of the cup, wherein the first half is on a first side of an anterior-to-posterior virtual plane intersecting the cup; a second inelastic section 1808 of the cup around part of the perimeter of a second half of the cup, wherein the second half is on a second side of the anterior-to-posterior virtual plane intersecting the cup; a first expandable chamber 1805 in the first half of the cup; a second expandable chamber 1806 in the second half of the cup; a plurality of light emitters (including light emitter 1803) in the first half of the cup; and a plurality of light receivers (including light receiver 1804) in the second half of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

FIG. 18 shows this device at a first point in time when the expandable chambers are not expanded and the device is in the first configuration. FIG. 19 shows this device at a second point in time when the expandable chambers have been expanded and the device is in the second configuration. In the second configuration, expansion of the expandable chambers on either side of a portion of the breast has compressed this portion of the breast into a flatter shape. This decreases the distance through breast tissue between light emitters and light receivers, thereby decreasing light diffusion and enabling more accurate imaging and/or analysis of breast tissue. Light emitters are represented by open (e.g. white interior) circles, light receivers are represented by closed (e.g. black interior) circles, and light rays from the light emitters are represented by undulating dotted lines.

In an example, an inelastic portion of a cup causes an expandable chamber to expand inward into breast tissue (more than outward through expansion of the outer perimeter of the cup). This can help to flatten the breast for improved optical scanning. In an example, inelastic portions of a cup can have a higher Young's modulus than the rest of the cup. In an example, inelastic portions of a cup can have a higher Young's modulus than the other portions of the cup. In an example, inelastic portions of a cup can be rigid or inflexible. In an example, inelastic portions of a cup can comprise wire reinforcement of the portion of the cup. In an example, inelastic portions of a cup can comprise reinforcement of the portion of the cup with metal or plastic.

In this example, first and second sets of expandable chambers are located to the lower left and to the upper right, respectively, of a 45-degree diagonal anterior-to-posterior virtual plane which intersects the cup. In this example, light emitters and light receivers are located to the lower left and to the upper right, respectively, of a 45-degree diagonal anterior-to-posterior virtual plane which intersects the cup. In this example, first and second sets of expandable chambers are located to the lower left and to the upper right, respectively, of an anterior-to-posterior virtual plane which intersects the cup along the 315-degree latitudinal line and the 135-degree latitudinal line. In this example, light emitters and light receivers are located to the lower left and to the upper right, respectively, of an anterior-to-posterior virtual plane which intersects the cup along the 315-degree latitudinal line and the 135-degree latitudinal line. In an example, the cup on the other side of the bra can have a similar (e.g. same, but vertically symmetric) configuration of expanding chambers, light emitters, and light receivers. Example variations discussed elsewhere in this disclosure or in priority-linked disclosures can be applied to this example where relevant.

In an example, a wearable device for analyzing breast tissue can comprise: a cup which is configured to be worn on a person's breast; a first expandable chamber in a first portion of the cup, wherein the first portion is on a first side of an anterior-to-posterior virtual plane intersecting the cup; a second expandable chamber in a second portion of the cup, wherein the second portion is on a second side of the anterior-to-posterior virtual plane intersecting the cup; a plurality of light emitters in the first portion of the cup; and a plurality of light receivers in the second portion of the cup; wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein a portion of the breast is between the plurality of light emitters and the plurality of light receivers, wherein the portion of the breast is compressed in the second configuration, wherein light from light emitters in the plurality of light emitters is received by light receivers in the plurality of light receivers after the light has passed through the portion of the breast, and wherein analysis of light received by the light receivers is used to analyze breast tissue.

In an example, the plane can be parallel to 0-degree and 180-degree latitudinal lines of the cup. In an example, the first portion of the cup can be to the right of the plane and the second portion of the cup can be to the left of the plane. In an example, the first portion of the cup can be to the left of the plane and the second portion of the cup can be to the right of the plane. In an example, the plane can be parallel to 270-degree and 90-degree latitudinal lines of the cup. In an example, the first portion of the cup can be below the plane and the second portion of the cup can be above the plane. In an example, the first portion of the cup can be above the plane and the second portion of the cup can be below the plane.

In an example, the plane can be parallel to 315-degree and 135-degree latitudinal lines of the cup. In an example, the first portion of the cup can be to the lower left of the plane and the second portion of the cup can be to the upper right of the plane. In an example, the first portion of the cup can be to the upper right of the plane and the second portion of the cup can be to the lower left of the plane. In an example, the plane can be parallel to 225-degree and 45-degree latitudinal lines of the cup. In an example, the first portion of the cup can be to the lower right of the plane and the second portion of the cup can be to the upper left of the plane. In an example, the first portion of the cup can be to the upper left of the plane and the second portion of the cup can be to the lower right of the plane.

In an example, the plurality of light emitters are no closer than ¼ inch from the plane and the plurality of light receivers are no closer than ¼ inch from the plane. In an example, the plurality of light emitters are no closer than ½ inch from the plane and the plurality of light receivers are no closer than ½ inch from the plane. In an example, the plurality of light emitters are no closer than 1 inch from the plane and the plurality of light receivers are no closer than 1 inch from the plane.

In an example, the first expandable chamber and the second expandable chamber can be expanded by being filled with a gas. In an example, the first expandable chamber and the second expandable chamber can be expanded by being filled with a liquid. In an example, the wearable device can be a bra. In an example, the wearable device can be inserted into a bra cup.

I claim:

1. A wearable device for analyzing breast tissue comprising:
- a cup which is configured to be worn on a person's breast, wherein the cup further comprises an array of elastic rings, and wherein elastic rings of the array of elastic rings which are closer to an apex of the cup are more elastic than elastic rings of the array of elastic rings which are farther from the apex;
- a first expandable chamber in a first portion of the cup, wherein the first portion is on a first side of a plane intersecting the cup;
- a second expandable chamber in a second portion of the cup, wherein the second portion is on a second side of the plane intersecting the cup;
- a plurality of light emitters in the first portion of the cup; and
- a plurality of light receivers in the second portion of the cup;
- wherein the device has a first configuration in which the first expandable chamber has a first size and the second expandable chamber has a second size, wherein the device has a second configuration in which the first expandable chamber has a third size and the second expandable chamber has a fourth size, wherein the third size is greater than the first size, wherein the fourth size is greater than the second size, wherein there is a first average distance between the plurality of light emitters and the plurality of light receivers in the first configuration, wherein there is a second average distance between the plurality of light emitters and the plurality of light receivers in the second configuration, wherein the second average distance is less than the first average distance, wherein the cup is configured to compress a portion of the breast in the second configuration, wherein the plurality of light emitters are configured to transmit light through a portion of the breast, and wherein the plurality of light receivers are configured to receive light that has passed through a portion of the breast, and wherein analysis of light received by the light receivers is used to analyze breast tissue.

* * * * *